United States Patent
Parham et al.

(10) Patent No.: US 10,644,246 B2
(45) Date of Patent: May 5, 2020

(54) MATERIALS FOR ORGANIC ELECTROLUMINESCENT DEVICES

(71) Applicant: Merck Patent GmbH, Darmstadt (DE)

(72) Inventors: Amir Hossain Parham, Frankfurt am Main (DE); Philipp Stoessel, Frankfurt am Main (DE); Thomas Eberle, Landau (DE); Anja Jatsch, Frankfurt am Main (DE); Jonas Valentin Kroeber, Frankfurt am Main (DE); Tobias Grossmann, Darmstadt (DE); Christof Pflumm, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 118 days.

(21) Appl. No.: 15/321,788

(22) PCT Filed: May 29, 2015

(86) PCT No.: PCT/EP2015/001096
§ 371 (c)(1),
(2) Date: Dec. 23, 2016

(87) PCT Pub. No.: WO2015/197156
PCT Pub. Date: Dec. 30, 2015

(65) Prior Publication Data
US 2017/0141327 A1    May 18, 2017

(30) Foreign Application Priority Data
Jun. 25, 2014  (EP) .................................... 14002178

(51) Int. Cl.
| | |
|---|---|
| *H01L 51/50* | (2006.01) |
| *H01L 51/00* | (2006.01) |
| *C07D 491/107* | (2006.01) |
| *C07D 491/20* | (2006.01) |
| *C07D 495/20* | (2006.01) |
| *C09K 11/06* | (2006.01) |
| *C07D 311/96* | (2006.01) |
| *C07D 209/96* | (2006.01) |
| *C07D 409/12* | (2006.01) |
| *C07D 407/12* | (2006.01) |
| *C09K 11/02* | (2006.01) |
| *H01L 51/42* | (2006.01) |
| *H01L 51/05* | (2006.01) |

(52) U.S. Cl.
CPC ........ *H01L 51/0071* (2013.01); *C07D 209/96* (2013.01); *C07D 311/96* (2013.01); *C07D 407/12* (2013.01); *C07D 409/12* (2013.01); *C07D 491/107* (2013.01); *C07D 491/20* (2013.01); *C07D 495/20* (2013.01); *C09K 11/025* (2013.01); *C09K 11/06* (2013.01); *H01L 51/0052* (2013.01); *H01L 51/0067* (2013.01); *H01L 51/0072* (2013.01); *H01L 51/0073* (2013.01); *C09K 2211/185* (2013.01); *H01L 51/05* (2013.01); *H01L 51/42* (2013.01); *H01L 51/5016* (2013.01); *H01L 51/5056* (2013.01); *H01L 51/5072* (2013.01); *H01L 51/5096* (2013.01)

(58) Field of Classification Search
None
See application file for complete search history.

(56) References Cited

U.S. PATENT DOCUMENTS

| 9,780,311 B2 | 10/2017 | Parham et al. | |
| 2017/0217992 A1* | 8/2017 | Jun ...................... | C07D 519/00 |

FOREIGN PATENT DOCUMENTS

| CN | 101440082 A | 5/2009 |
| CN | 102786508 A | 11/2012 |
| CN | 103664860 A | 3/2014 |
| CN | 103666454 A | 3/2014 |
| JP | 2010202599 A | 9/2010 |
| WO | WO-2013017189 A1 | 2/2013 |
| WO | WO-2013149958 A1 | 10/2013 |
| WO | WO-2013151297 A1 | 10/2013 |
| WO | WO-2014072107 A1 | 5/2014 |

OTHER PUBLICATIONS

International Search Report for PCT/EP2015/001096 dated Oct. 19, 2015.
Written Opinion of the International Searching Authority for PCT/EP2015/001096 dated Oct. 19, 2015.

* cited by examiner

*Primary Examiner* — Gregory D Clark
(74) *Attorney, Agent, or Firm* — Drinker Biddle & Reath LLP

(57) ABSTRACT

The invention relates to compounds which are suitable for use in electronic devices, and to electronic devices, in particular organic electroluminescent devices, containing said compounds.

14 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2015/001096, filed May 29, 2015, which claims benefit of European Application No. 14002178.3, filed Jun. 25, 2014, both of which are incorporated herein by reference in their entirety.

The present invention relates to materials for use in electronic devices, especially in organic electroluminescent devices, and to electronic devices, especially organic electroluminescent devices, comprising these materials.

The structure of organic electroluminescent devices (OLEDs) in which organic semiconductors are used as functional materials is described, for example, in U.S. Pat. Nos. 4,539,507, 5,151,629, EP 0676461 and WO 98/27136. Emitting materials used here are increasingly organometallic complexes which exhibit phosphorescence rather than fluorescence. For quantum-mechanical reasons, up to four times the energy efficiency and power efficiency is possible using organometallic compounds as phosphorescent emitters. In general terms, however, there is still a need for improvement in OLEDs, especially also in OLEDs which exhibit triplet emission (phosphorescence), for example with regard to efficiency, operating voltage and lifetime.

The properties of phosphorescent OLEDs are not just determined by the triplet emitters used. More particularly, the other materials used, such as matrix materials, are also of particular significance here. Improvements to these materials and the charge transport properties thereof can thus also lead to distinct improvements in the OLED properties.

According to the prior art, indolocarbazole derivatives, for example according to WO 2007/063754 or WO 2008/056746, indenocarbazole derivatives, for example according to WO 2010/136109, or fluorene or spirobifluorene derivatives, for example according to WO 2012/074210, are among the matrix materials used for phosphorescent emitters in organic electroluminescent devices. Further improvements are desirable here, especially in relation to efficiency, lifetime and operating voltage.

It is an object of the present invention to provide compounds suitable for use in an OLED, especially as matrix material for phosphorescent emitters. It is a further object of the present invention to provide further organic semiconductors for organic electroluminescent devices, in order thus to enable the person skilled in the art to have a greater possible choice of materials for the production of OLEDs.

It has been found that, surprisingly, particular compounds described below achieve this object and are of good suitability for use in OLEDs and lead to improvements in the organic electroluminescent device. These improvements relate particularly to the lifetime, efficiency and/or operating voltage. The present invention therefore provides these compounds and electronic devices, especially organic electroluminescent devices, comprising such compounds.

WO 2013/017189 discloses spirobifluorene derivatives with a fused-on carbazole unit. Compounds according to the present invention are not disclosed, nor is it disclosed that compounds having an oxygen or sulfur bridge lead to technical advantages.

The present invention therefore provides a compound of formula (I)

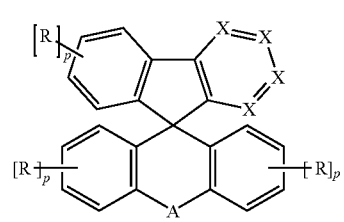

formula (1)

where the symbols and indices used are as follows:
A is O or S;
X two adjacent X are a group of the following formula (2):

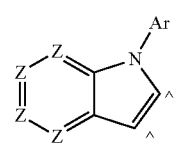

formula (2)

where ^ indicates the corresponding adjacent X groups in formula (1); and the two remaining X groups are CR;
Z is CR; or two adjacent Z are a group of the following formula (2a) and the two other Z are CR,

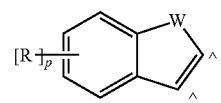

formula (2a)

where ^ indicates the corresponding adjacent Z groups in formula (2); W here is O, S, NR or $CR_2$;
Ar is an aromatic or heteroaromatic ring system which has 5 to 40 aromatic ring atoms and may be substituted by one or more R radicals;
R is the same or different at each instance and is selected from the group consisting of H, D, F, Cl, Br, I, CN, $NO_2$, $N(Ar^1)_2$, $N(R^1)_2$, $C(=O)Ar^1$, $C(=O)R^1$, $P(=O)(Ar^1)_2$, $P(Ar^1)_2$, $B(Ar^1)_2$, $Si(Ar^1)_3$, $Si(R^1)_3$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, each of which may be substituted by one or more $R^1$ radicals, where one or more nonadjacent $CH_2$ groups may be replaced by $R^1C=CR^1$, C≡C, $Si(R^1)_2$, C=O, C=S, $C=NR^1$, $P(=O)(R^1)$, SO, $SO_2$, $NR^1$, O, S or $CONR^1$ and where one or more hydrogen atoms may be replaced by D, F, Cl, Br, I, CN or $NO_2$, an aromatic or heteroaromatic ring system which has 5 to 60 aromatic ring atoms and may be substituted in each case by one or more $R^1$ radicals, an aryloxy or heteroaryloxy group which has 5 to 40 aromatic ring atoms and may be substituted by one or more $R^1$ radicals; at the same time, it is optionally possible for two adjacent R substituents to form a monocyclic or polycyclic, aliphatic, aromatic or heteroaromatic ring system which may be substituted by one or more $R^1$ radicals;
$Ar^1$ is the same or different at each instance and is an aromatic or heteroaromatic ring system which has 5 to 30 aromatic ring atoms and may be substituted by one or more nonaromatic $R^1$ radicals; at the same time, two $Ar^1$ radicals bonded to the same nitrogen, phosphorus, boron or silicon atom may also be bridged to one another by a single bond or a bridge selected from $N(R^1)$, $C(R^1)_2$, O and S;

$R^1$ is the same or different at each instance and is selected from the group consisting of H, D, F, CN, an aliphatic hydrocarbyl radical having 1 to 20 carbon atoms, or an aromatic or heteroaromatic ring system having 5 to 30 aromatic ring atoms in which one or more hydrogen atoms may be replaced by D, F, CN or an alkyl group having 1 to 10 carbon atoms; at the same time, two or more adjacent $R^1$ substituents together may form a mono- or polycyclic, aliphatic ring system;

p is the same or different at each instance and is 0, 1, 2, 3 or 4.

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused (annelated) aryl or heteroaryl group, for example naphthalene, anthracene, phenanthrene, quinoline, isoquinoline, etc. Aromatic systems joined to one another by a single bond, for example biphenyl, by contrast, are not referred to as an aryl or heteroaryl group but as an aromatic ring system.

An aromatic ring system in the context of this invention contains 6 to 60 carbon atoms in the ring system. A heteroaromatic ring system in the context of this invention contains 2 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a nonaromatic unit, for example a carbon, nitrogen or oxygen atom. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are joined, for example, by a short alkyl group.

In the context of the present invention, an aliphatic hydrocarbyl radical or an alkyl group or an alkenyl or alkynyl group which may contain 1 to 40 carbon atoms and in which individual hydrogen atoms or $CH_2$ groups may also be replaced by the abovementioned groups are preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more non-adjacent $CH_2$ groups may be replaced by the abovementioned groups; in addition, it is also possible for one or more hydrogen atoms to be replaced by D, F, Cl, Br, I, CN or $NO_2$, preferably F, Cl or CN, further preferably F or CN, especially preferably CN.

An aromatic or heteroaromatic ring system which has 5-60 aromatic ring atoms and may also be substituted in each case by the abovementioned $R^2$ radicals or a hydrocarbyl radical and which may be joined to the aromatic or heteroaromatic system via any desired positions is especially understood to mean groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, qui noxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or groups derived from combinations of these systems.

Adjacent X and Z groups in the context of this application are respectively understood to mean X and Z groups bonded directly to one another.

Adjacent radicals or adjacent substituents in the context of the present application are understood to mean substituents which are bonded to carbon atoms that are in turn bonded directly to one another, or substituents bonded to the same carbon, silicon, nitrogen, boron or phosphorus atom.

The wording that two or more radicals together may form a ring, in the context of the present application, shall be understood to mean, inter alia, that the two radicals are joined to one another by a chemical bond. This is illustrated by the following scheme:

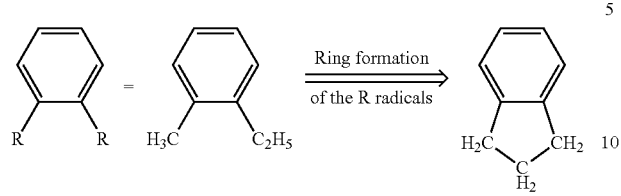

In addition, however, the abovementioned wording shall also be understood to mean that, if one of the two radicals is hydrogen, the second radical binds to the position to which the hydrogen atom was bonded, forming a ring.

The group of the formula (2) may be attached in various positions within the compound of the formula (1). Embodiments of the present invention are therefore the compounds of the following formulae (3) to (8):

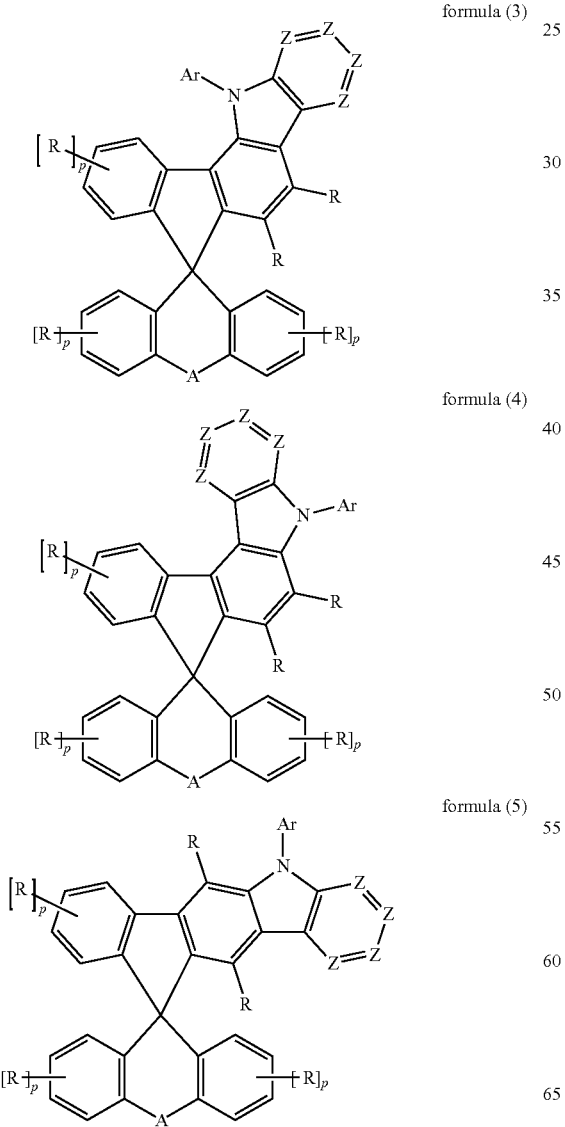

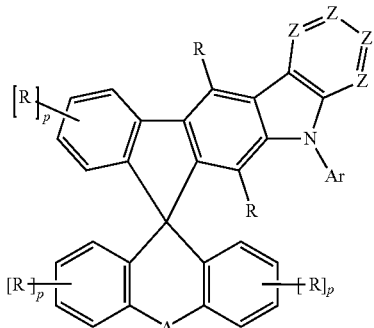

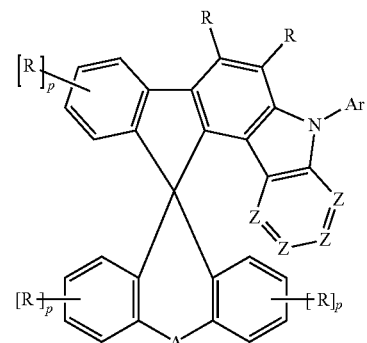

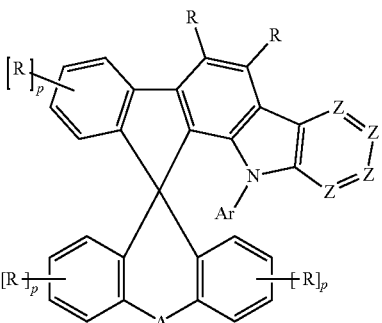

where the symbols and indices used have the definitions given above.

In a preferred embodiment of the formulae (1) to (8), p is the same or different at each instance and is 0, 1, 2 or 3, more preferably 0, 1 or 2, and most preferably 0 or 1.

Preferred embodiments of the structures of formula (3) to (8) are the structures of the formulae (3a) to (8a)

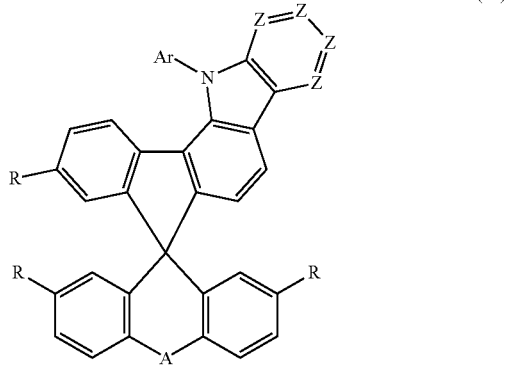

formula (4a)
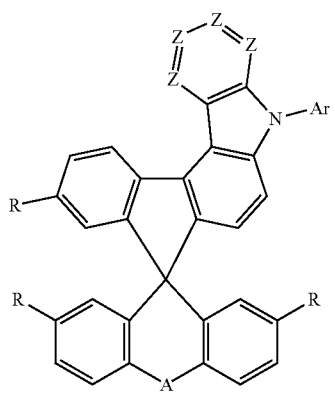
formula (5a)
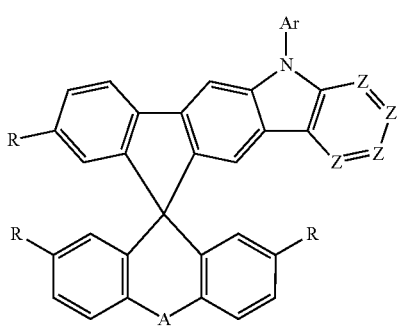
formula (6a)
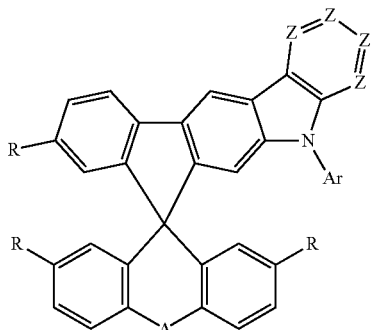
formula (7a)
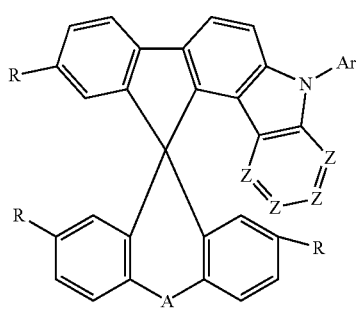
formula (8a)
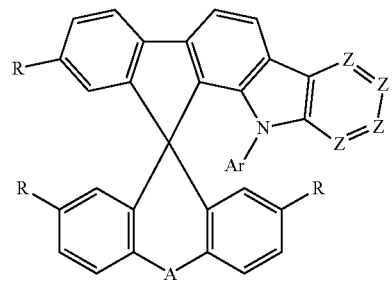
where the symbols used have the definitions given above.
In a preferred embodiment of the invention, Z is CR. Preferred embodiments of the present invention are therefore the compounds of the following formulae (3b) to (8b):
formula (3b)
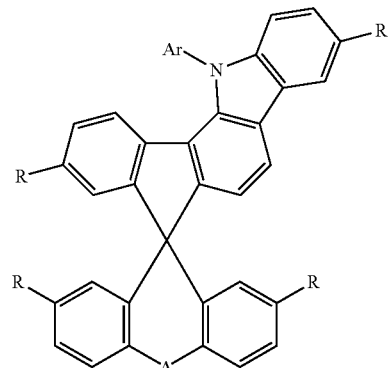
formula (4b)
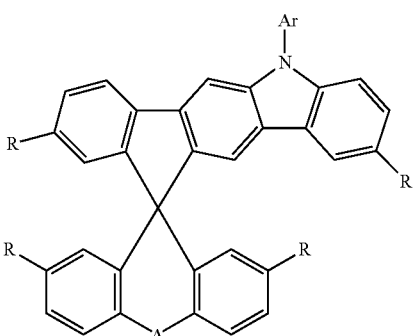
formula (5b)
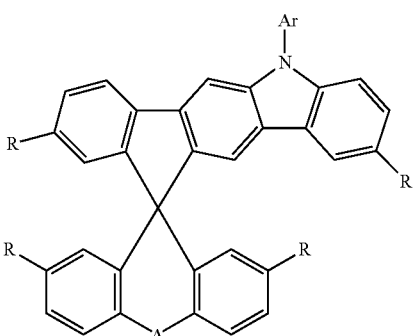

formula (6b)

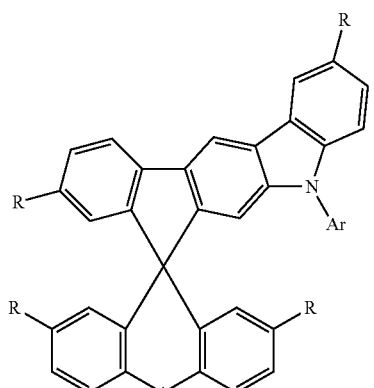

formula (7b)

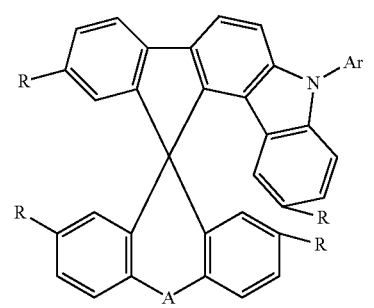

formula (8b)

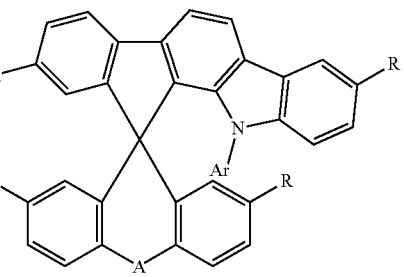

where the symbols used have the definitions given above.

In a further preferred embodiment of the invention, in the compounds of the formula (1), (3) to (8), (3a) to (8a) and (3b) to (8b), the symbol A is oxygen.

Particularly preferred embodiments of the present invention are the compounds of the following formulae (3c) to (8c):

formula (3c)

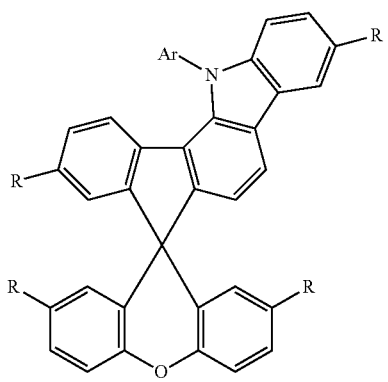

formula (4c)

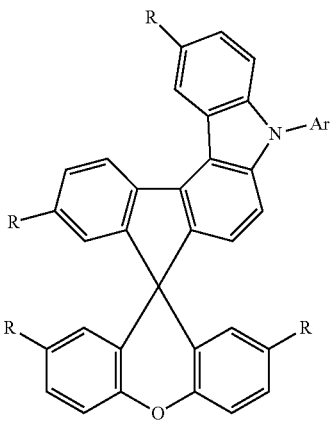

formula (5c)

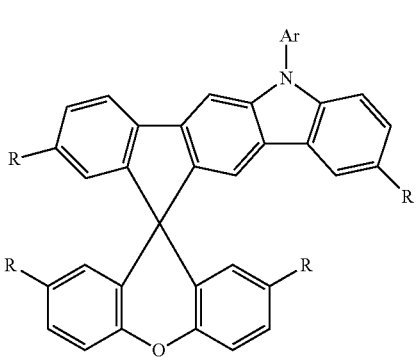

formula (6c)

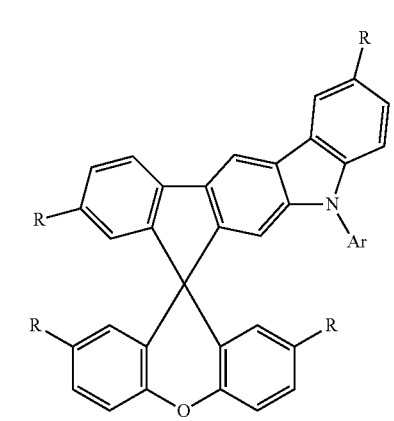

formula (7c)

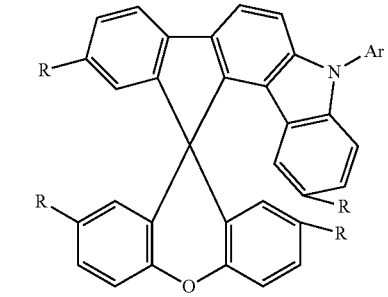

formula (8c)

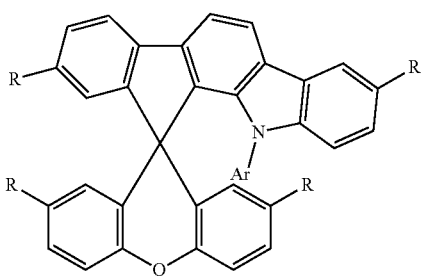

where the symbols used have the definitions given above.

Very particularly preferred embodiments of the present invention are the compounds of the following formulae (3d) to (8d):

formula (3d)

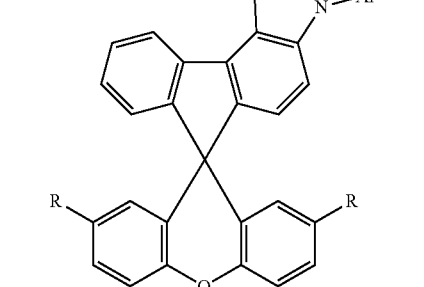

formula (4d)

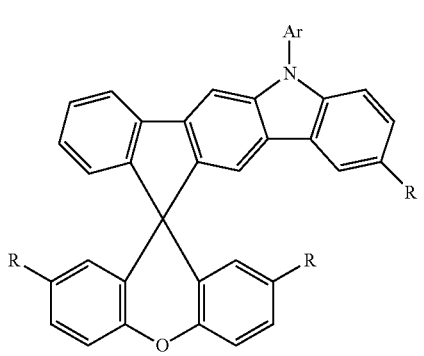

formula (5d)

formula (6d)

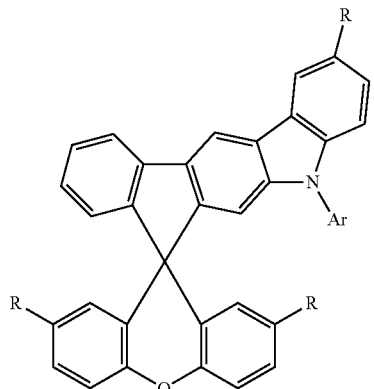

formula (7d)

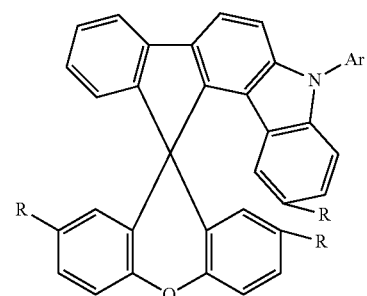

formula (8d)

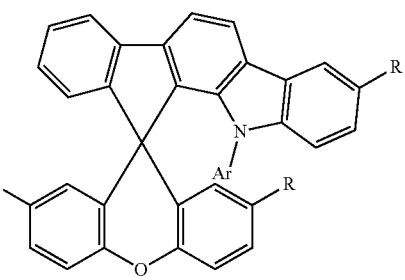

where the symbols used have the definitions given above.

In a preferred embodiment of the invention, Ar is an aromatic or heteroaromatic ring system having 5 to 24 aromatic ring atoms, preferably having 6 to 12 aromatic ring atoms, each of which may be substituted by one or more R radicals. Suitable Ar groups are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene, especially 2-bonded fluorene, spirobifluorene, especially 2- or 4-bonded spirobifluorene, naphthalene, especially 1- or 2-bonded naphthalene, indole, benzofuran, benzothiophene, carbazole, especially 2- or 3-bonded carbazole, dibenzofuran, especially 1-, 2-, 3- or 4-bonded dibenzofuran, dibenzothiophene, especially 1-, 2-, 3- or 4-bonded dibenzothiophene, indenocarbazole, indolocarbazole, pyridine, pyrimidine, pyrazine, pyridazine, triazine, phenanthrene, triphenylene or combinations of two or three of these groups, each of which may be substituted by one or more R radicals.

The Ar groups here are preferably selected from the groups of the following formulae Ar-1 to Ar-56:

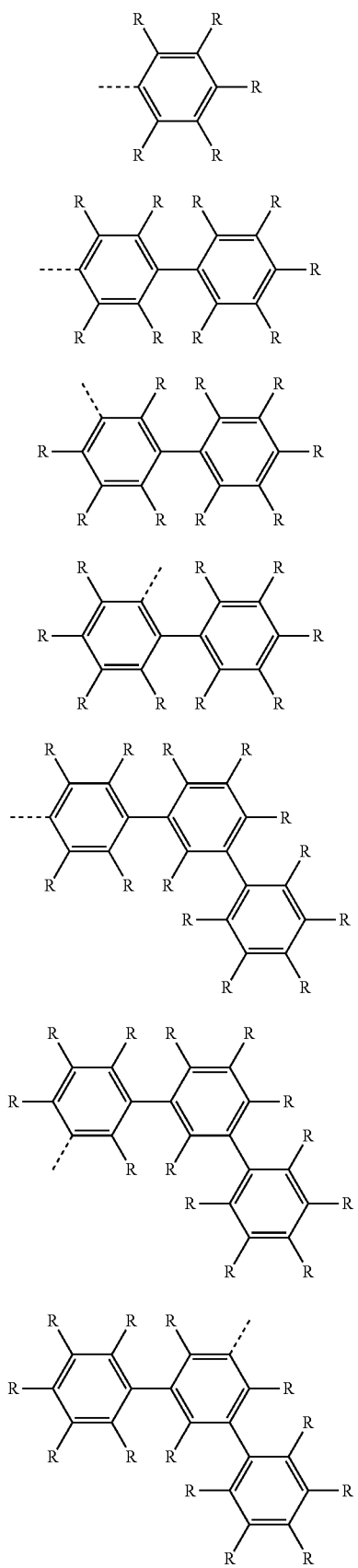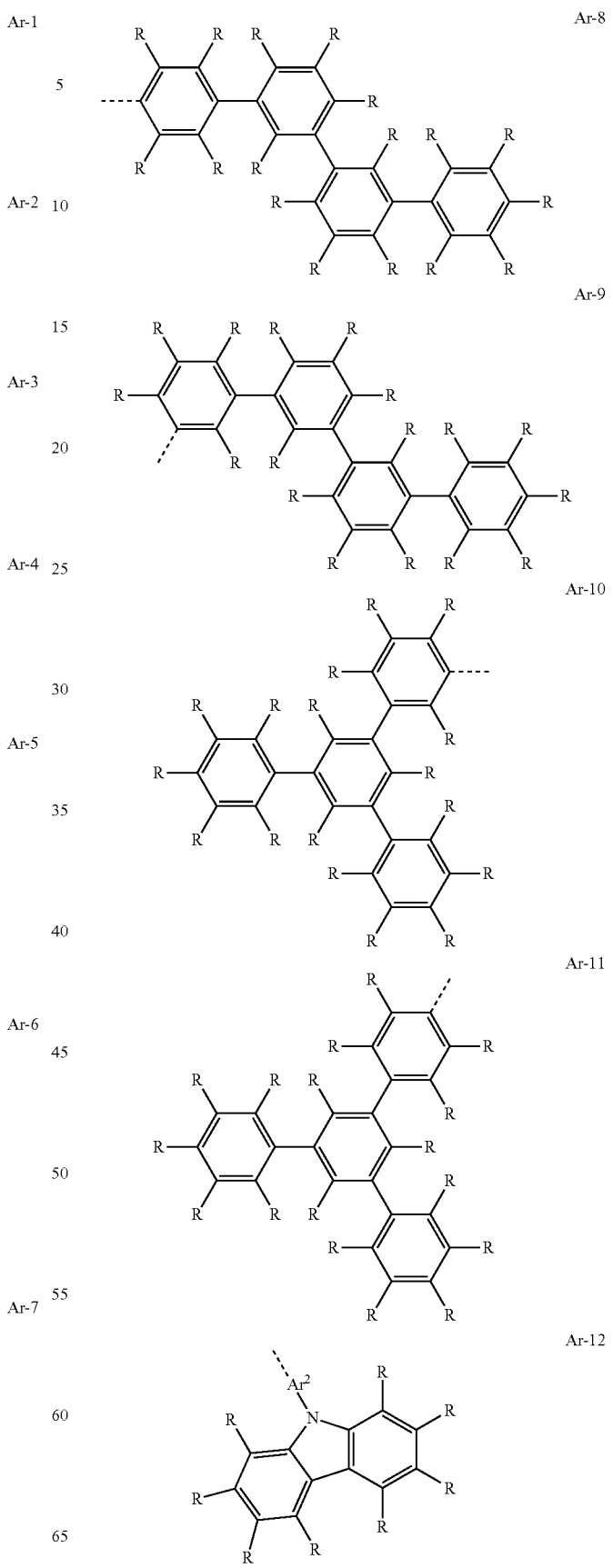

Ar-13
Ar-14
Ar-15
Ar-16
Ar-17
Ar-18
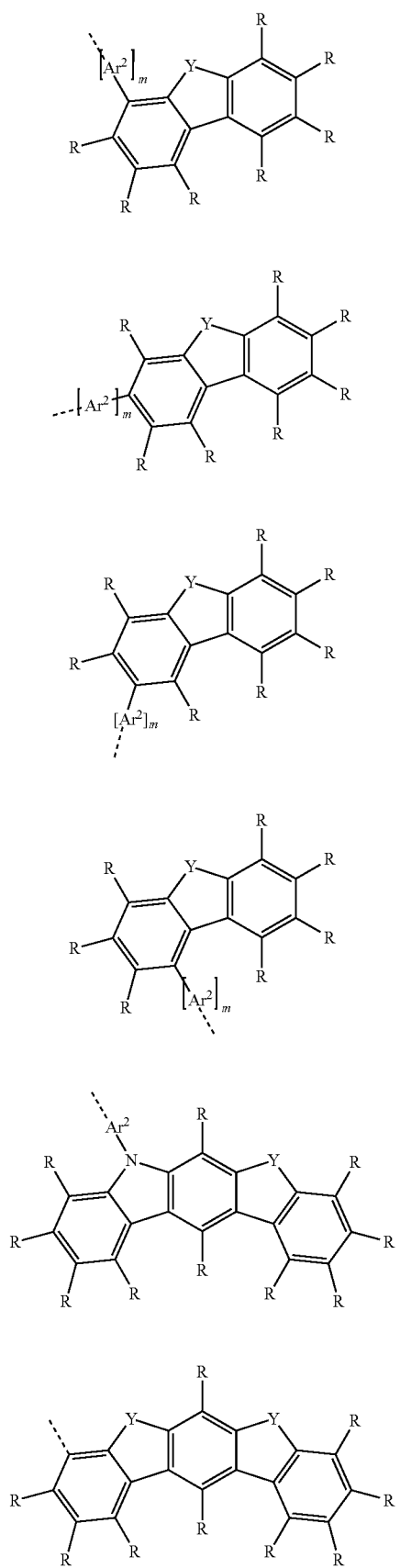
Ar-19
Ar-20
Ar-21
Ar-22
Ar-23
Ar-24
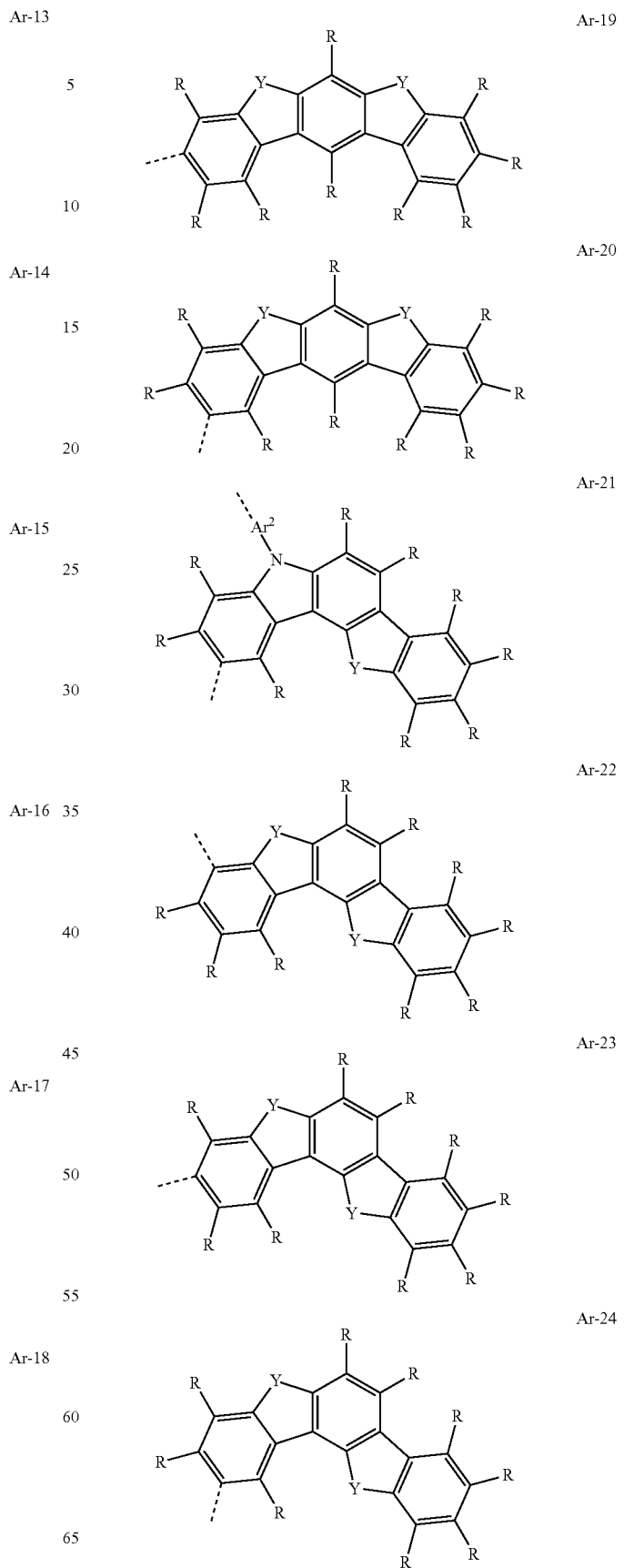

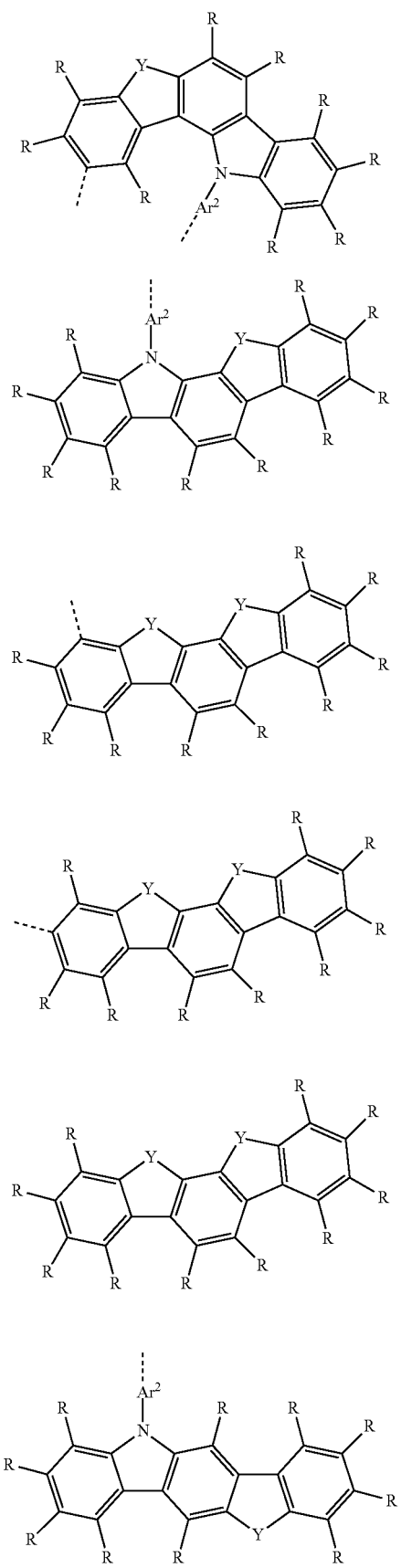
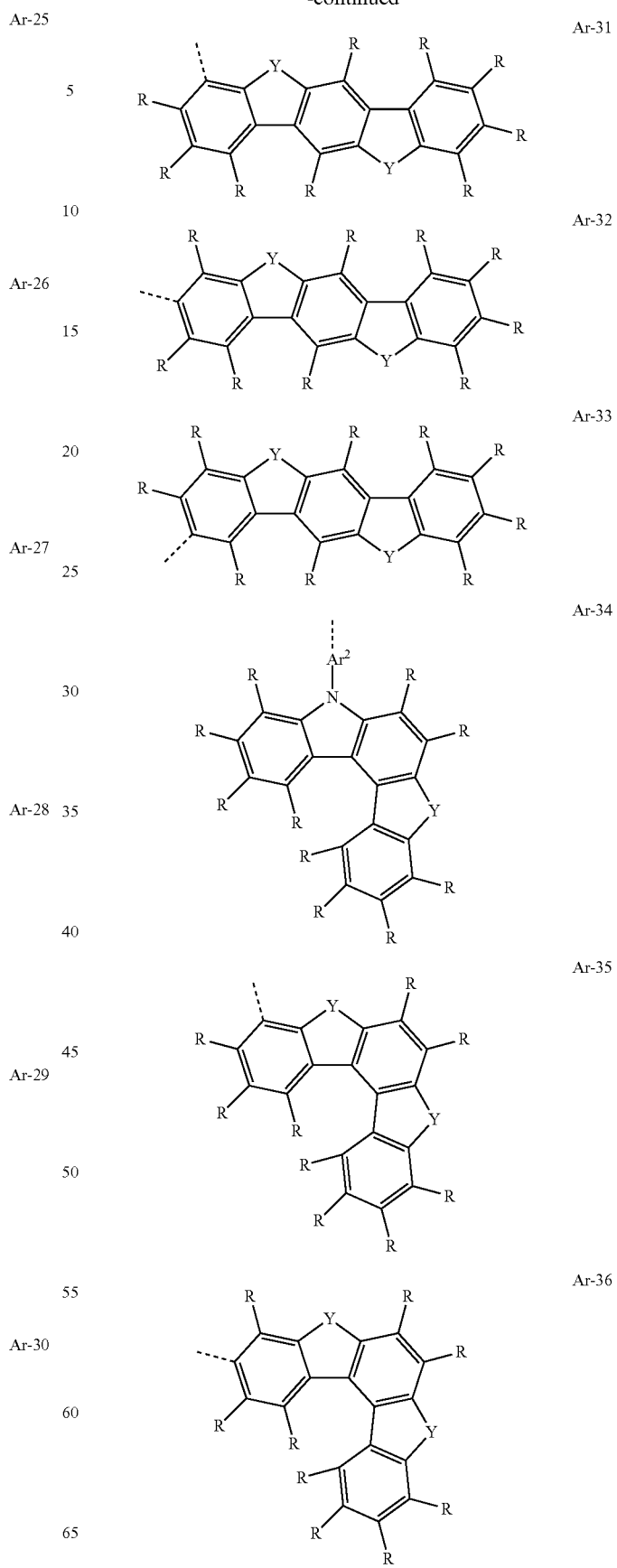

Ar-37
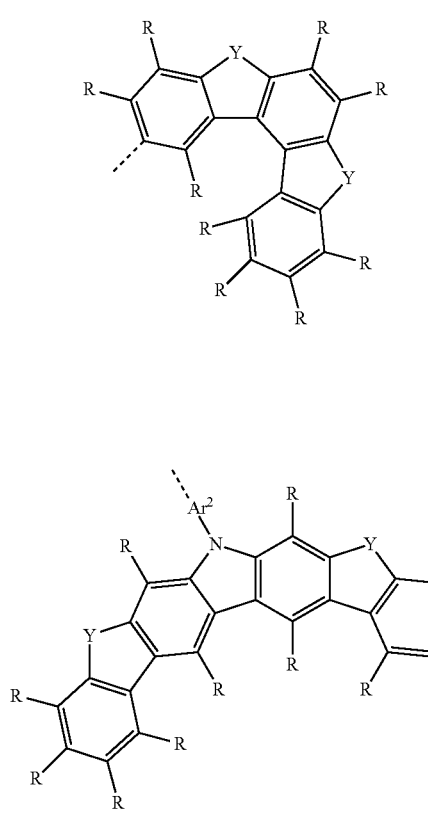
Ar-38
Ar-39
Ar-40
Ar-41
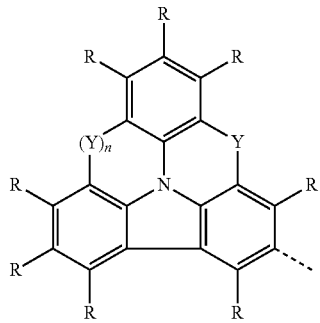
Ar-42
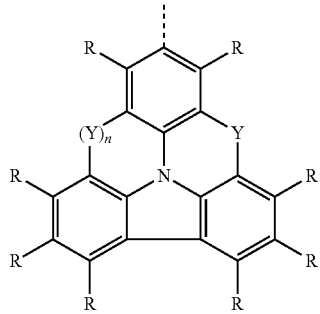
Ar-43
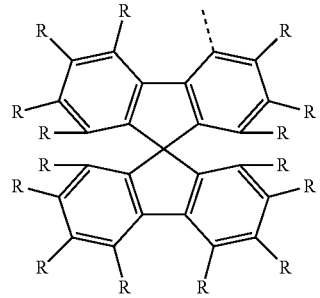
Ar-44
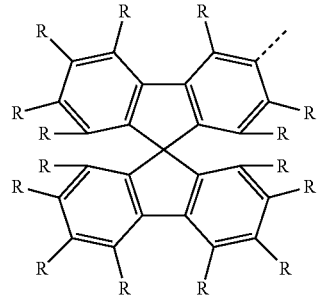
Ar-45
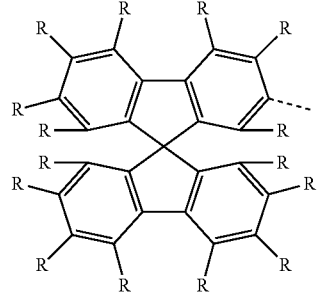

Ar-46 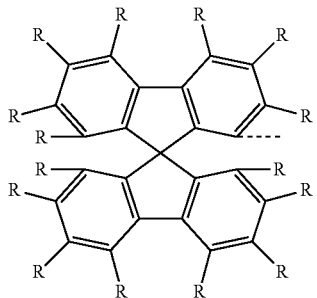

Ar-47 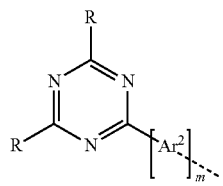

Ar-48 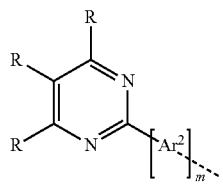

Ar-49 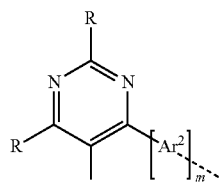

Ar-50 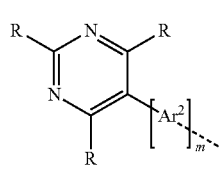

Ar-51 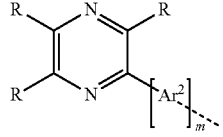

Ar-52 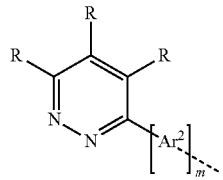

Ar-53 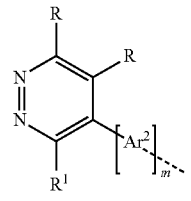

Ar-54 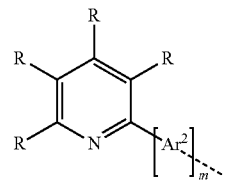

Ar-55 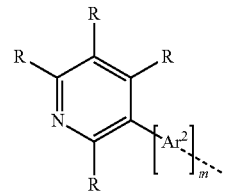

Ar-56 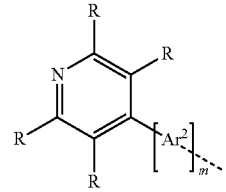

where R has the definitions given above, the dotted bond represents the bond to the nitrogen in formula (2) or in the preferred embodiments and, in addition:

$Ar^2$ is the same or different at each instance and is a bivalent aromatic or heteroaromatic ring system which has 6 to 18 aromatic ring atoms and may be substituted in each case by one or more R radicals;

Y is the same or different at each instance and is $CR_2$, NR, O or S;

n is 0 or 1, where n=0 means that no Y group is bonded at this position and R radicals are bonded to the corresponding carbon atoms instead;

m is 0 or 1, where m=0 means that the $Ar^2$ group is absent and that the corresponding aromatic or heteroaromatic group is bonded directly to the nitrogen in formula (2) or in the preferred embodiments.

When the abovementioned groups for Ar have two or more Y groups, possible options for these include all combinations from the definition of Y. Preferred embodiments in that case are those in which one Y group is NR and the other Y group is $CR_2$ or in which both Y groups are NR or in which both Y groups are O. In a particularly preferred embodiment of the invention, in Ar groups having a plurality of Y groups, at least one Y group is $CR_2$ or NR.

When Y is NR, the substituent R bonded to the nitrogen atom is preferably an aromatic or heteroaromatic ring system which has 5 to 24 aromatic ring atoms and may also be substituted by one or more $R^1$ radicals. In a particularly preferred embodiment, this R substituent is the same or different at each instance and is an aromatic or heteroaromatic ring system which has 6 to 24 aromatic ring atoms, which does not have any fused aryl groups and which does not have any fused heteroaryl groups in which two or more aromatic or heteroaromatic 6-membered ring groups are fused directly to one another, and which may also be substituted in each case by one or more $R^1$ radicals. Particular preference is given to phenyl, biphenyl, terphenyl and quaterphenyl having bonding patterns as listed above for Ar-1 to Ar-11, where these structures may be substituted by one or more $R^1$ radicals, but are preferably unsubstituted.

When Y is $CR_2$, the substituents R bonded to this carbon atom are preferably the same or different at each instance and are a linear alkyl group having 1 to 10 carbon atoms or a branched or cyclic alkyl group having 3 to 10 carbon atoms or an aromatic or heteroaromatic ring system having 5 to 24 aromatic ring atoms, which may also be substituted by one or more $R^1$ radicals. Most preferably, R is a methyl group or a phenyl group. In this case, the R radicals together may also form a ring system, which leads to a Spiro system.

In a further preferred embodiment of the invention, R on the base skeleton of the compounds of the formula (1) and in the preferred embodiments is the same or different at each instance and is selected from the group consisting of H, D, F, CN, $N(Ar^1)_2$, $C(=O)Ar^1$, $P(=O)(Ar^1)_2$, a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more $R^1$ radicals, where one or more nonadjacent $CH_2$ groups may be replaced by O and where one or more hydrogen atoms may be replaced by D or F, or an aromatic or heteroaromatic ring system which has 5 to 30 aromatic ring atoms and may be substituted in each case by one or more $R^1$ radicals. More preferably, R is the same or different at each instance and is selected from the group consisting of H, $N(Ar^1)_2$, a straight-chain alkyl group having 1 to 6 carbon atoms, especially having 1 to 4 carbon atoms, or a branched or cyclic alkyl group having 3 to 8 carbon atoms, especially having 3 to 6 carbon atoms, each of which may be substituted by one or more $R^1$ radicals, but is preferably unsubstituted, or an aromatic or heteroaromatic ring system which has 5 to 24 aromatic ring atoms and may be substituted in each case by one or more $R^1$ radicals. Most preferably, R is the same or different at each instance and is selected from the group consisting of H, $N(Ar^1)_2$ or an aromatic or heteroaromatic ring system which has 5 to 24 aromatic ring atoms and may be substituted in each case by one or more $R^1$ radicals.

When R is an aromatic or heteroaromatic ring system, this R radical is preferably the same or different at each instance and is selected from the same groups as specified above as suitable groups for Ar, especially from the Ar-1 to Ar-56 groups, except that $R^1$ substituents are bonded thereto in place of the R substituents.

Further suitable R groups are groups of the formula $—[Ar^5]_q—N(Ar^3)(Ar^4)$ where q is 0 or 1 and $Ar^3$, $Ar^4$ and $Ar^5$ are the same or different at each instance and are an aromatic or heteroaromatic ring system which has 5 to 24 aromatic ring atoms and may be substituted in each case by one or more $R^1$ radicals.

In this case, $Ar^5$ and $Ar^3$ when q=1 may also be bonded to one another and/or $Ar^3$ and $Ar^4$ to one another via a single bond or via a group selected from $C(R^1)_2$, $NR^1$, O or S, preferably via a single bond. Preferably, $Ar^5$ and $Ar^3$ are joined to one another and $Ar^3$ and $Ar^4$ to one another in the respective ortho positions to the bond to the nitrogen atom.

In one embodiment of the invention, q=1 and $Ar^5$ and $Ar^3$ are bonded to one another via a single bond. In a further embodiment of the invention, q=0 or 1 and $Ar^3$ and $Ar^4$ are bonded to one another via a single bond. In yet a further embodiment of the invention, q=0 or 1, and none of the $Ar^3$, $Ar^4$ and $Ar^5$ groups are bonded to one another.

Preferably, $Ar^5$ is an aromatic or heteroaromatic ring system which has 6 to 24 aromatic ring atoms, preferably 6 to 12 aromatic ring atoms, and may be substituted in each case by one or more $R^1$ radicals. More preferably, $Ar^5$ is selected from the group consisting of ortho-, meta- or para-phenylene or ortho-, meta- or para-biphenyl, each of which may be substituted by one or more $R^1$ radicals, but are preferably unsubstituted. Most preferably, $Ar^5$ is an unsubstituted phenylene group. This is especially true when $Ar^5$ is bonded to $Ar^3$ via a single bond.

Preferably, $Ar^3$ and $Ar^4$ are the same or different at each instance and are an aromatic or heteroaromatic ring system which has 6 to 24 aromatic ring atoms, each of which may be substituted by one or more $R^1$ radicals. Particularly preferred $Ar^3$ and $Ar^4$ groups are the same or different at each instance and are selected from the group consisting of benzene, ortho-, meta- or para-biphenyl, ortho-, meta- or para-terphenyl or branched terphenyl, ortho-, meta- or para-quaterphenyl or branched quaterphenyl, 1-, 2-, 3- or 4-fluorenyl, 1-, 2-, 3- or 4-spirobifluorenyl, 1- or 2-naphthyl, indole, benzofuran, benzothiophene, 1-, 2-, 3- or 4-carbazole, 1-, 2-, 3- or 4-dibenzofuran, 1-, 2-, 3- or 4-dibenzothiophene, indenocarbazole, indolocarbazole, 2-, 3- or 4-pyridine, 2-, 4- or 5-pyrimidine, pyrazine, pyridazine, triazine, phenanthrene, triphenylene or combinations of two, three or four of these groups, each of which may be substituted by one or more $R^1$ radicals. More preferably, $Ar^3$ and $Ar^4$ are the same or different at each instance and are an aromatic ring system which has 6 to 24 aromatic ring atoms and may be substituted by one or more $R^1$ radicals, especially selected from the group consisting of benzene, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene, especially 1-, 2-, 3- or 4-fluorene, or spirobifluorene, especially 1-, 2-, 3- or 4-spirobifluorene.

Particularly preferred groups of the formula $—[Ar^5]_q—N(Ar^3)(Ar^4)$ are those in which q=1 and $Ar^5$ is a phenyl group bonded to $Ar^3$ via a single bond. This gives rise to a carbazole or a carbazole derivative.

In a further preferred embodiment of the invention, the compounds of the formula (1) or the preferred embodiments are bipolar compounds, i.e. compounds containing both electron-transporting and hole-transporting units. It is preferable here when the Ar group is an electron-transporting unit, for example a unit of one of the abovementioned formulae Ar-47 to Ar-56, and when at least one R radical, especially an R radical in the unit of the formula (2), is a hole-transporting unit, especially a unit of the abovementioned formula $—[Ar^5]_q—N(Ar^3)(Ar^4)$.

At the same time, in compounds which are processed by vacuum evaporation, the alkyl groups preferably have not more than five carbon atoms, more preferably not more than 4 carbon atoms, most preferably not more than 1 carbon atom. For compounds which are processed from solution, suitable compounds are also those substituted by alkyl groups, especially branched alkyl groups, having up to 10 carbon atoms or those substituted by oligoarylene groups, for example ortho-, meta-, para- or branched terphenyl or quaterphenyl groups.

When the compounds of the formula (1) or the preferred embodiments are used as matrix material for a phosphorescent emitter or in a layer directly adjoining a phosphorescent layer, it is further preferable when the compound does not contain any fused aryl or heteroaryl groups in which more than two six-membered rings are fused directly to one another. It is especially preferable that the R, $R^1$ and $Ar^1$ to $Ar^5$ radicals do not contain any fused aryl or heteroaryl groups in which two or more six-membered rings are fused directly to one another.

The abovementioned preferred embodiments may be combined with one another as desired. In a particularly preferred embodiment of the invention, the abovementioned preferences occur simultaneously.

Examples of preferred compounds according to the embodiments detailed above are the compounds detailed in the following table:

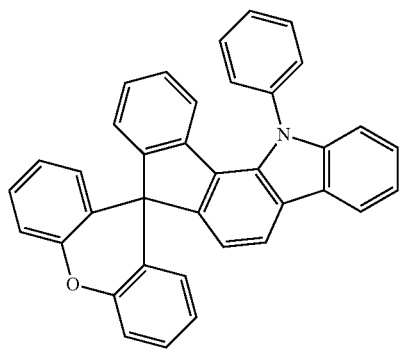 [SMILES: c1ccc(-n2c3ccccc3c3ccc4c(c32)-c2ccccc2C42c3ccccc3Oc3ccccc32)cc1]
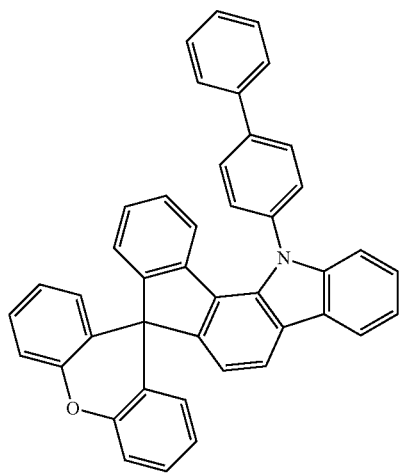 [SMILES: c1ccc(-c2ccc(-n3c4ccccc4c4ccc5c(c43)-c3ccccc3C53c4ccccc4Oc4ccccc43)cc2)cc1]
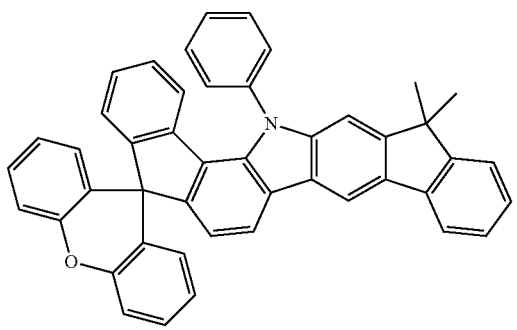 [SMILES: CC1(C)c2ccccc2-c2cc3c4ccc5c(c4n(-c4ccccc4)c3cc21)-c1ccccc1C51c2ccccc2Oc2ccccc21]
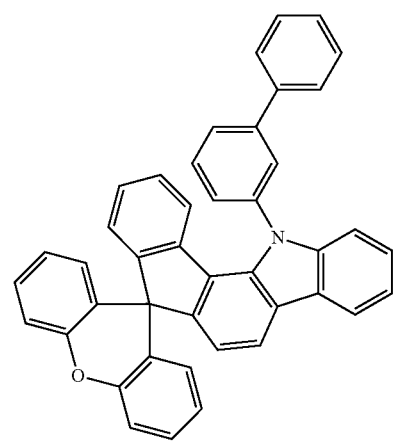 [SMILES: c1ccc(-c2cccc(-n3c4ccccc4c4ccc5c(c43)-c3ccccc3C53c4ccccc4Oc4ccccc43)c2)cc1]

-continued
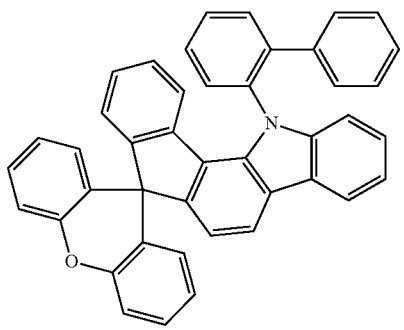 [SMILES: c1ccc(-c2ccccc2-n2c3ccccc3c3ccc4c(c32)-c2ccccc2C42c3ccccc3Oc3ccccc32)cc1]
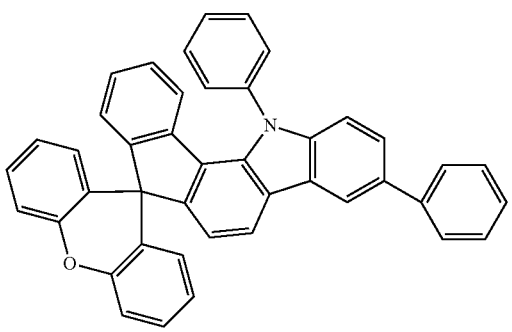 [SMILES: c1ccc(-c2ccc3c(c2)c2ccc4c(c2n3-c2ccccc2)-c2ccccc2C42c3ccccc3Oc3ccccc32)cc1]
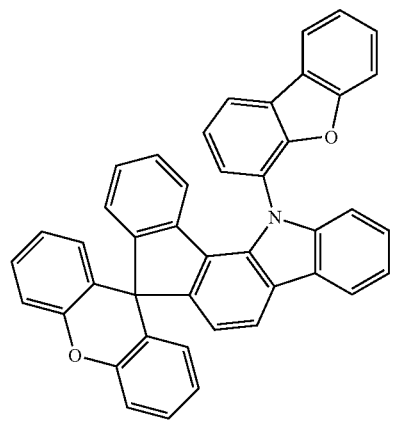 [SMILES: c1ccc2c(c1)Oc1ccccc1C21c2ccccc2-c2c1ccc1c3ccccc3n(-c3cccc4c3oc3ccccc34)c21]
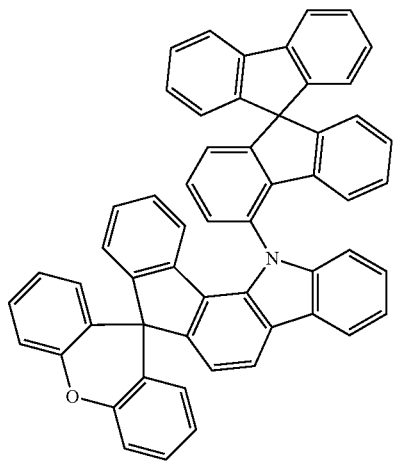 [SMILES: c1ccc2c(c1)Oc1ccccc1C21c2ccccc2-c2c1ccc1c3ccccc3n(-c3cccc4c3-c3ccccc3C43c4ccccc4-c4ccccc43)c21]

-continued
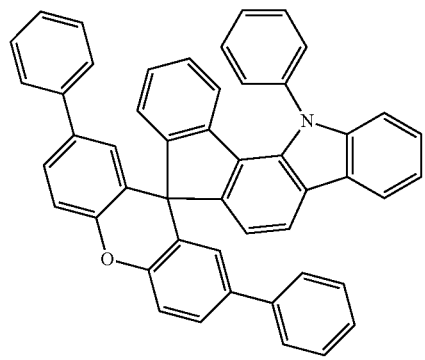 [SMILES: c1ccc(-c2ccc3c(c2)C2(c4cc(-c5ccccc5)ccc4O3)c3ccccc3-c3c2ccc2c4ccccc4n(-c4ccccc4)c32)cc1]
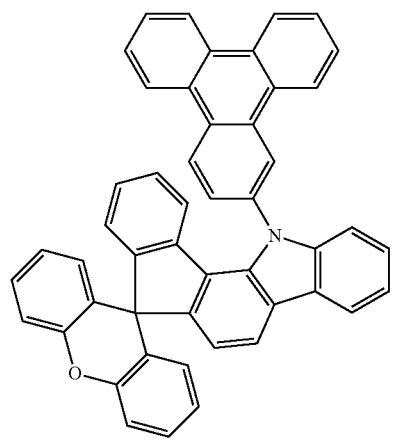 [SMILES: c1ccc2c(c1)Oc1ccccc1C21c2ccccc2-c2c1ccc1c3ccccc3n(-c3ccc4c5ccccc5c5ccccc5c4c3)c21]
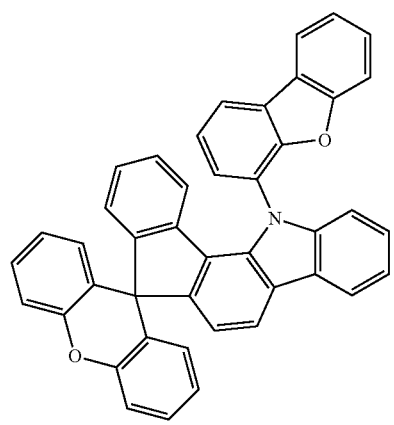 [SMILES: c1ccc2c(c1)Oc1ccccc1C21c2ccccc2-c2c1ccc1c3ccccc3n(-c3cccc4c3oc3ccccc34)c21]

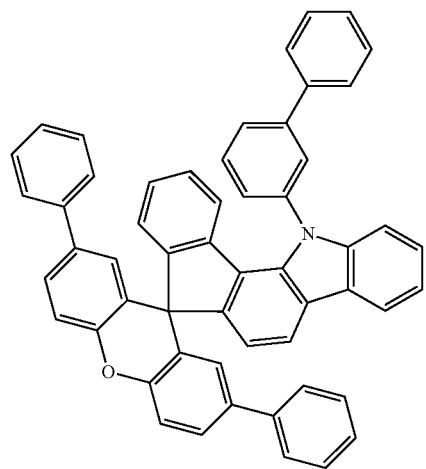 [SMILES: c1ccc(-c2cccc(-n3c4ccccc4c4ccc5c(c43)-c3ccccc3C53c4cc(-c5ccccc5)ccc4Oc4ccc(-c5ccccc5)cc43)c2)cc1]
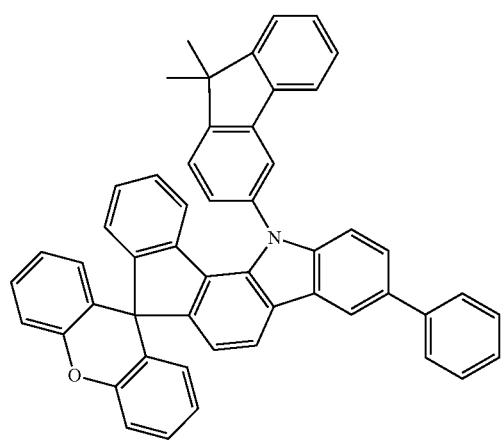 [SMILES: CC1(C)c2ccccc2-c2cc(-n3c4ccc(-c5ccccc5)cc4c4ccc5c(c43)-c3ccccc3C53c4ccccc4Oc4ccccc43)ccc21]
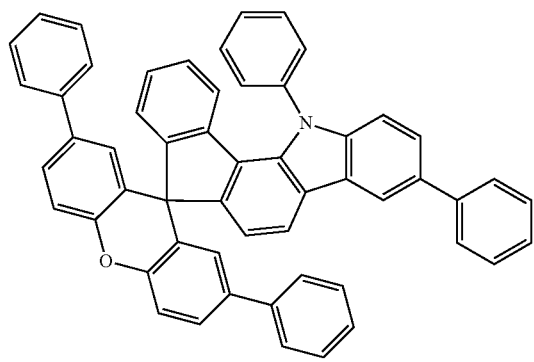 [SMILES: c1ccc(-c2ccc3c(c2)C2(c4cc(-c5ccccc5)ccc4O3)c3ccccc3-c3c2ccc2c4cc(-c5ccccc5)ccc4n(-c4ccccc4)c32)cc1]

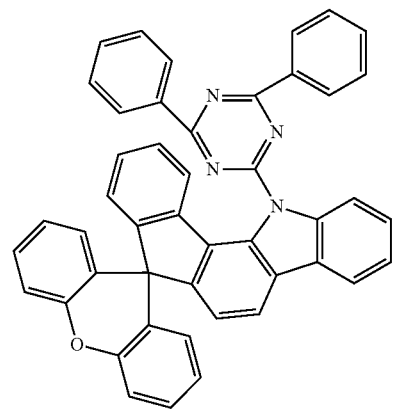
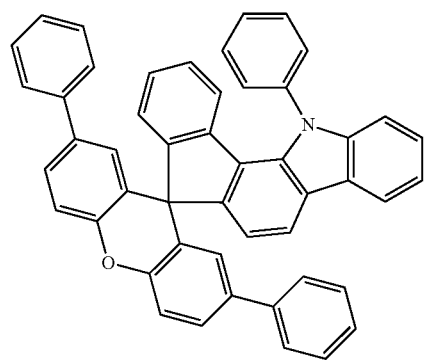 [SMILES: c1ccc(-c2ccc3c(c2)C2(c4cc(-c5ccccc5)ccc4O3)c3ccccc3-c3c2ccc2c4ccccc4n(-c4ccccc4)c32)cc1]
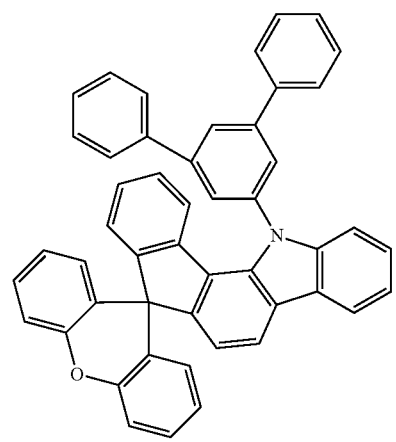 [SMILES: c1ccc(-c2cc(-c3ccccc3)cc(-n3c4ccccc4c4ccc5c(c43)-c3ccccc3C53c4ccccc4Oc4ccccc43)c2)cc1]

-continued
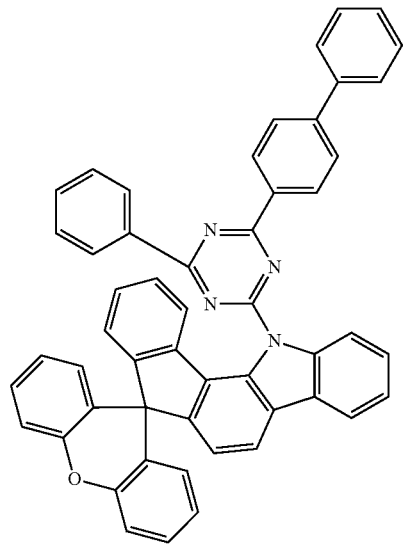 [SMILES: c1ccc(-c2ccc(-c3nc(-c4ccccc4)nc(-n4c5ccccc5c5ccc6c(c54)-c4ccccc4C64c5ccccc5Oc5ccccc54)n3)cc2)cc1]
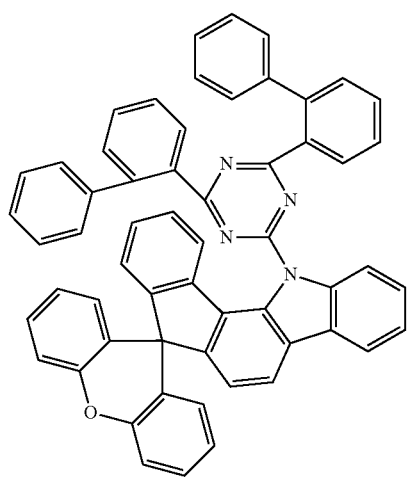 [SMILES: c1ccc(-c2ccccc2-c2nc(-c3ccccc3-c3ccccc3)nc(-n3c4ccccc4c4ccc5c(c43)-c3ccccc3C53c4ccccc4Oc4ccccc43)n2)cc1]
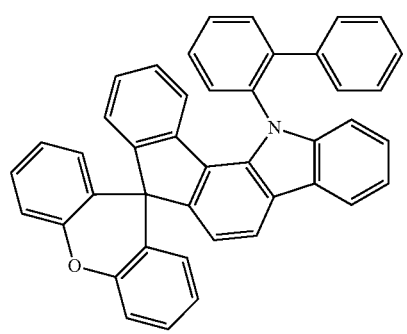 [SMILES: c1ccc(-c2ccccc2-n2c3ccccc3c3ccc4c(c32)-c2ccccc2C42c3ccccc3Oc3ccccc32)cc1]

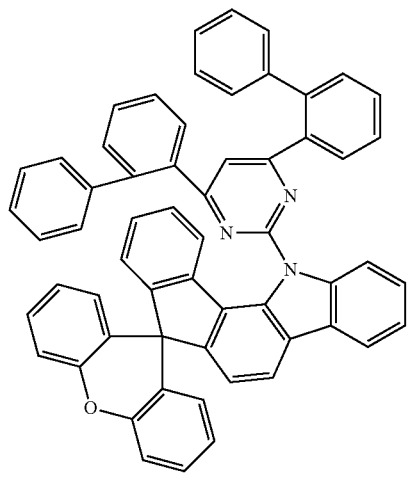 [SMILES: c1ccc(-c2ccccc2-c2cc(-c3ccccc3-c3ccccc3)nc(-n3c4ccccc4c4ccc5c(c43)-c3ccccc3C53c4ccccc4Oc4ccccc43)n2)cc1]
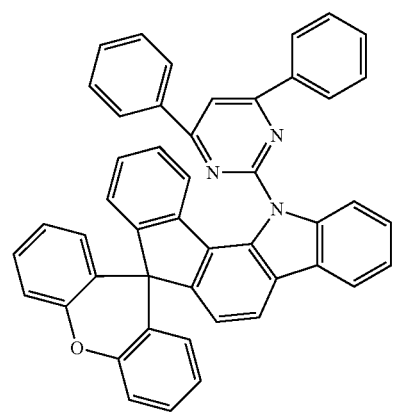 [SMILES: c1ccc(-c2cc(-c3ccccc3)nc(-n3c4ccccc4c4ccc5c(c43)-c3ccccc3C53c4ccccc4Oc4ccccc43)n2)cc1]
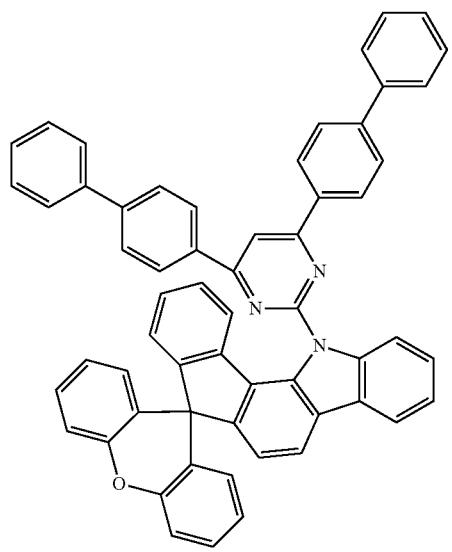 [SMILES: c1ccc(-c2ccc(-c3cc(-c4ccc(-c5ccccc5)cc4)nc(-n4c5ccccc5c5ccc6c(c54)-c4ccccc4C64c5ccccc5Oc5ccccc54)n3)cc2)cc1]

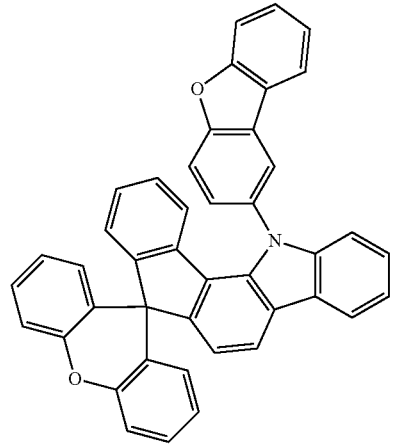 [SMILES: c1ccc2c(c1)Oc1ccccc1C21c2ccccc2-c2c1ccc1c3ccccc3n(-c3ccc4oc5ccccc5c4c3)c21]
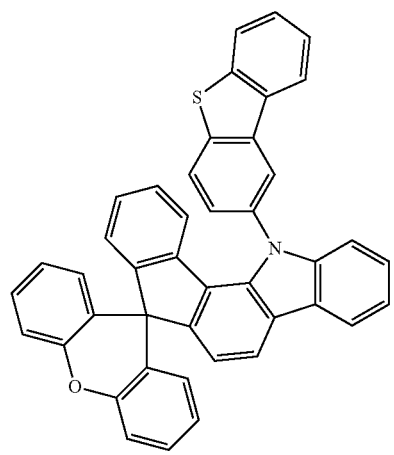 [SMILES: c1ccc2c(c1)Oc1ccccc1C21c2ccccc2-c2c1ccc1c3ccccc3n(-c3ccc4sc5ccccc5c4c3)c21]
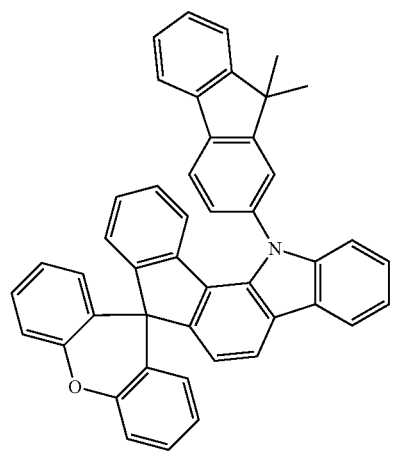 [SMILES: CC1(C)c2ccccc2-c2ccc(-n3c4ccccc4c4ccc5c(c43)-c3ccccc3C53c4ccccc4Oc4ccccc43)cc21]

-continued
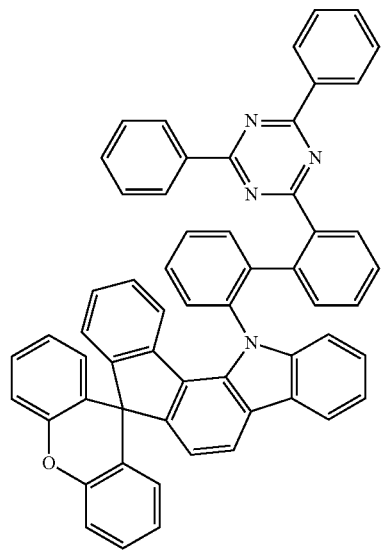 [SMILES: c1ccc(-c2nc(-c3ccccc3)nc(-c3ccccc3-c3ccccc3-n3c4ccccc4c4ccc5c(c43)-c3ccccc3C53c4ccccc4Oc4ccccc43)n2)cc1]
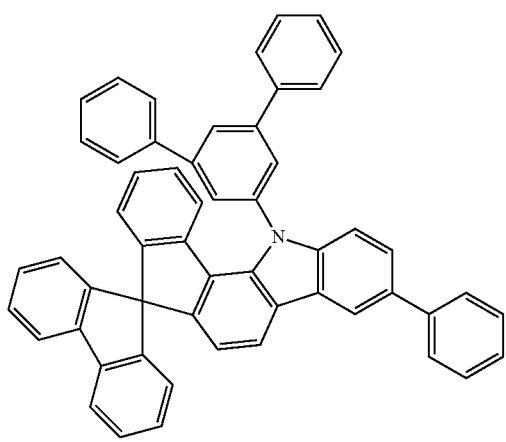 [SMILES: c1ccc(-c2cc(-c3ccccc3)cc(-n3c4ccc(-c5ccccc5)cc4c4ccc5c(c43)-c3ccccc3C53c4ccccc4-c4ccccc43)c2)cc1]
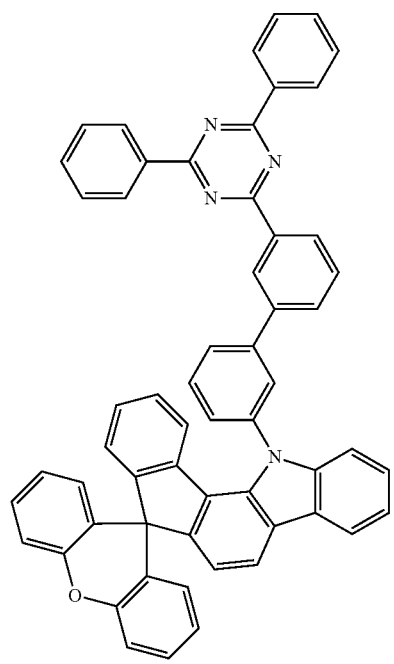 [SMILES: c1ccc(-c2nc(-c3ccccc3)nc(-c3cccc(-c4cccc(-n5c6ccccc6c6ccc7c(c65)-c5ccccc5C75c6ccccc6Oc6ccccc65)c4)c3)n2)cc1]

-continued
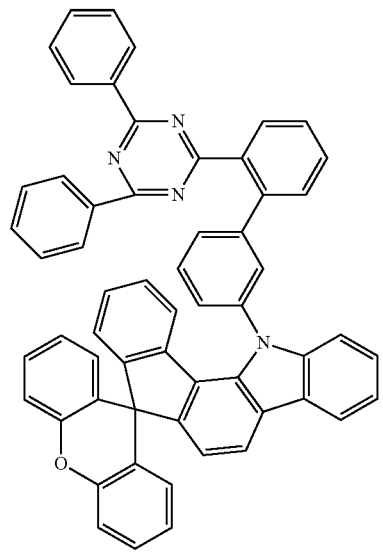 [SMILES: c1ccc(-c2nc(-c3ccccc3)nc(-c3ccccc3-c3cccc(-n4c5ccccc5c5ccc6c(c54)-c4ccccc4C64c5ccccc5Oc5ccccc54)c3)n2)cc1]
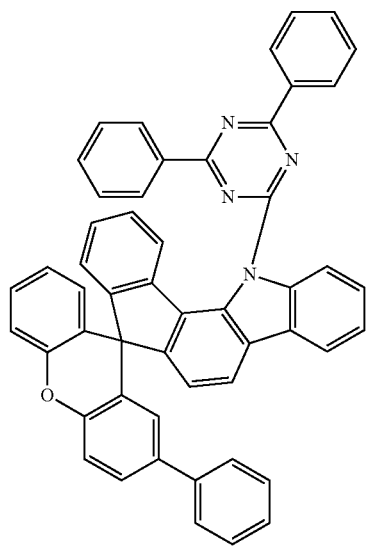 [SMILES: c1ccc(-c2ccc3c(c2)C2(c4ccccc4O3)c3ccccc3-c3c2ccc2c4ccccc4n(-c4nc(-c5ccccc5)nc(-c5ccccc5)n4)c32)cc1]
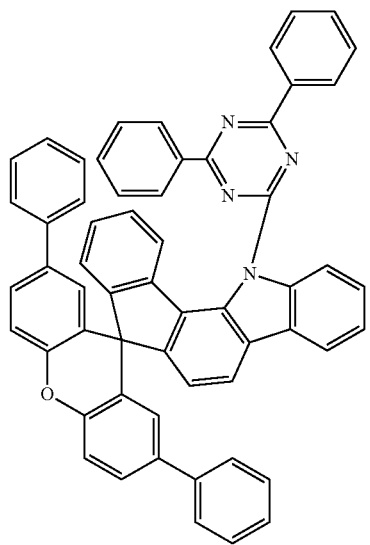 [SMILES: c1ccc(-c2ccc3c(c2)C2(c4cc(-c5ccccc5)ccc4O3)c3ccccc3-c3c2ccc2c4ccccc4n(-c4nc(-c5ccccc5)nc(-c5ccccc5)n4)c32)cc1]

-continued
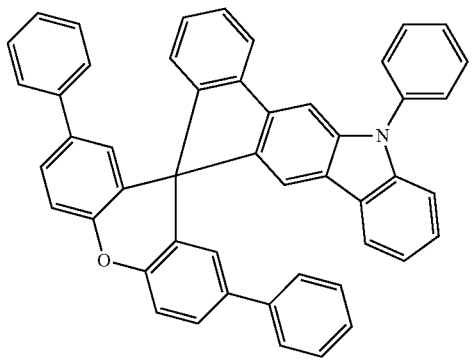 [SMILES: c1ccc(-c2ccc3c(c2)C2(c4cc(-c5ccccc5)ccc4O3)c3ccccc3-c3cc4c(cc32)c2ccccc2n4-c2ccccc2)cc1]
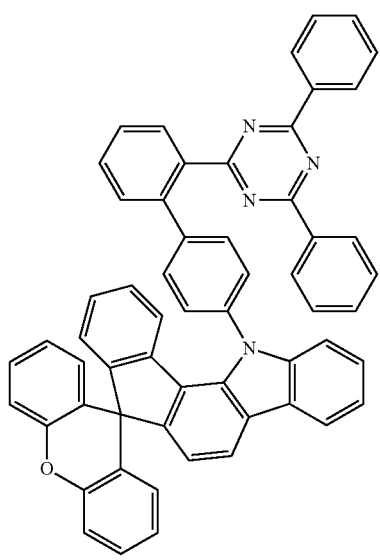 [SMILES: c1ccc(-c2nc(-c3ccccc3)nc(-c3ccccc3-c3ccc(-n4c5ccccc5c5ccc6c(c54)-c4ccccc4C64c5ccccc5Oc5ccccc54)cc3)n2)cc1]
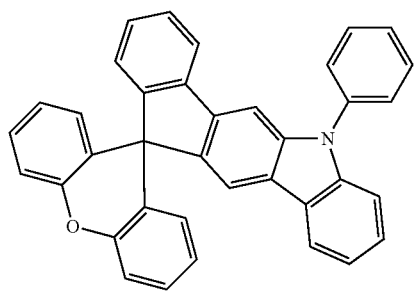 [SMILES: c1ccc(-n2c3ccccc3c3cc4c(cc32)-c2ccccc2C42c3ccccc3Oc3ccccc32)cc1]
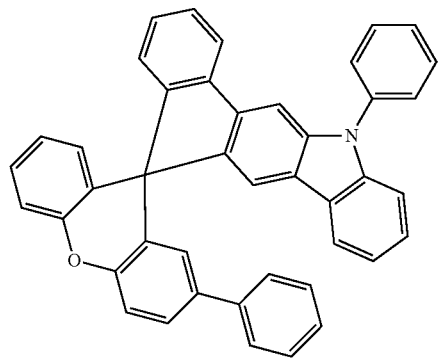 [SMILES: c1ccc(-c2ccc3c(c2)C2(c4ccccc4O3)c3ccccc3-c3cc4c(cc32)c2ccccc2n4-c2ccccc2)cc1]

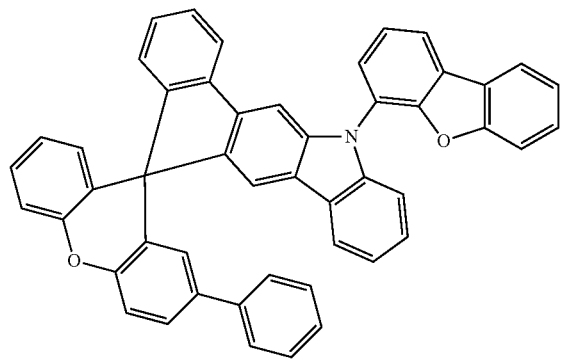 [SMILES: c1ccc(-c2ccc3c(c2)C2(c4ccccc4O3)c3ccccc3-c3cc4c(cc32)c2ccccc2n4-c2cccc3c2oc2ccccc23)cc1]
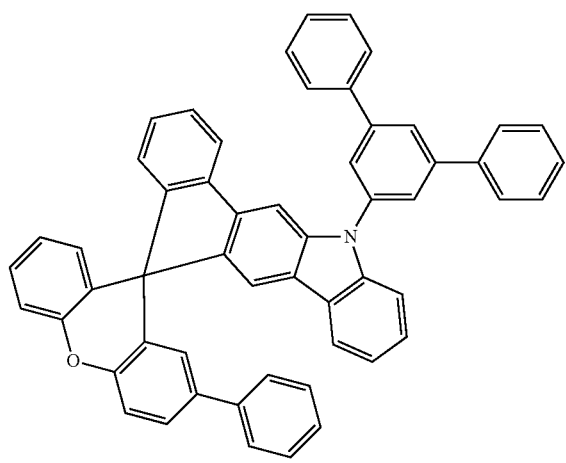 [SMILES: c1ccc(-c2cc(-c3ccccc3)cc(-n3c4ccccc4c4cc5c(cc43)-c3ccccc3C53c4ccccc4Oc4ccc(-c5ccccc5)cc43)c2)cc1]
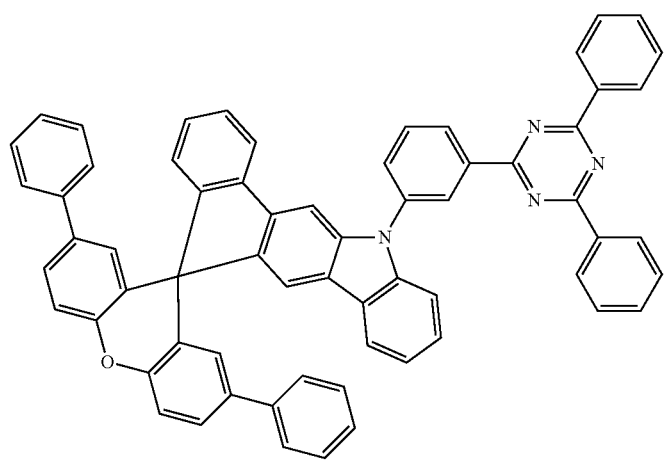 [SMILES: c1ccc(-c2ccc3c(c2)C2(c4cc(-c5ccccc5)ccc4O3)c3ccccc3-c3cc4c(cc32)c2ccccc2n4-c2cccc(-c3nc(-c4ccccc4)nc(-c4ccccc4)n3)c2)cc1]

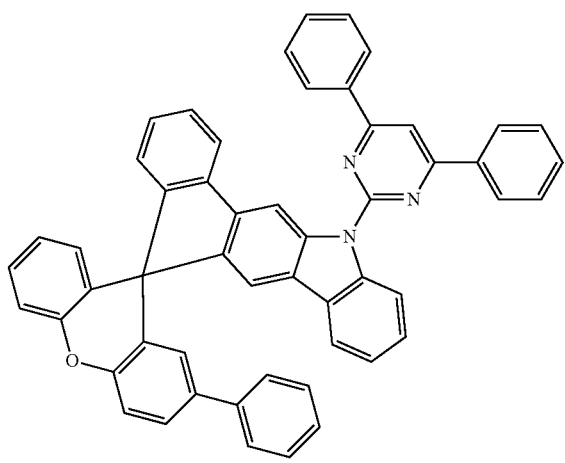 [SMILES: c1ccc(-c2ccc3c(c2)C2(c4ccccc4O3)c3ccccc3-c3cc4c(cc32)c2ccccc2n4-c2nc(-c3ccccc3)cc(-c3ccccc3)n2)cc1]
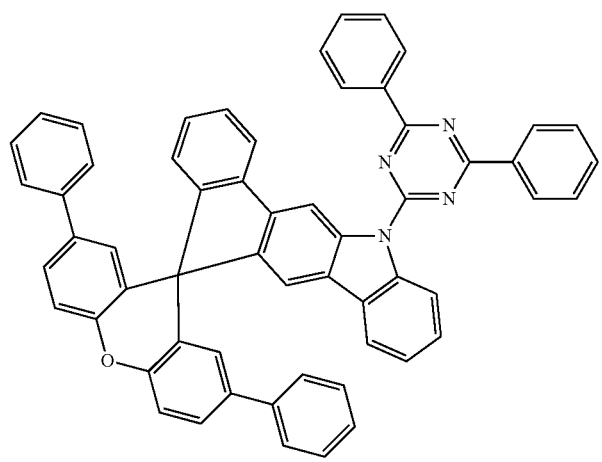 [SMILES: c1ccc(-c2ccc3c(c2)C2(c4cc(-c5ccccc5)ccc4O3)c3ccccc3-c3cc4c(cc32)c2ccccc2n4-c2nc(-c3ccccc3)nc(-c3ccccc3)n2)cc1]
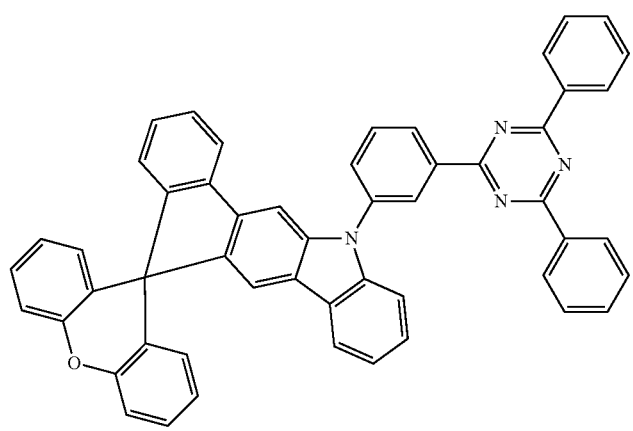 [SMILES: c1ccc(-c2nc(-c3ccccc3)nc(-c3cccc(-n4c5ccccc5c5cc6c(cc54)-c4ccccc4C64c5ccccc5Oc5ccccc54)c3)n2)cc1]

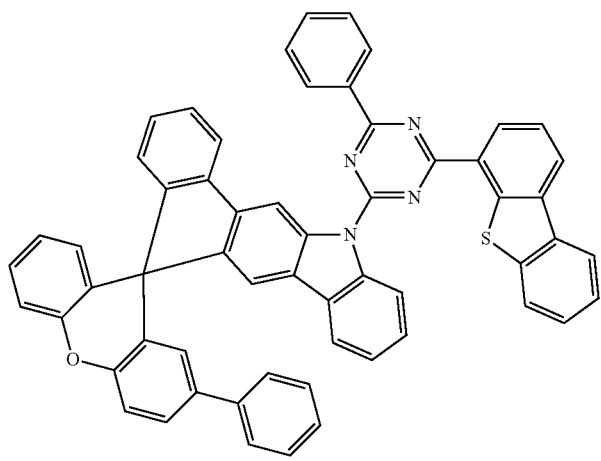 [SMILES: c1ccc(-c2ccc3c(c2)C2(c4ccccc4O3)c3ccccc3-c3cc4c(cc32)c2ccccc2n4-c2nc(-c3ccccc3)nc(-c3cccc4c3sc3ccccc34)n2)cc1]
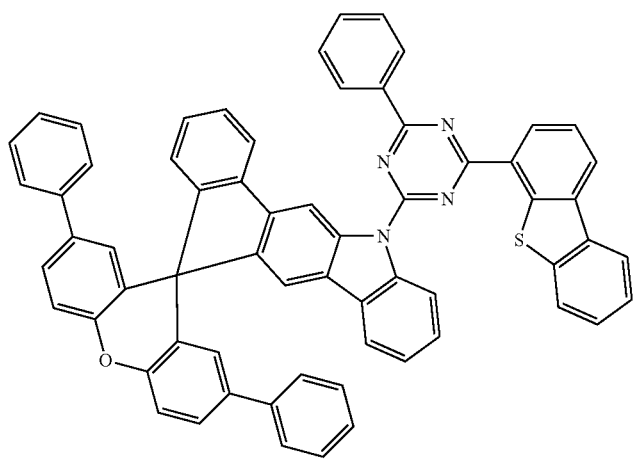 [SMILES: c1ccc(-c2ccc3c(c2)C2(c4cc(-c5ccccc5)ccc4O3)c3ccccc3-c3cc4c(cc32)c2ccccc2n4-c2nc(-c3ccccc3)nc(-c3cccc4c3sc3ccccc34)n2)cc1]
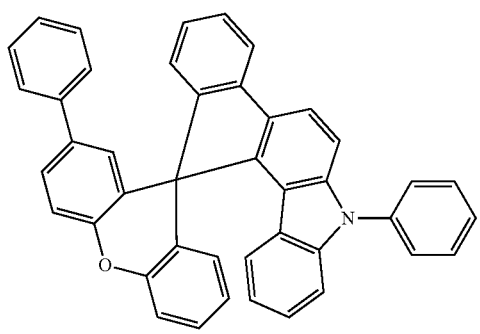 [SMILES: c1ccc(-c2ccc3c(c2)C2(c4ccccc4O3)c3ccccc3-c3ccc4c(c32)c2ccccc2n4-c2ccccc2)cc1]

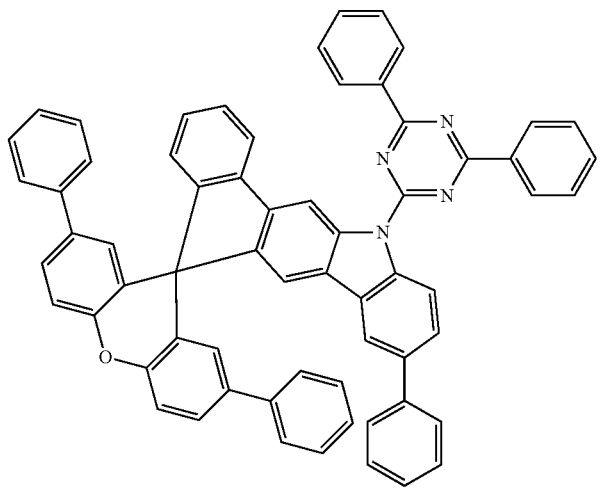 [SMILES: c1ccc(-c2ccc3c(c2)C2(c4cc(-c5ccccc5)ccc4O3)c3ccccc3-c3cc4c(cc32)c2cc(-c3ccccc3)ccc2n4-c2nc(-c3ccccc3)nc(-c3ccccc3)n2)cc1]
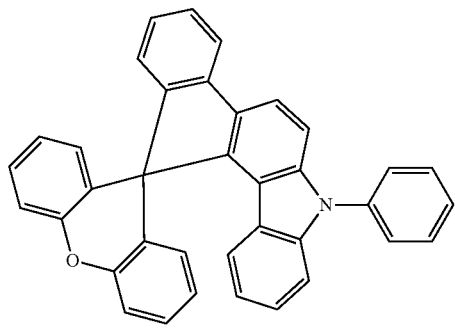 [SMILES: c1ccc(-n2c3ccccc3c3c4c(ccc32)-c2ccccc2C42c3ccccc3Oc3ccccc32)cc1]
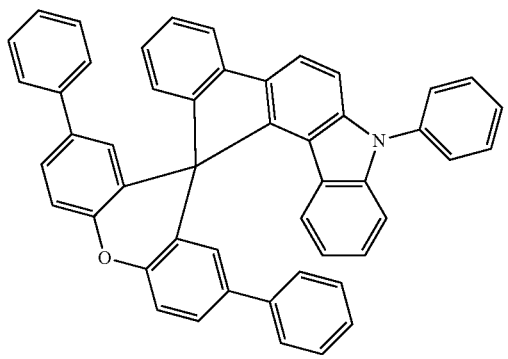 [SMILES: c1ccc(-c2ccc3c(c2)C2(c4cc(-c5ccccc5)ccc4O3)c3ccccc3-c3ccc4c(c32)c2ccccc2n4-c2ccccc2)cc1]
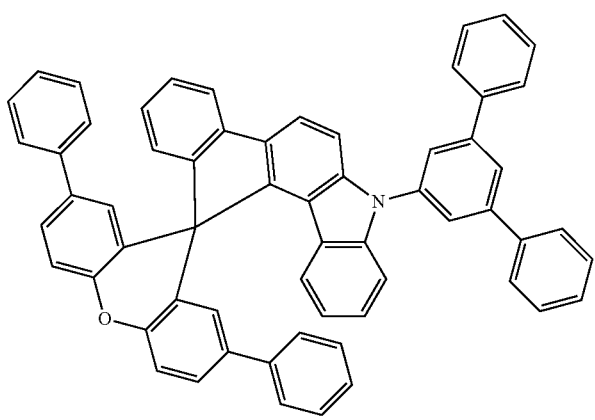 [SMILES: c1ccc(-c2cc(-c3ccccc3)cc(-n3c4ccccc4c4c5c(ccc43)-c3ccccc3C53c4cc(-c5ccccc5)ccc4Oc4ccc(-c5ccccc5)cc43)c2)cc1]

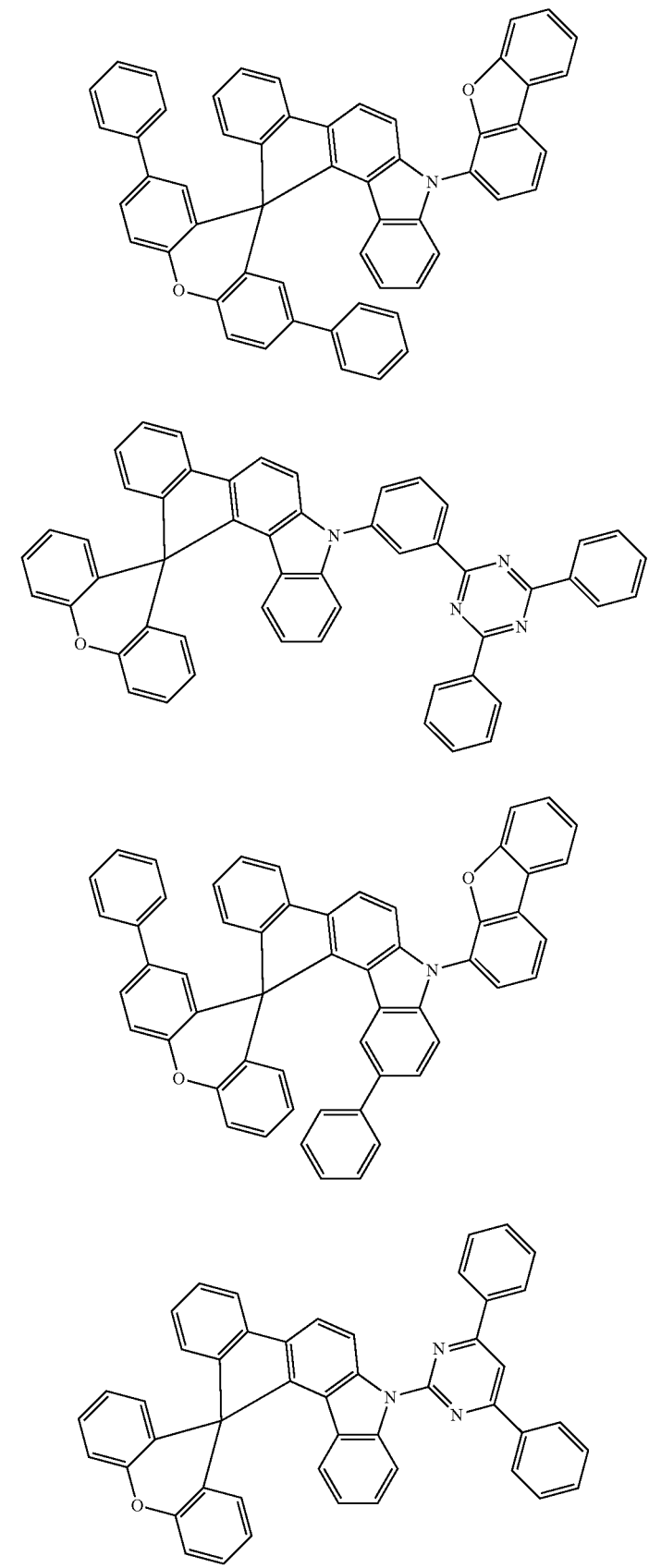

-continued
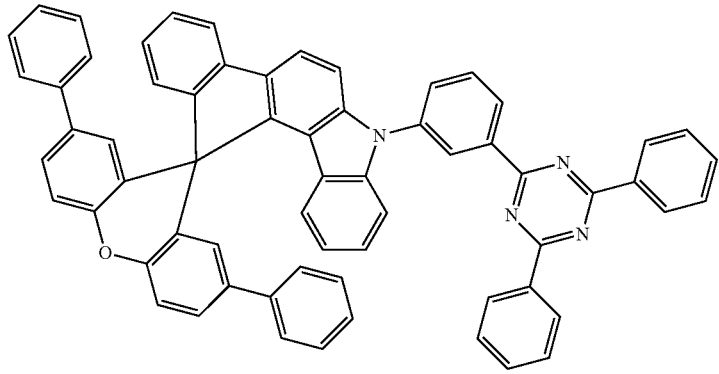 [SMILES: c1ccc(-c2ccc3c(c2)C2(c4cc(-c5ccccc5)ccc4O3)c3ccccc3-c3ccc4c(c32)c2ccccc2n4-c2cccc(-c3nc(-c4ccccc4)nc(-c4ccccc4)n3)c2)cc1]
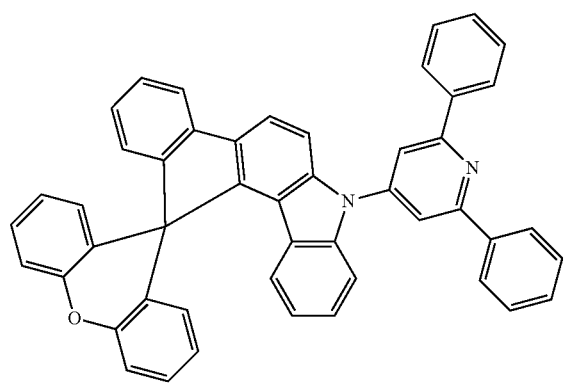 [SMILES: c1ccc(-c2cc(-n3c4ccccc4c4c5c(ccc43)-c3ccccc3C53c4ccccc4Oc4ccccc43)cc(-c3ccccc3)n2)cc1]
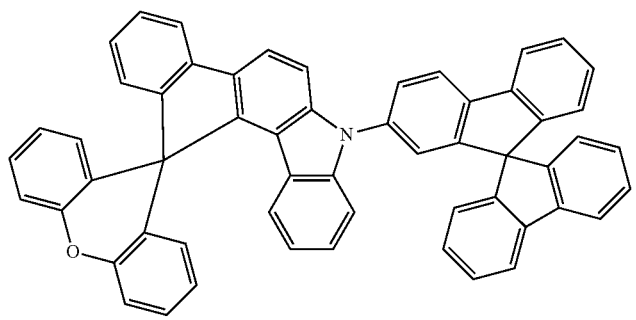 [SMILES: c1ccc2c(c1)Oc1ccccc1C21c2ccccc2-c2ccc3c(c21)c1ccccc1n3-c1ccc2c(c1)C1(c3ccccc3-c3ccccc31)c1ccccc1-2]
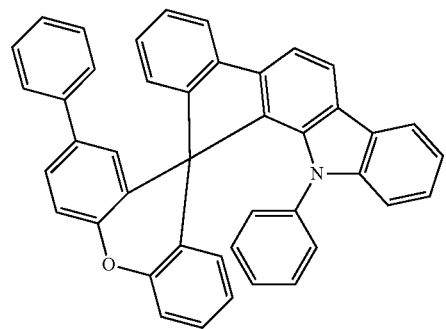 [SMILES: c1ccc(-c2ccc3c(c2)C2(c4ccccc4O3)c3ccccc3-c3ccc4c5ccccc5n(-c5ccccc5)c4c32)cc1]

-continued
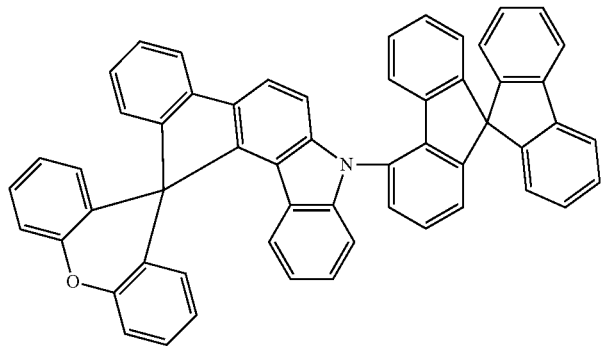 [SMILES: c1ccc2c(c1)Oc1ccccc1C21c2ccccc2-c2ccc3c(c21)c1ccccc1n3-c1cccc2c1-c1ccccc1C21c2ccccc2-c2ccccc21]
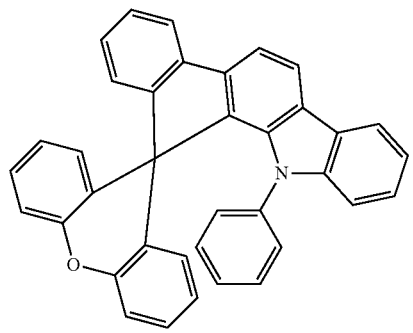 [SMILES: c1ccc(-n2c3ccccc3c3ccc4c(c32)C2(c3ccccc3Oc3ccccc32)c2ccccc2-4)cc1]
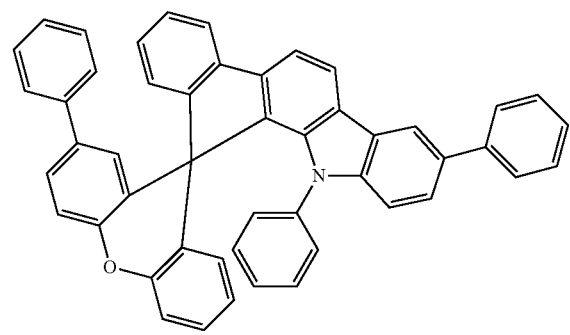 [SMILES: c1ccc(-c2ccc3c(c2)C2(c4ccccc4O3)c3ccccc3-c3ccc4c5cc(-c6ccccc6)ccc5n(-c5ccccc5)c4c32)cc1]
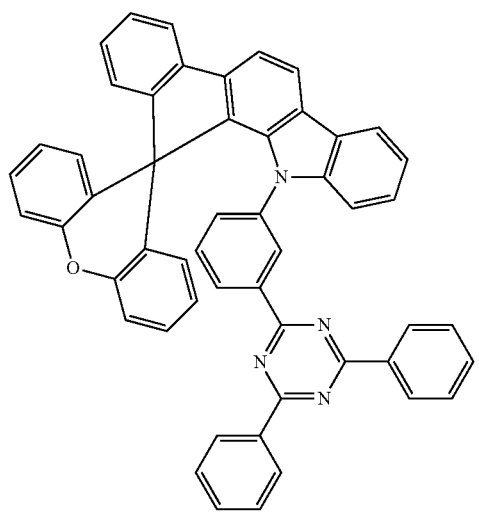 [SMILES: c1ccc(-c2nc(-c3ccccc3)nc(-c3cccc(-n4c5ccccc5c5ccc6c(c54)C4(c5ccccc5Oc5ccccc54)c4ccccc4-6)c3)n2)cc1]

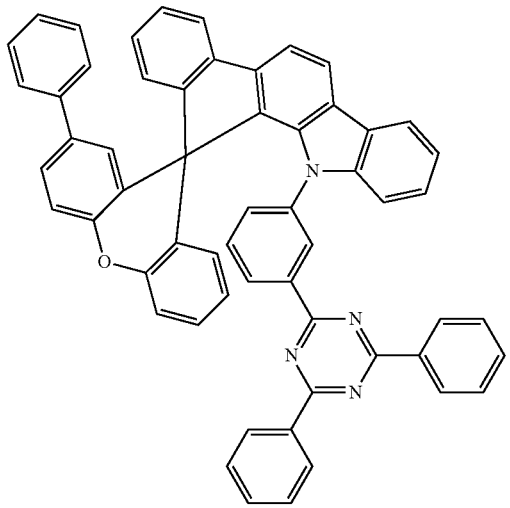 [SMILES: c1ccc(-c2ccc3c(c2)C2(c4ccccc4O3)c3ccccc3-c3ccc4c5ccccc5n(-c5cccc(-c6nc(-c7ccccc7)nc(-c7ccccc7)n6)c5)c4c32)cc1]
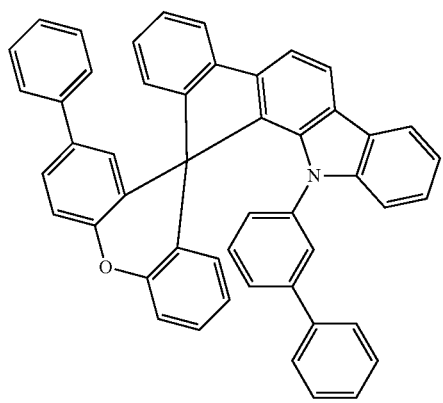 [SMILES: c1ccc(-c2cccc(-n3c4ccccc4c4ccc5c(c43)C3(c4ccccc4Oc4ccc(-c6ccccc6)cc43)c3ccccc3-5)c2)cc1]
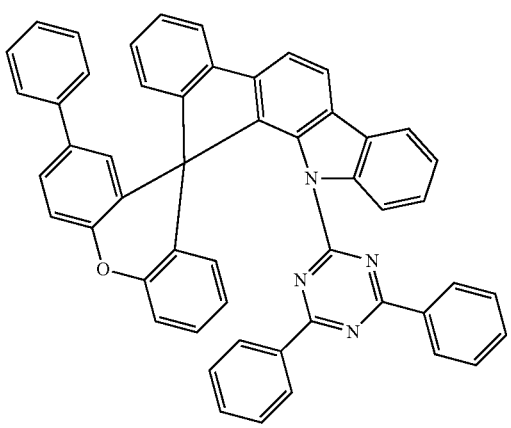 [SMILES: c1ccc(-c2ccc3c(c2)C2(c4ccccc4O3)c3ccccc3-c3ccc4c5ccccc5n(-c5nc(-c6ccccc6)nc(-c6ccccc6)n5)c4c32)cc1]

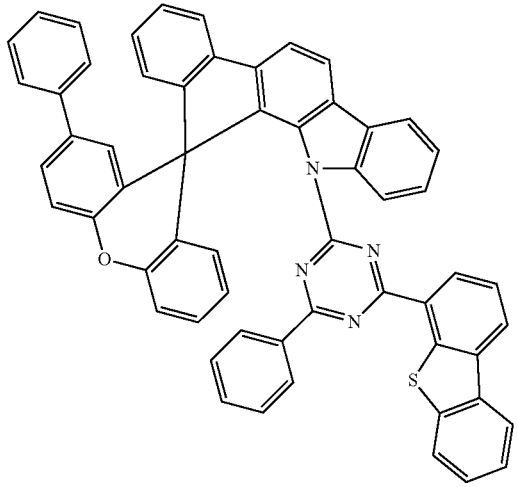 [SMILES: c1ccc(-c2ccc3c(c2)C2(c4ccccc4O3)c3ccccc3-c3ccc4c5ccccc5n(-c5nc(-c6ccccc6)nc(-c6cccc7c6sc6ccccc67)n5)c4c32)cc1]
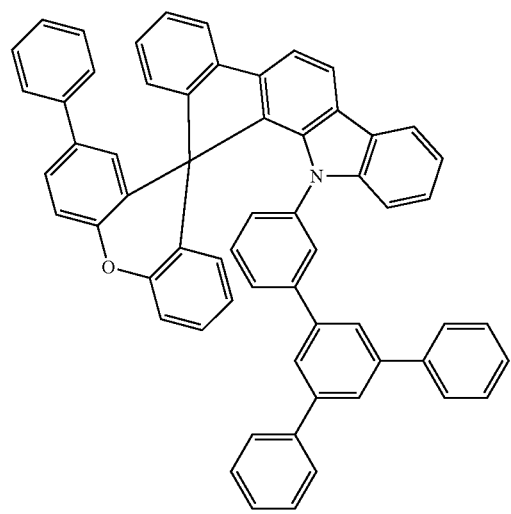 [SMILES: c1ccc(-c2cc(-c3ccccc3)cc(-c3cccc(-n4c5ccccc5c5ccc6c(c54)C4(c5ccccc5Oc5ccc(-c7ccccc7)cc54)c4ccccc4-6)c3)c2)cc1]
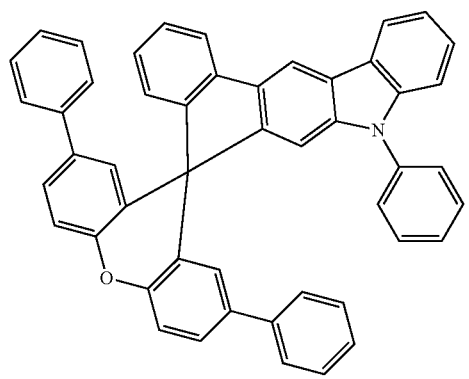 [SMILES: c1ccc(-c2ccc3c(c2)C2(c4cc(-c5ccccc5)ccc4O3)c3ccccc3-c3cc4c5ccccc5n(-c5ccccc5)c4cc32)cc1]

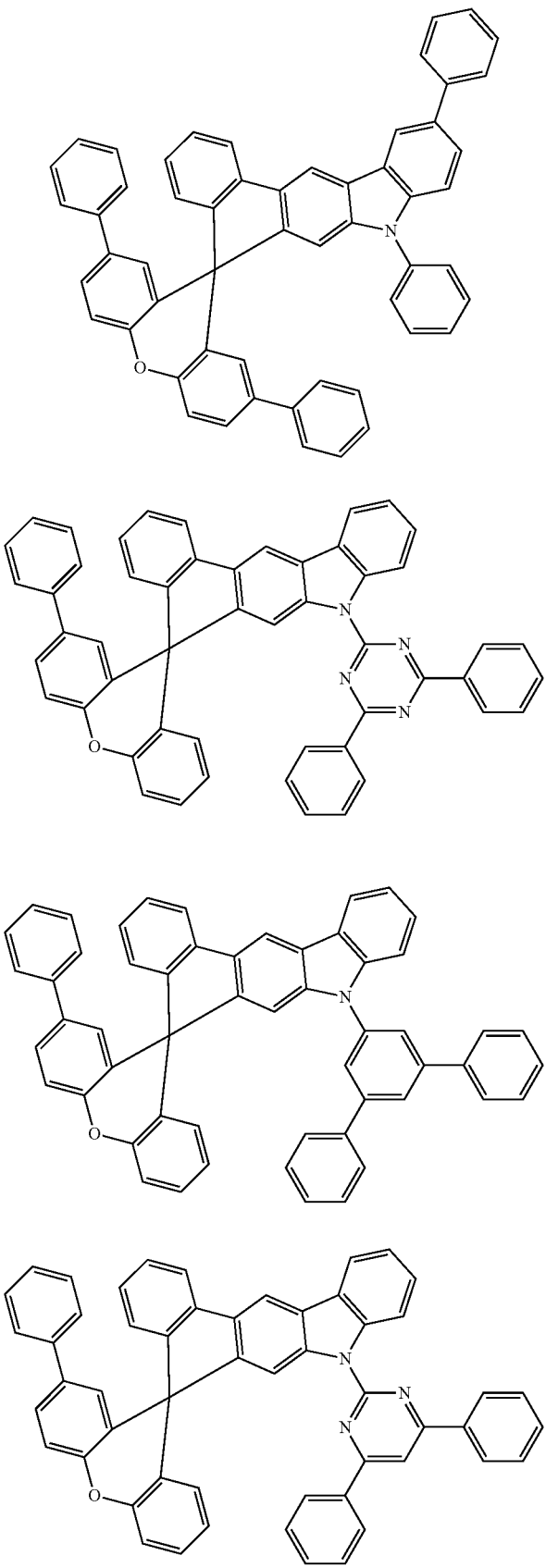

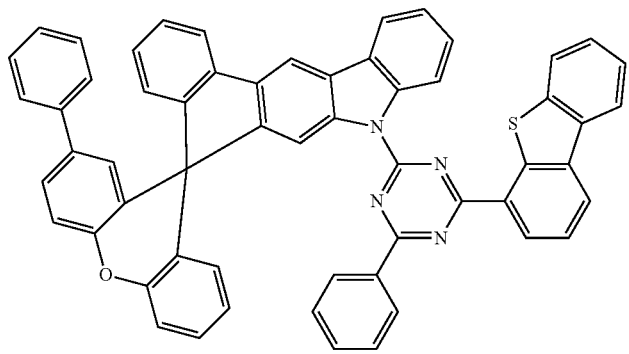 [SMILES: c1ccc(-c2ccc3c(c2)C2(c4ccccc4O3)c3ccccc3-c3cc4c5ccccc5n(-c5nc(-c6ccccc6)nc(-c6cccc7c6sc6ccccc67)n5)c4cc32)cc1]
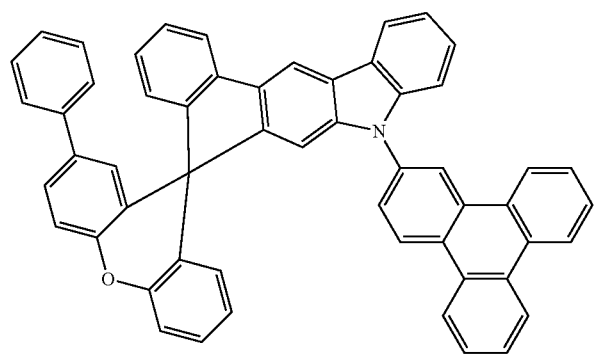 [SMILES: c1ccc(-c2ccc3c(c2)C2(c4ccccc4O3)c3ccccc3-c3cc4c5ccccc5n(-c5ccc6c7ccccc7c7ccccc7c6c5)c4cc32)cc1]
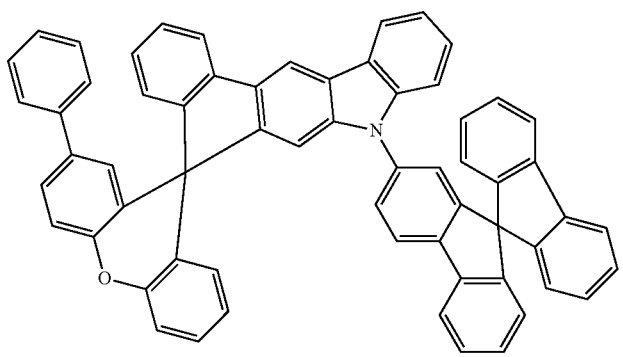 [SMILES: c1ccc(-c2ccc3c(c2)C2(c4ccccc4O3)c3ccccc3-c3cc4c5ccccc5n(-c5ccc6c(c5)C5(c7ccccc7-c7ccccc75)c5ccccc5-6)c4cc32)cc1]
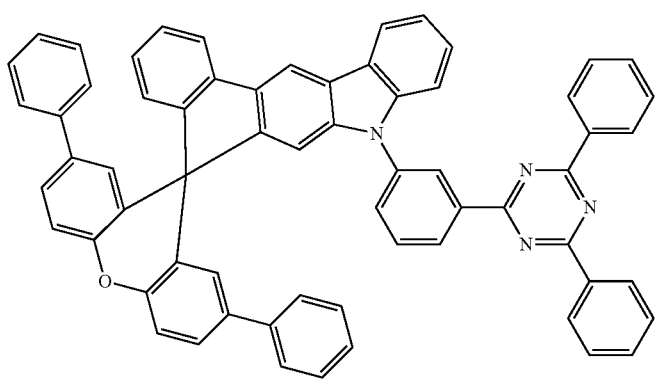 [SMILES: c1ccc(-c2ccc3c(c2)C2(c4cc(-c5ccccc5)ccc4O3)c3ccccc3-c3cc4c5ccccc5n(-c5cccc(-c6nc(-c7ccccc7)nc(-c7ccccc7)n6)c5)c4cc32)cc1]

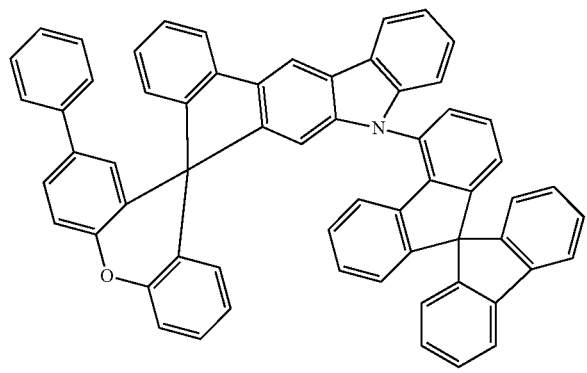 [SMILES: c1ccc(-c2ccc3c(c2)C2(c4ccccc4O3)c3ccccc3-c3cc4c5ccccc5n(-c5cccc6c5-c5ccccc5C65c6ccccc6-c6ccccc65)c4cc32)cc1]
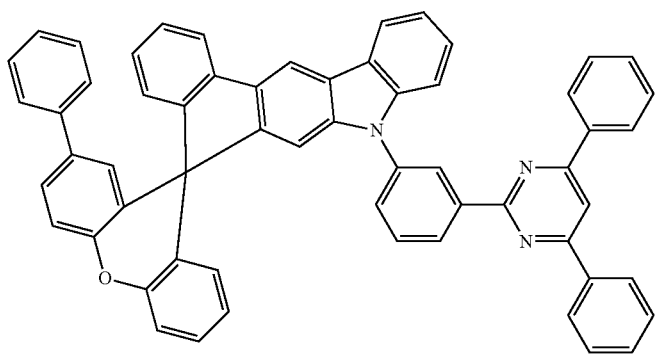 [SMILES: c1ccc(-c2ccc3c(c2)C2(c4ccccc4O3)c3ccccc3-c3cc4c5ccccc5n(-c5cccc(-c6nc(-c7ccccc7)cc(-c7ccccc7)n6)c5)c4cc32)cc1]
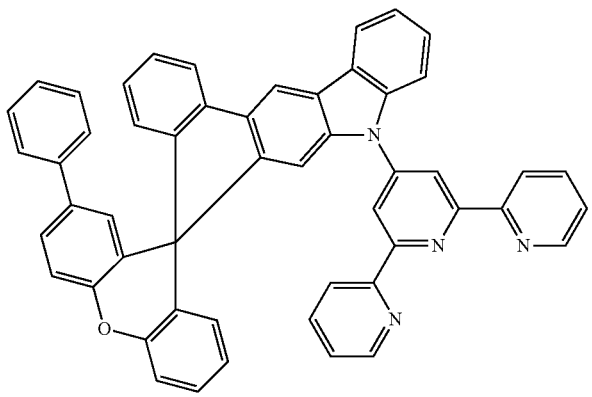 [SMILES: c1ccc(-c2ccc3c(c2)C2(c4ccccc4O3)c3ccccc3-c3cc4c5ccccc5n(-c5cc(-c6ccccn6)nc(-c6ccccn6)c5)c4cc32)cc1]
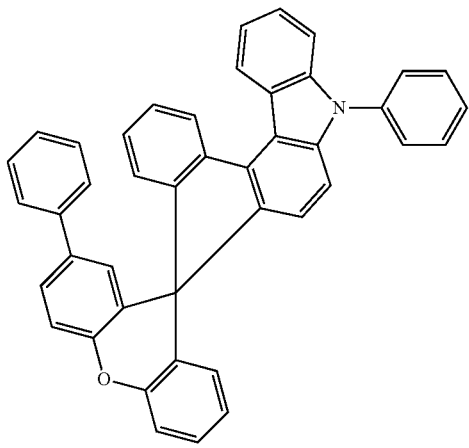 [SMILES: c1ccc(-c2ccc3c(c2)C2(c4ccccc4O3)c3ccccc3-c3c2ccc2c3c3ccccc3n2-c2ccccc2)cc1]

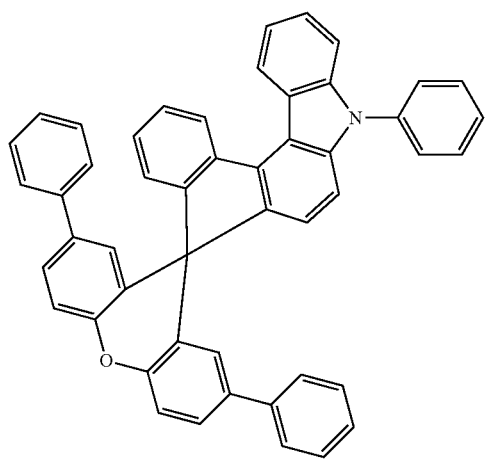 [SMILES: c1ccc(-c2ccc3c(c2)C2(c4cc(-c5ccccc5)ccc4O3)c3ccccc3-c3c2ccc2c3c3ccccc3n2-c2ccccc2)cc1]
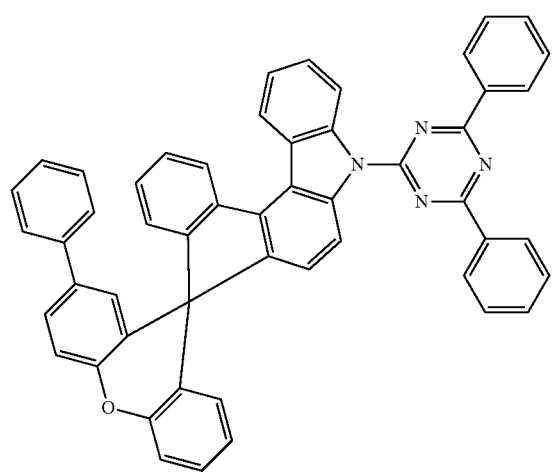
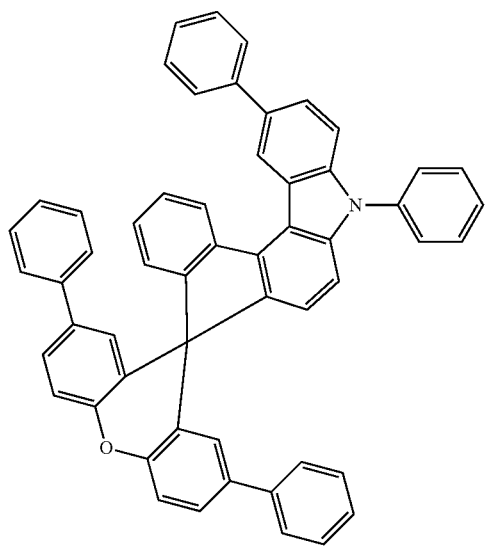 [SMILES: c1ccc(-c2ccc3c(c2)C2(c4cc(-c5ccccc5)ccc4O3)c3ccccc3-c3c2ccc2c3c3cc(-c4ccccc4)ccc3n2-c2ccccc2)cc1]

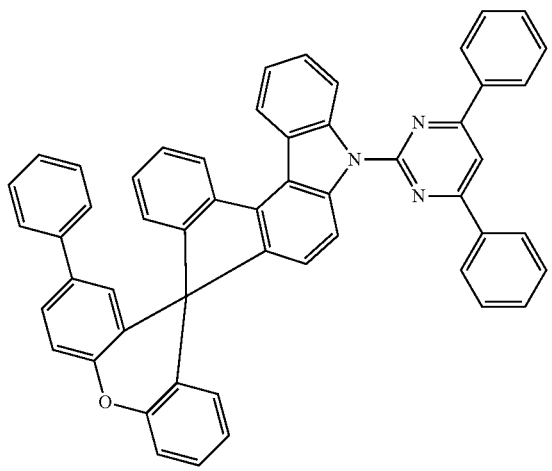 [SMILES: c1ccc(-c2ccc3c(c2)C2(c4ccccc4O3)c3ccccc3-c3c2ccc2c3c3ccccc3n2-c2nc(-c3ccccc3)cc(-c3ccccc3)n2)cc1]
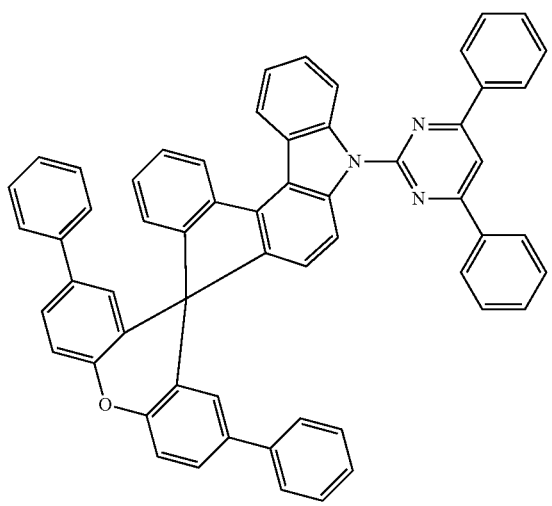 [SMILES: c1ccc(-c2ccc3c(c2)C2(c4cc(-c5ccccc5)ccc4O3)c3ccccc3-c3c2ccc2c3c3ccccc3n2-c2nc(-c3ccccc3)cc(-c3ccccc3)n2)cc1]
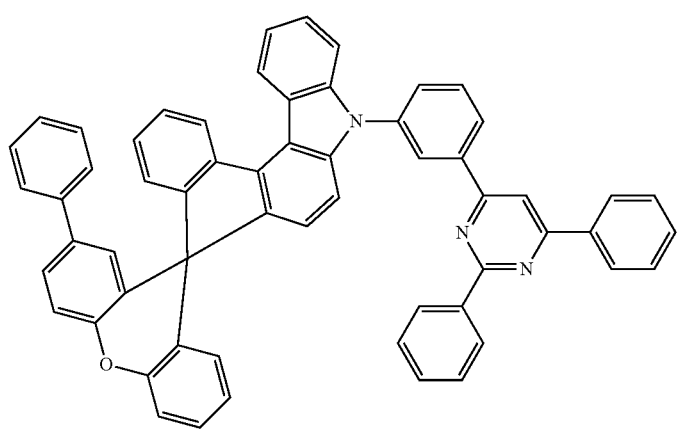 [SMILES: c1ccc(-c2ccc3c(c2)C2(c4ccccc4O3)c3ccccc3-c3c2ccc2c3c3ccccc3n2-c2cccc(-c3cc(-c4ccccc4)nc(-c4ccccc4)n3)c2)cc1]

-continued
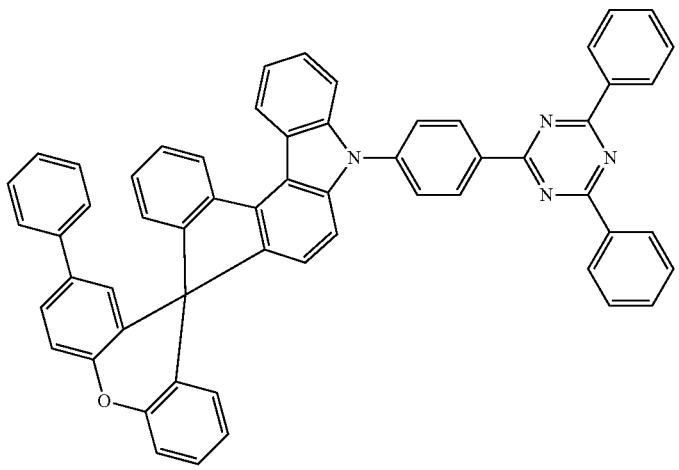 [SMILES: c1ccc(-c2ccc3c(c2)C2(c4ccccc4O3)c3ccccc3-c3c2ccc2c3c3ccccc3n2-c2ccc(-c3nc(-c4ccccc4)nc(-c4ccccc4)n3)cc2)cc1]
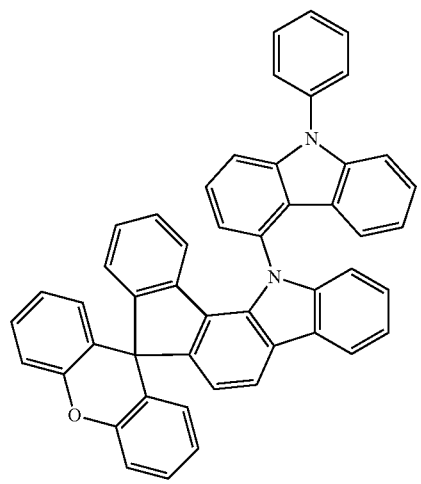 [SMILES: c1ccc(-n2c3ccccc3c3c(-n4c5ccccc5c5ccc6c(c54)-c4ccccc4C64c5ccccc5Oc5ccccc54)cccc32)cc1]
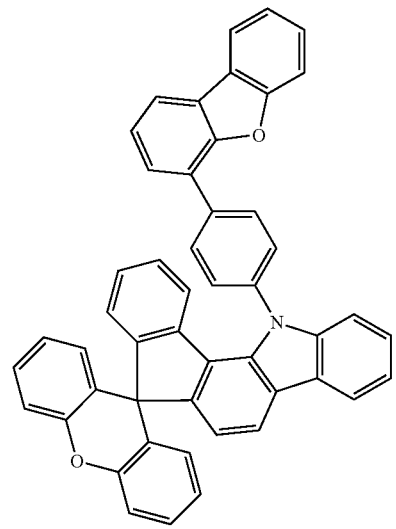 [SMILES: c1ccc2c(c1)Oc1ccccc1C21c2ccccc2-c2c1ccc1c3ccccc3n(-c3ccc(-c4cccc5c4oc4ccccc45)cc3)c21]

-continued
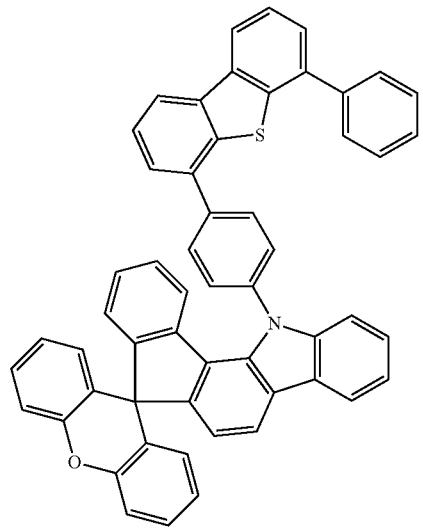 [SMILES: c1ccc(-c2cccc3c2sc2c(-c4ccc(-n5c6ccccc6c6ccc7c(c65)-c5ccccc5C75c6ccccc6Oc6ccccc65)cc4)cccc23)cc1]
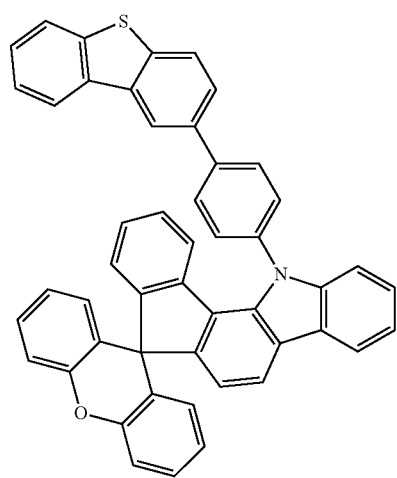 [SMILES: c1ccc2c(c1)Oc1ccccc1C21c2ccccc2-c2c1ccc1c3ccccc3n(-c3ccc(-c4ccc5sc6ccccc6c5c4)cc3)c21]
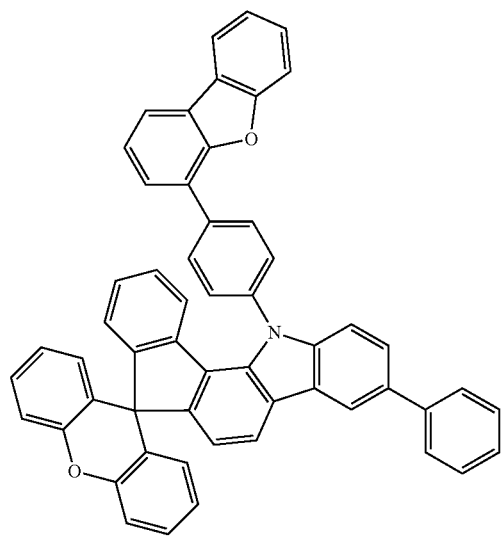 [SMILES: c1ccc(-c2ccc3c(c2)c2ccc4c(c2n3-c2ccc(-c3cccc5c3oc3ccccc35)cc2)-c2ccccc2C42c3ccccc3Oc3ccccc32)cc1]

-continued
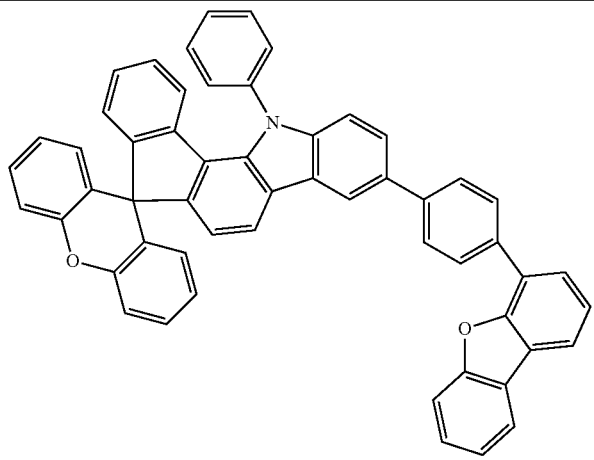
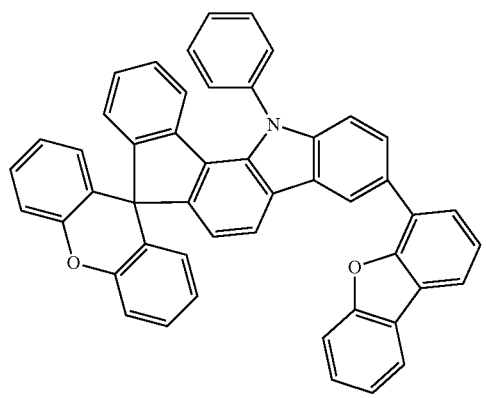 [SMILES: c1ccc(-n2c3ccc(-c4cccc5c4oc4ccccc45)cc3c3ccc4c(c32)-c2ccccc2C42c3ccccc3Oc3ccccc32)cc1]
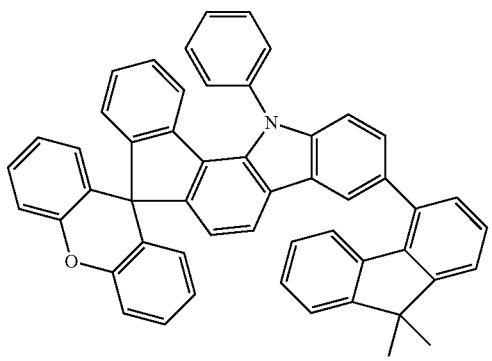 [SMILES: CC1(C)c2ccccc2-c2c(-c3ccc4c(c3)c3ccc5c(c3n4-c3ccccc3)-c3ccccc3C53c4ccccc4Oc4ccccc43)cccc21]
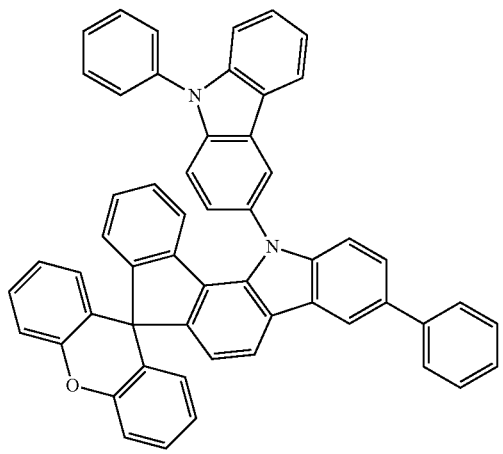 [SMILES: c1ccc(-c2ccc3c(c2)c2ccc4c(c2n3-c2ccc3c(c2)c2ccccc2n3-c2ccccc2)-c2ccccc2C42c3ccccc3Oc3ccccc32)cc1]

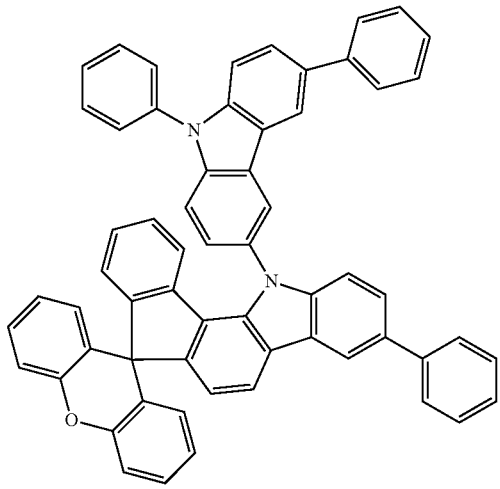 [SMILES: c1ccc(-c2ccc3c(c2)c2cc(-n4c5ccc(-c6ccccc6)cc5c5ccc6c(c54)-c4ccccc4C64c5ccccc5Oc5ccccc54)ccc2n3-c2ccccc2)cc1]
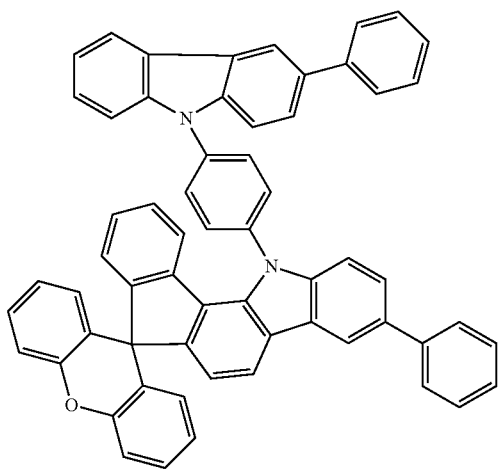 [SMILES: c1ccc(-c2ccc3c(c2)c2ccccc2n3-c2ccc(-n3c4ccc(-c5ccccc5)cc4c4ccc5c(c43)-c3ccccc3C53c4ccccc4Oc4ccccc43)cc2)cc1]
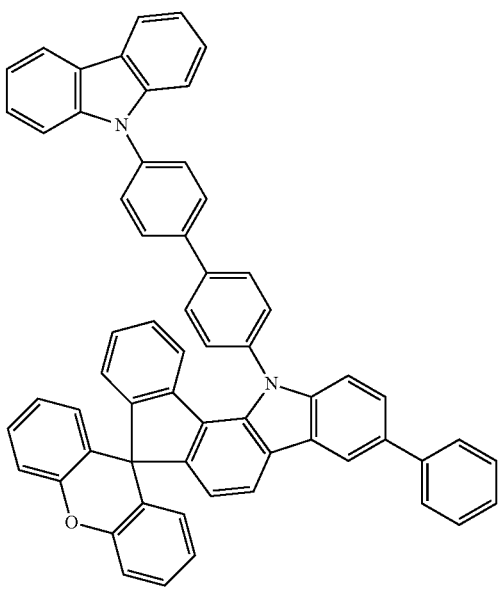 [SMILES: c1ccc(-c2ccc3c(c2)c2ccc4c(c2n3-c2ccc(-c3ccc(-n5c6ccccc6c6ccccc65)cc3)cc2)-c2ccccc2C42c3ccccc3Oc3ccccc32)cc1]

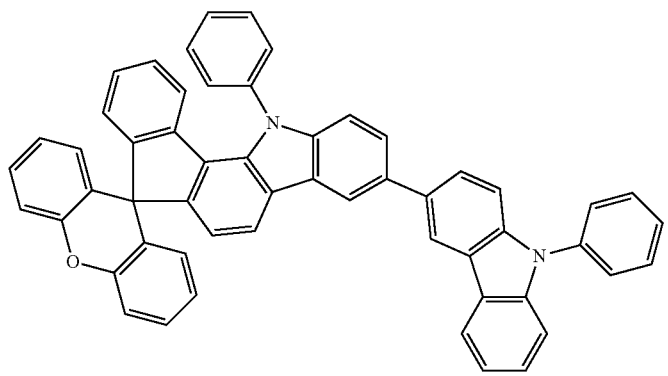 [SMILES: c1ccc(-n2c3ccccc3c3cc(-c4ccc5c(c4)c4ccc6c(c4n5-c4ccccc4)-c4ccccc4C64c5ccccc5Oc5ccccc54)ccc32)cc1]
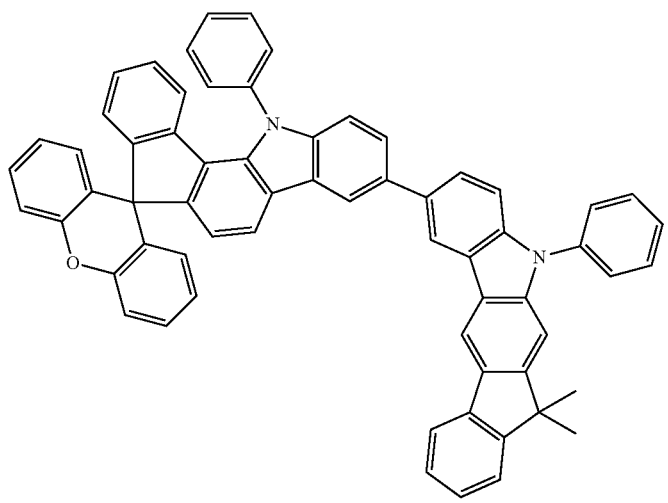 [SMILES: CC1(C)c2ccccc2-c2cc3c4cc(-c5ccc6c(c5)c5ccc7c(c5n6-c5ccccc5)-c5ccccc5C75c6ccccc6Oc6ccccc65)ccc4n(-c4ccccc4)c3cc21]
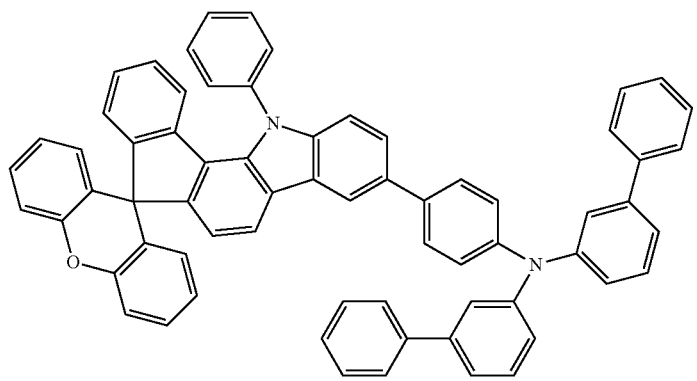 [SMILES: c1ccc(-c2cccc(N(c3ccc(-c4ccc5c(c4)c4ccc6c(c4n5-c4ccccc4)-c4ccccc4C64c5ccccc5Oc5ccccc54)cc3)c3cccc(-c4ccccc4)c3)c2)cc1]

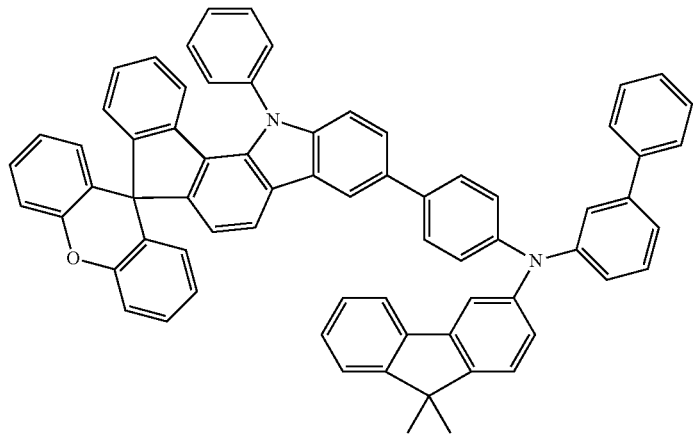 [SMILES: CC1(C)c2ccccc2-c2cc(N(c3ccc(-c4ccc5c(c4)c4ccc6c(c4n5-c4ccccc4)-c4ccccc4C64c5ccccc5Oc5ccccc54)cc3)c3cccc(-c4ccccc4)c3)ccc21]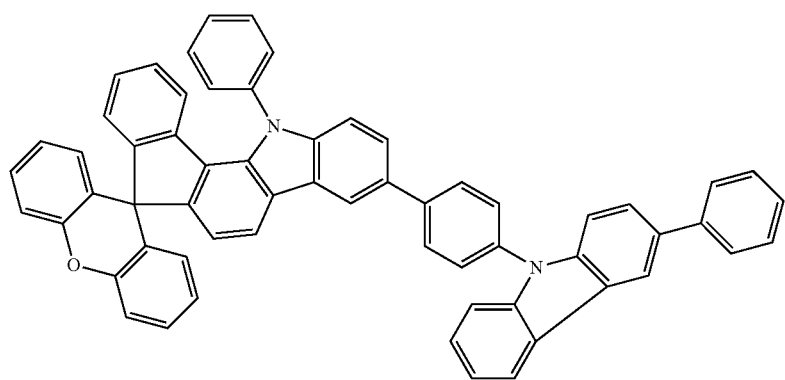 [SMILES: c1ccc(-c2ccc3c(c2)c2ccccc2n3-c2ccc(-c3ccc4c(c3)c3ccc5c(c3n4-c3ccccc3)-c3ccccc3C53c4ccccc4Oc4ccccc43)cc2)cc1]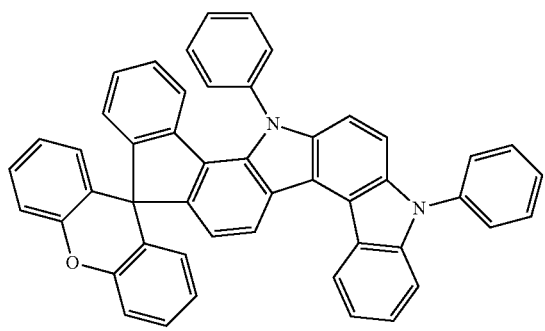 [SMILES: c1ccc(-n2c3ccccc3c3c4c5ccc6c(c5n(-c5ccccc5)c4ccc32)-c2ccccc2C62c3ccccc3Oc3ccccc32)cc1]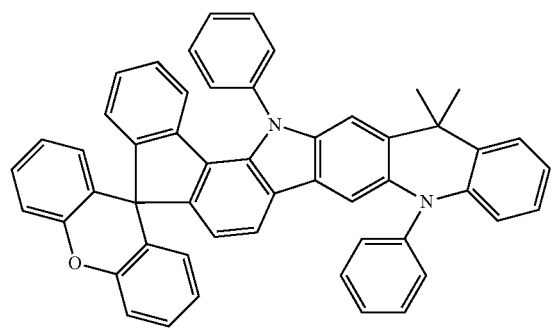 [SMILES: CC1(C)c2ccccc2N(c2ccccc2)c2cc3c4ccc5c(c4n(-c4ccccc4)c3cc21)-c1ccccc1C51c2ccccc2Oc2ccccc21]

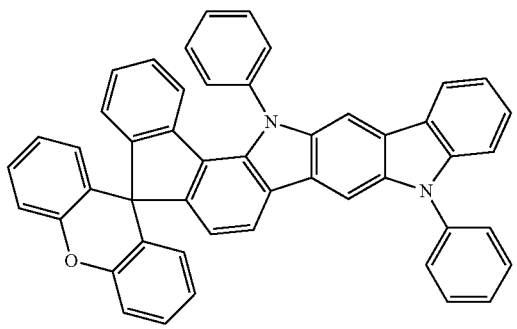 [SMILES: c1ccc(-n2c3ccccc3c3cc4c(cc32)c2ccc3c(c2n4-c2ccccc2)-c2ccccc2C32c3ccccc3Oc3ccccc32)cc1]
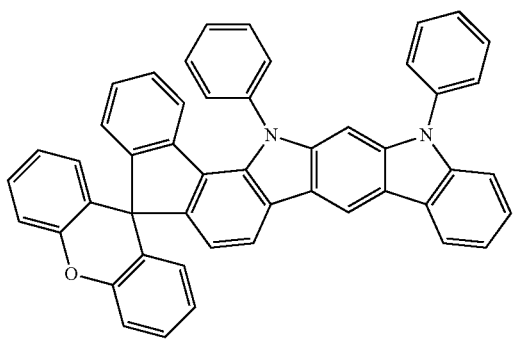 [SMILES: c1ccc(-n2c3ccccc3c3cc4c5ccc6c(c5n(-c5ccccc5)c4cc32)-c2ccccc2C62c3ccccc3Oc3ccccc32)cc1]
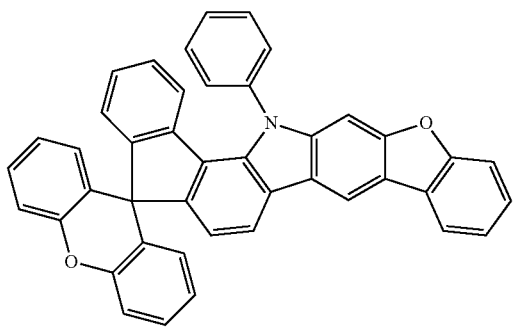 [SMILES: c1ccc(-n2c3cc4oc5ccccc5c4cc3c3ccc4c(c32)-c2ccccc2C42c3ccccc3Oc3ccccc32)cc1]
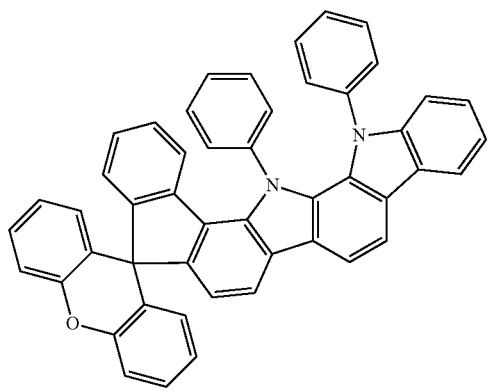 [SMILES: c1ccc(-n2c3ccccc3c3ccc4c5ccc6c(c5n(-c5ccccc5)c4c32)-c2ccccc2C62c3ccccc3Oc3ccccc32)cc1]

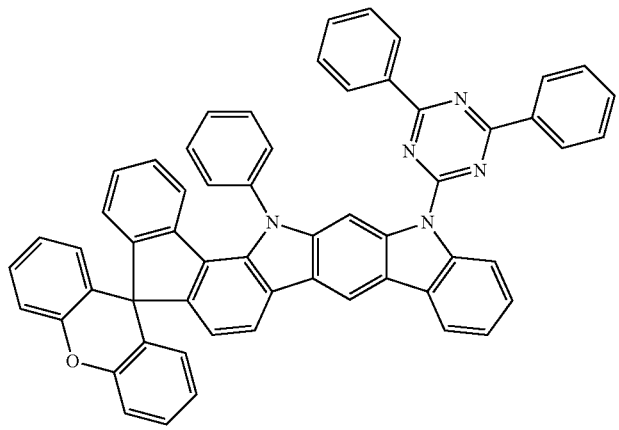 [SMILES: c1ccc(-c2nc(-c3ccccc3)nc(-n3c4ccccc4c4cc5c6ccc7c(c6n(-c6ccccc6)c5cc43)-c3ccccc3C73c4ccccc4Oc4ccccc43)n2)cc1]
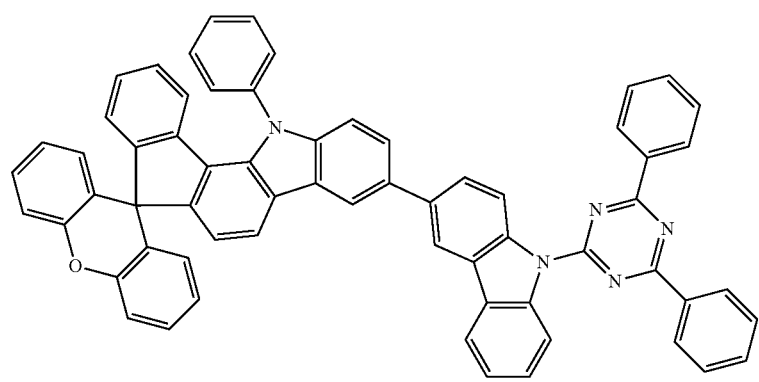 [SMILES: c1ccc(-c2nc(-c3ccccc3)nc(-n3c4ccccc4c4cc(-c5ccc6c(c5)c5ccc7c(c5n6-c5ccccc5)-c5ccccc5C75c6ccccc6Oc6ccccc65)ccc43)n2)cc1]
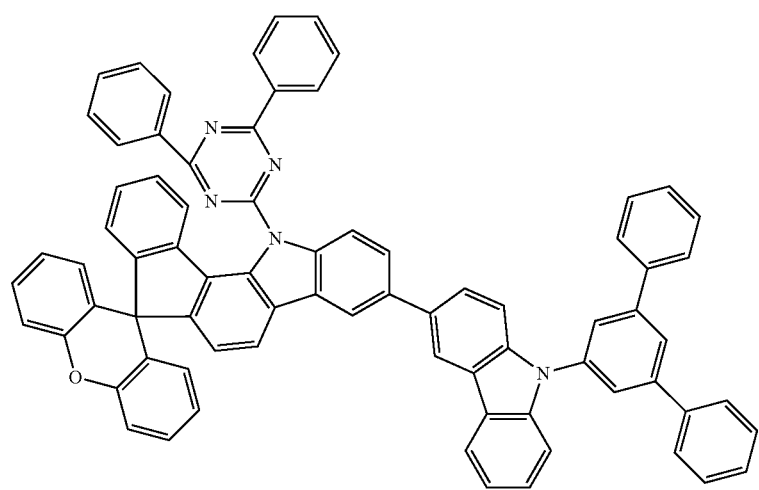 [SMILES: c1ccc(-c2cc(-c3ccccc3)cc(-n3c4ccccc4c4cc(-c5ccc6c(c5)c5ccc7c(c5n6-c5nc(-c6ccccc6)nc(-c6ccccc6)n5)-c5ccccc5C75c6ccccc6Oc6ccccc65)ccc43)c2)cc1]

-continued
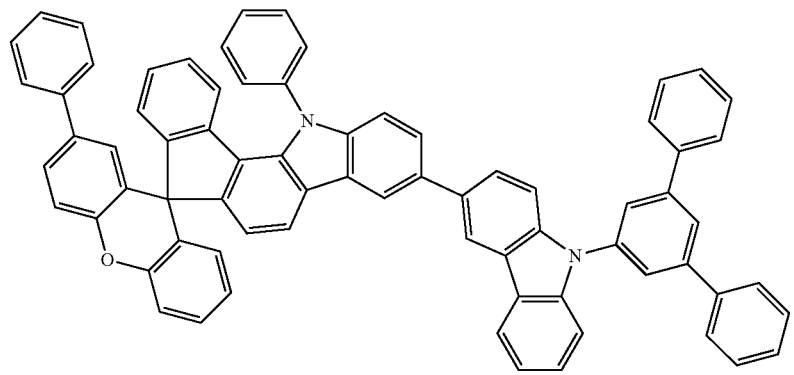 [SMILES: c1ccc(-c2cc(-c3ccccc3)cc(-n3c4ccccc4c4cc(-c5ccc6c(c5)c5ccc7c(c5n6-c5ccccc5)-c5ccccc5C75c6ccccc6Oc6ccc(-c7ccccc7)cc65)ccc43)c2)cc1]
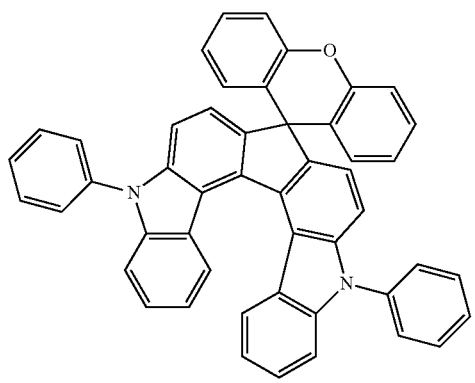 [SMILES: c1ccc(-n2c3ccccc3c3c4c(ccc32)C2(c3ccccc3Oc3ccccc32)c2ccc3c(c2-4)c2ccccc2n3-c2ccccc2)cc1]
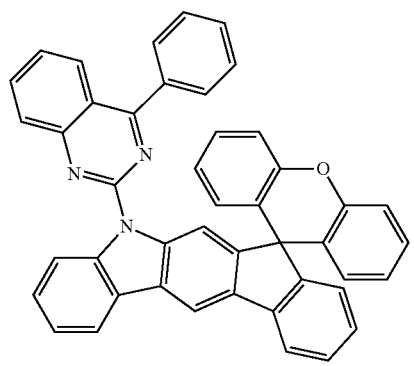 [SMILES: c1ccc(-c2nc(-n3c4ccccc4c4cc5c(cc43)C3(c4ccccc4Oc4ccccc43)c3ccccc3-5)nc3ccccc23)cc1]
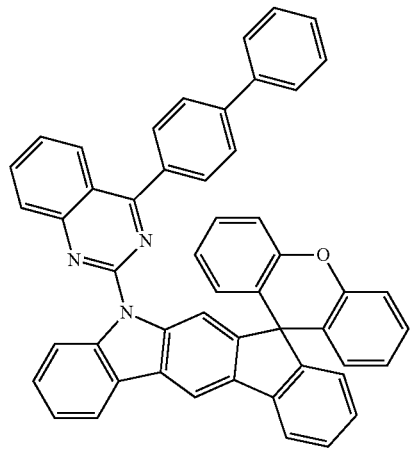 [SMILES: c1ccc(-c2ccc(-c3nc(-n4c5ccccc5c5cc6c(cc54)C4(c5ccccc5Oc5ccccc54)c4ccccc4-6)nc4ccccc34)cc2)cc1]

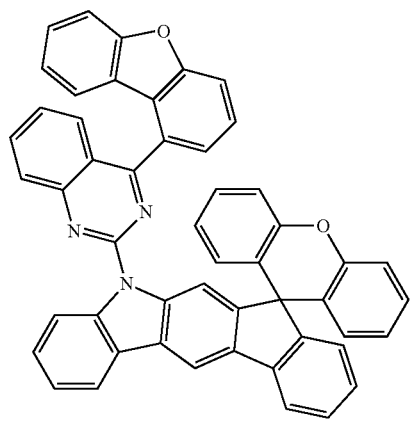 [SMILES: c1ccc2c(c1)Oc1ccccc1C21c2ccccc2-c2cc3c4ccccc4n(-c4nc(-c5cccc6oc7ccccc7c56)c5ccccc5n4)c3cc21]
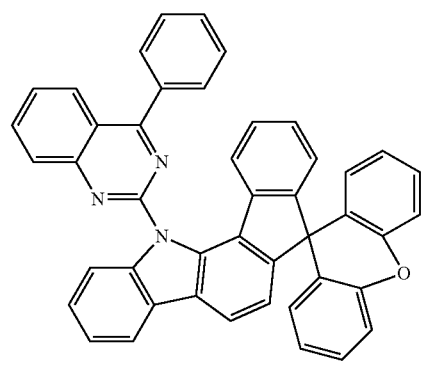 [SMILES: c1ccc(-c2nc(-n3c4ccccc4c4ccc5c(c43)-c3ccccc3C53c4ccccc4Oc4ccccc43)nc3ccccc23)cc1]
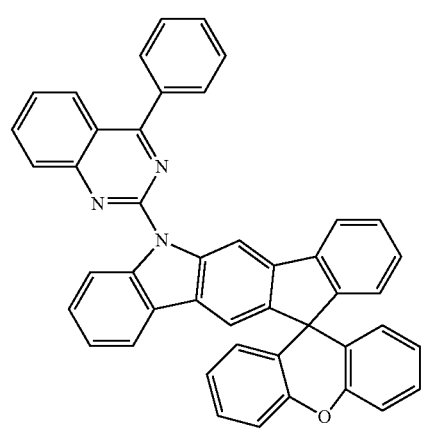 [SMILES: c1ccc(-c2nc(-n3c4ccccc4c4cc5c(cc43)-c3ccccc3C53c4ccccc4Oc4ccccc43)nc3ccccc23)cc1]

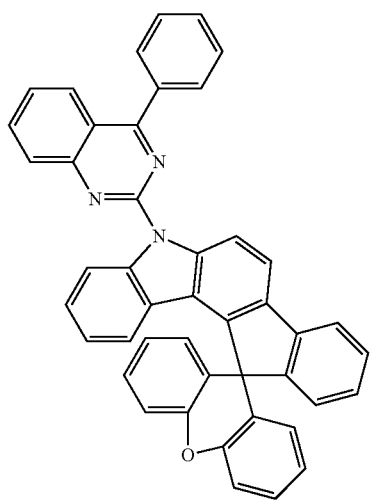 [SMILES: c1ccc(-c2nc(-n3c4ccccc4c4c5c(ccc43)-c3ccccc3C53c4ccccc4Oc4ccccc43)nc3ccccc23)cc1]
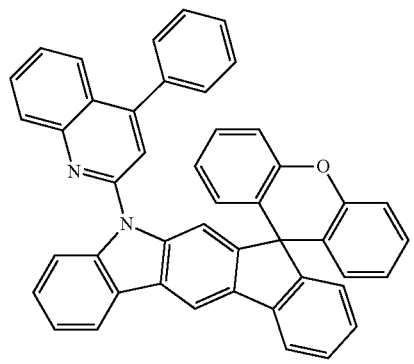
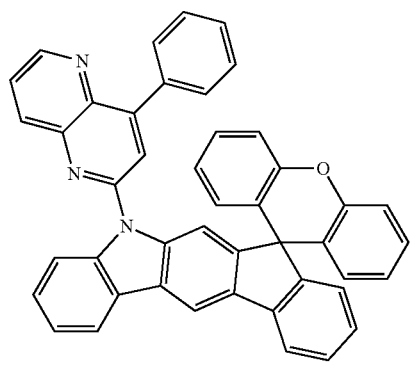
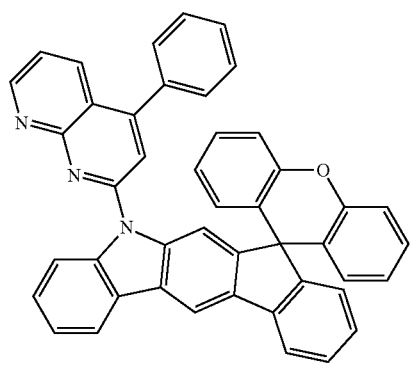 [SMILES: c1ccc(-c2cc(-n3c4ccccc4c4cc5c(cc43)C3(c4ccccc4Oc4ccccc43)c3ccccc3-5)nc3ccccc23)cc1]

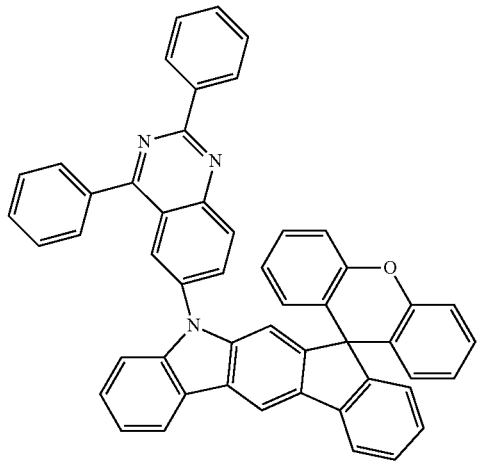 [SMILES: c1ccc(-c2nc(-c3ccccc3)c3cc(-n4c5ccccc5c5cc6c(cc54)C4(c5ccccc5Oc5ccccc54)c4ccccc4-6)ccc3n2)cc1]
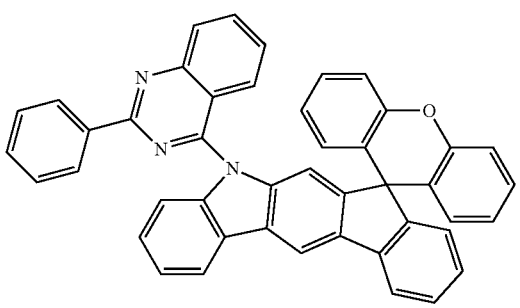 [SMILES: c1ccc(-c2nc(-n3c4ccccc4c4cc5c(cc43)C3(c4ccccc4Oc4ccccc43)c3ccccc3-5)c3ccccc3n2)cc1]
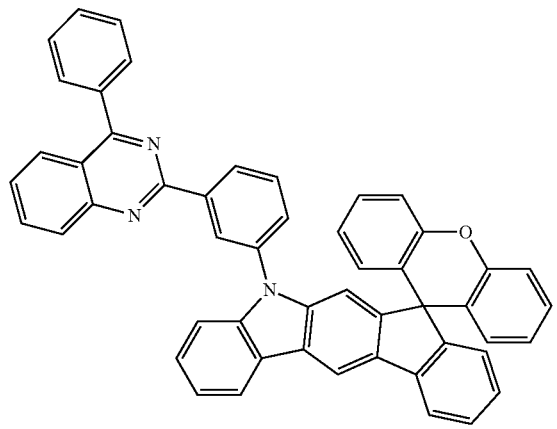 [SMILES: c1ccc(-c2nc(-c3cccc(-n4c5ccccc5c5cc6c(cc54)C4(c5ccccc5Oc5ccccc54)c4ccccc4-6)c3)nc3ccccc23)cc1]
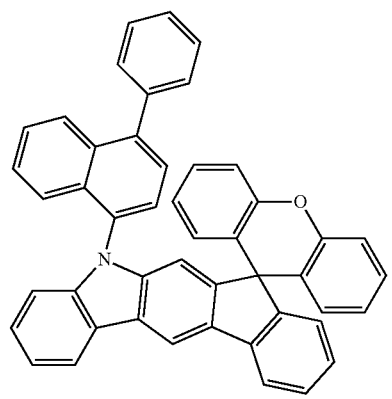 [SMILES: c1ccc(-c2ccc(-n3c4ccccc4c4cc5c(cc43)C3(c4ccccc4Oc4ccccc43)c3ccccc3-5)c3ccccc23)cc1]

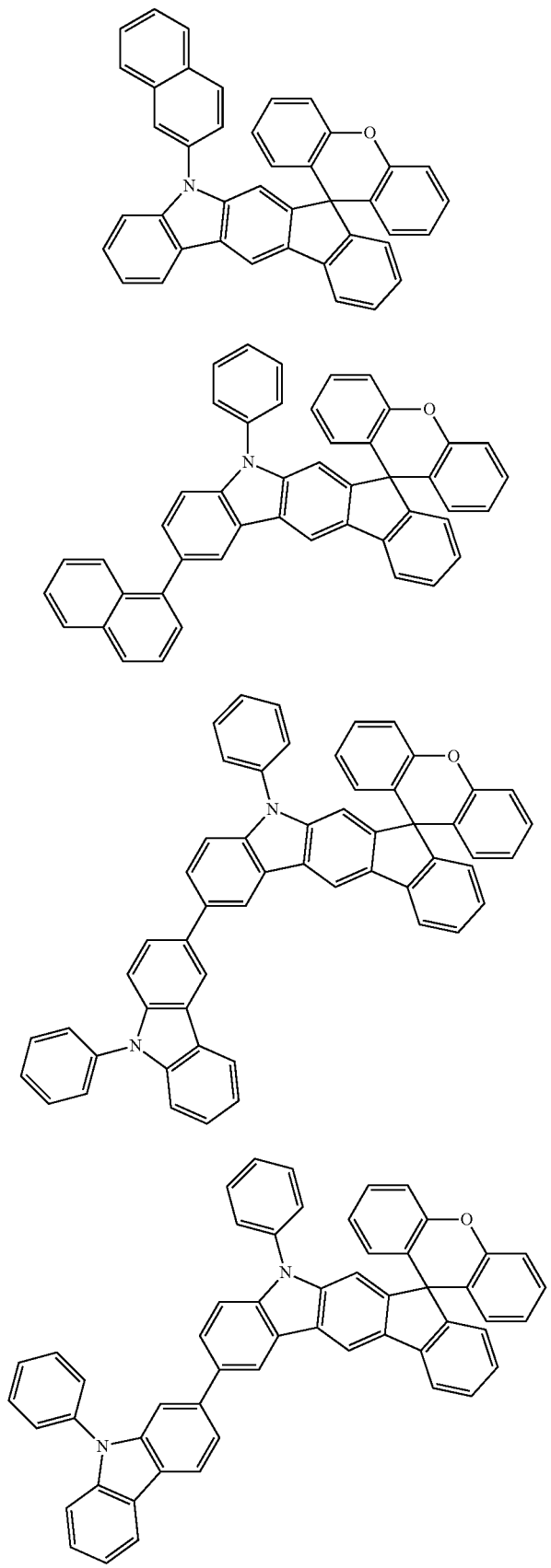

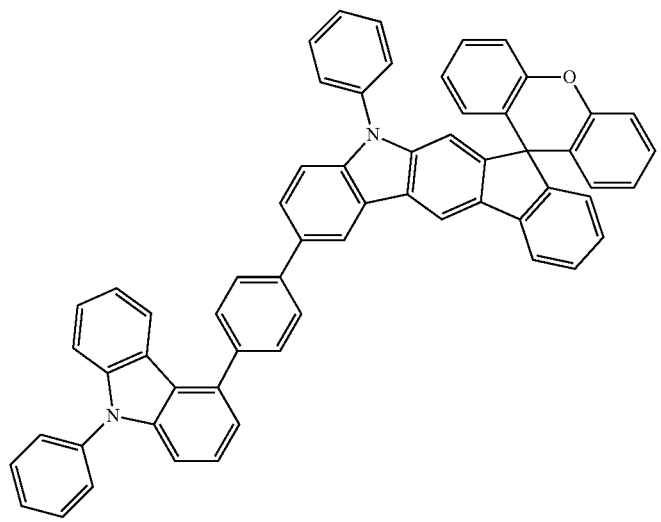 [SMILES: c1ccc(-n2c3ccc(-c4ccc(-c5cccc6c5c5ccccc5n6-c5ccccc5)cc4)cc3c3cc4c(cc32)C2(c3ccccc3Oc3ccccc32)c2ccccc2-4)cc1]
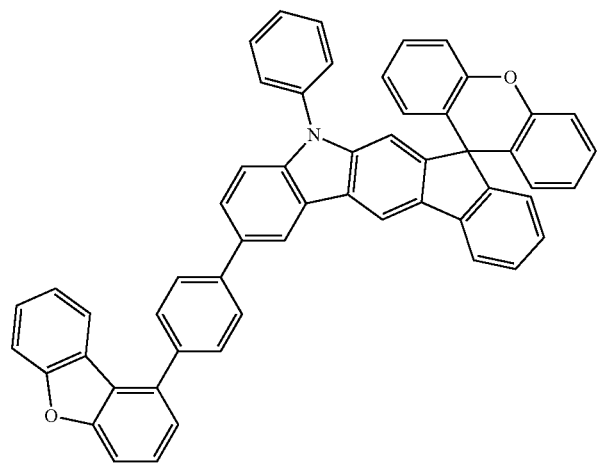 [SMILES: c1ccc(-n2c3ccc(-c4ccc(-c5cccc6oc7ccccc7c56)cc4)cc3c3cc4c(cc32)C2(c3ccccc3Oc3ccccc32)c2ccccc2-4)cc1]
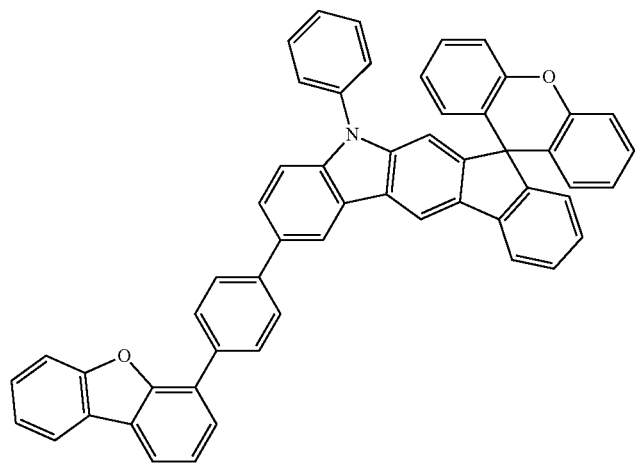 [SMILES: c1ccc(-n2c3ccc(-c4ccc(-c5cccc6c5oc5ccccc56)cc4)cc3c3cc4c(cc32)C2(c3ccccc3Oc3ccccc32)c2ccccc2-4)cc1]

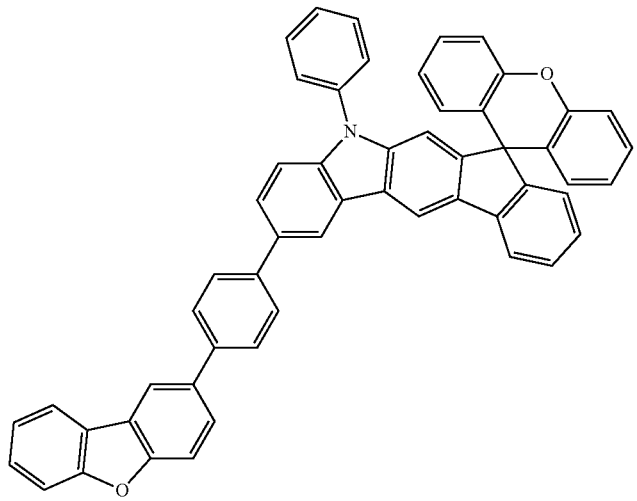 [SMILES: c1ccc(-n2c3ccc(-c4ccc(-c5ccc6oc7ccccc7c6c5)cc4)cc3c3cc4c(cc32)C2(c3ccccc3Oc3ccccc32)c2ccccc2-4)cc1]
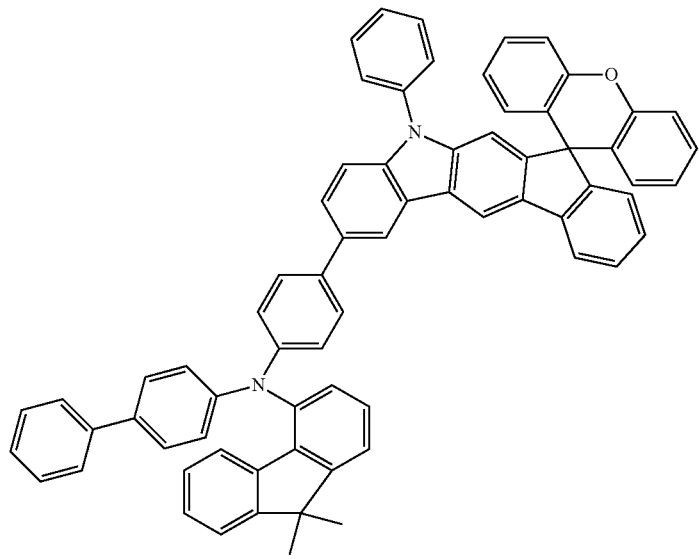 [SMILES: CC1(C)c2ccccc2-c2c(N(c3ccc(-c4ccccc4)cc3)c3ccc(-c4ccc5c(c4)c4cc6c(cc4n5-c4ccccc4)C4(c5ccccc5Oc5ccccc54)c4ccccc4-6)cc3)cccc21]
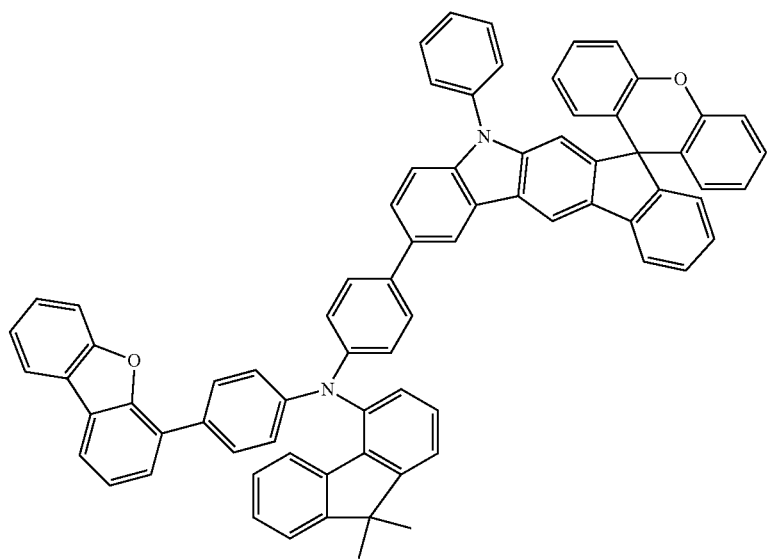 [SMILES: CC1(C)c2ccccc2-c2c(N(c3ccc(-c4ccc5c(c4)c4cc6c(cc4n5-c4ccccc4)C4(c5ccccc5Oc5ccccc54)c4ccccc4-6)cc3)c3ccc(-c4cccc5c4oc4ccccc45)cc3)cccc21]

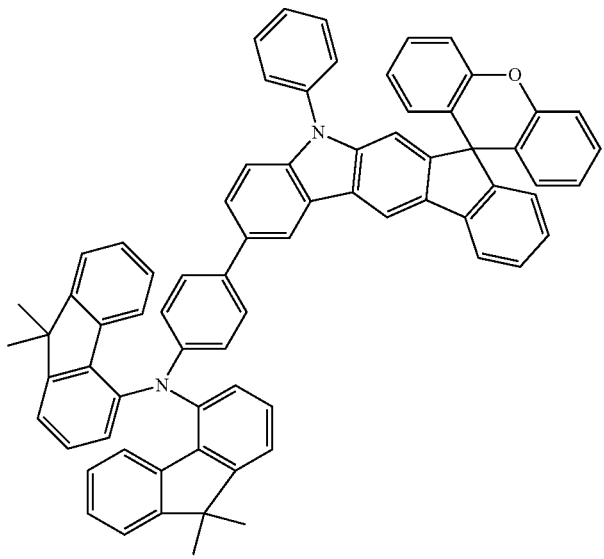 [SMILES: CC1(C)c2ccccc2-c2c(N(c3ccc(-c4ccc5c(c4)c4cc6c(cc4n5-c4ccccc4)C4(c5ccccc5Oc5ccccc54)c4ccccc4-6)cc3)c3cccc4c3-c3ccccc3C4(C)C)cccc21]
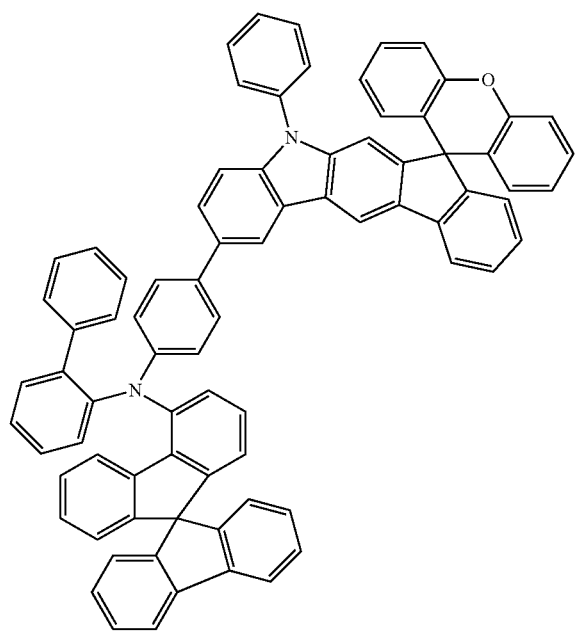 [SMILES: c1ccc(-c2ccccc2N(c2ccc(-c3ccc4c(c3)c3cc5c(cc3n4-c3ccccc3)C3(c4ccccc4Oc4ccccc43)c3ccccc3-5)cc2)c2cccc3c2-c2ccccc2C32c3ccccc3-c3ccccc32)cc1]

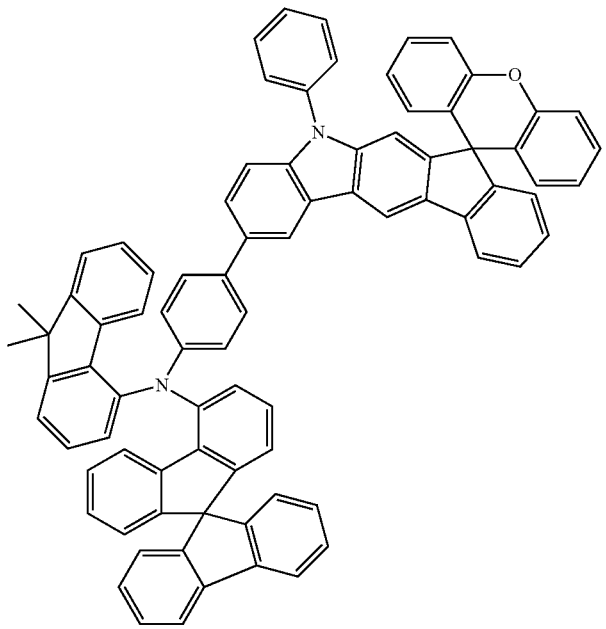 [SMILES: CC1(C)c2ccccc2-c2c(N(c3ccc(-c4ccc5c(c4)c4cc6c(cc4n5-c4ccccc4)C4(c5ccccc5Oc5ccccc54)c4ccccc4-6)cc3)c3cccc4c3-c3ccccc3C43c4ccccc4-c4ccccc43)cccc21]
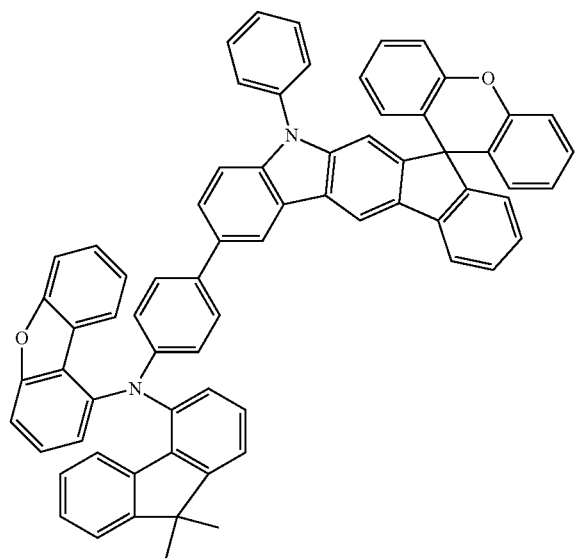 [SMILES: CC1(C)c2ccccc2-c2c(N(c3ccc(-c4ccc5c(c4)c4cc6c(cc4n5-c4ccccc4)C4(c5ccccc5Oc5ccccc54)c4ccccc4-6)cc3)c3cccc4oc5ccccc5c34)cccc21]

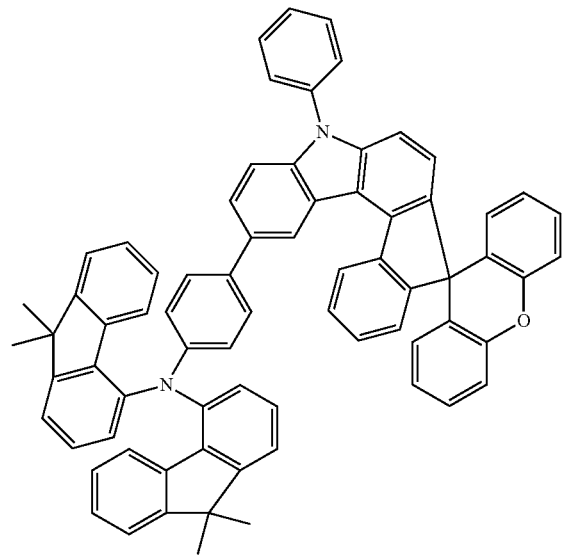 [SMILES: CC1(C)c2ccccc2-c2c(N(c3ccc(-c4ccc5c(c4)c4c6c(ccc4n5-c4ccccc4)C4(c5ccccc5Oc5ccccc54)c4ccccc4-6)cc3)c3cccc4c3-c3ccccc3C4(C)C)cccc21]
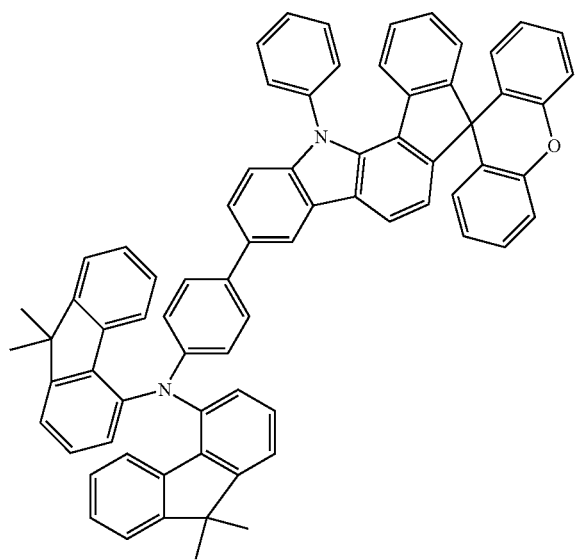 [SMILES: CC1(C)c2ccccc2-c2c(N(c3ccc(-c4ccc5c(c4)c4ccc6c(c4n5-c4ccccc4)-c4ccccc4C64c5ccccc5Oc5ccccc54)cc3)c3cccc4c3-c3ccccc3C4(C)C)cccc21]

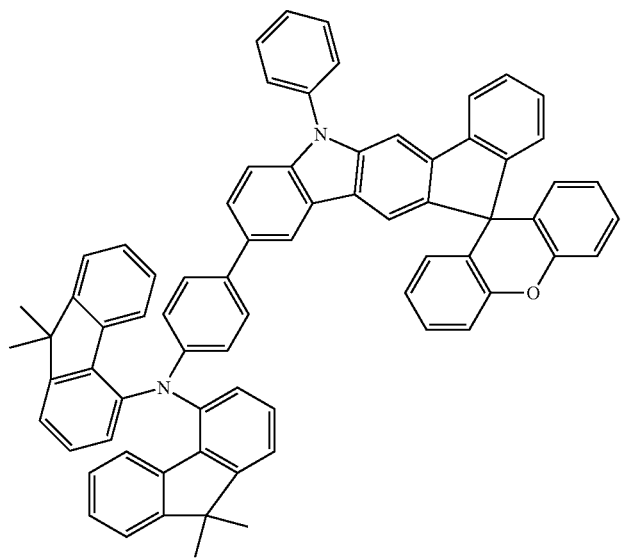 [SMILES: CC1(C)c2ccccc2-c2c(N(c3ccc(-c4ccc5c(c4)c4cc6c(cc4n5-c4ccccc4)-c4ccccc4C64c5ccccc5Oc5ccccc54)cc3)c3cccc4c3-c3ccccc3C4(C)C)cccc21]
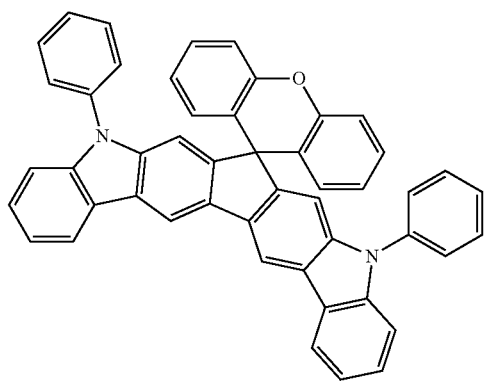 [SMILES: c1ccc(-n2c3ccccc3c3cc4c(cc32)C2(c3ccccc3Oc3ccccc32)c2cc3c(cc2-4)c2ccccc2n3-c2ccccc2)cc1]
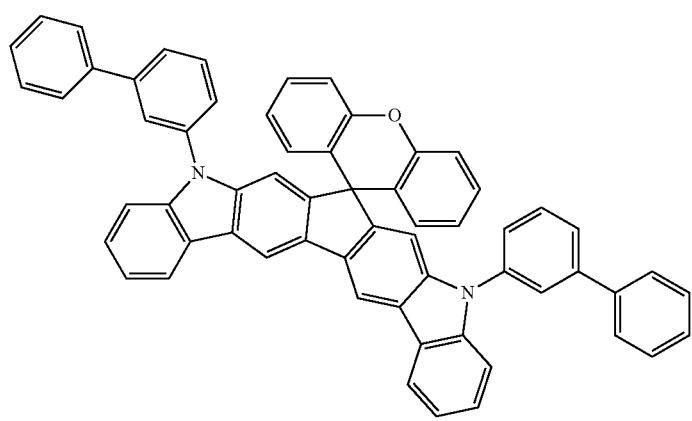 [SMILES: c1ccc(-c2cccc(-n3c4ccccc4c4cc5c(cc43)C3(c4ccccc4Oc4ccccc43)c3cc4c(cc3-5)c3ccccc3n4-c3cccc(-c4ccccc4)c3)c2)cc1]

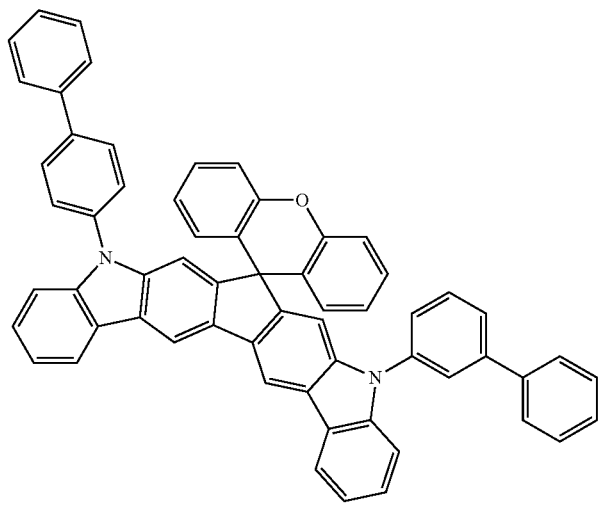 [SMILES: c1ccc(-c2ccc(-n3c4ccccc4c4cc5c(cc43)C3(c4ccccc4Oc4ccccc43)c3cc4c(cc3-5)c3ccccc3n4-c3cccc(-c4ccccc4)c3)cc2)cc1]
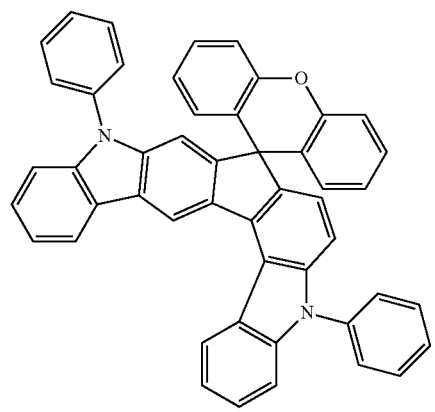 [SMILES: c1ccc(-n2c3ccccc3c3cc4c(cc32)C2(c3ccccc3Oc3ccccc32)c2ccc3c(c2-4)c2ccccc2n3-c2ccccc2)cc1]
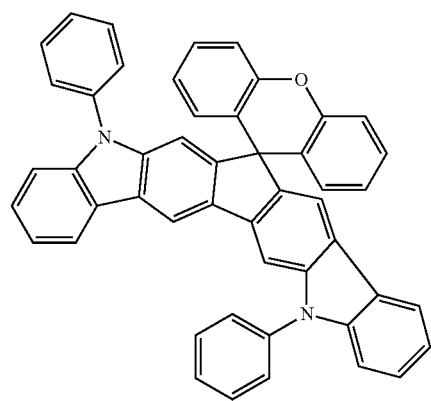 [SMILES: c1ccc(-n2c3ccccc3c3cc4c(cc32)-c2cc3c5ccccc5n(-c5ccccc5)c3cc2C42c3ccccc3Oc3ccccc32)cc1]

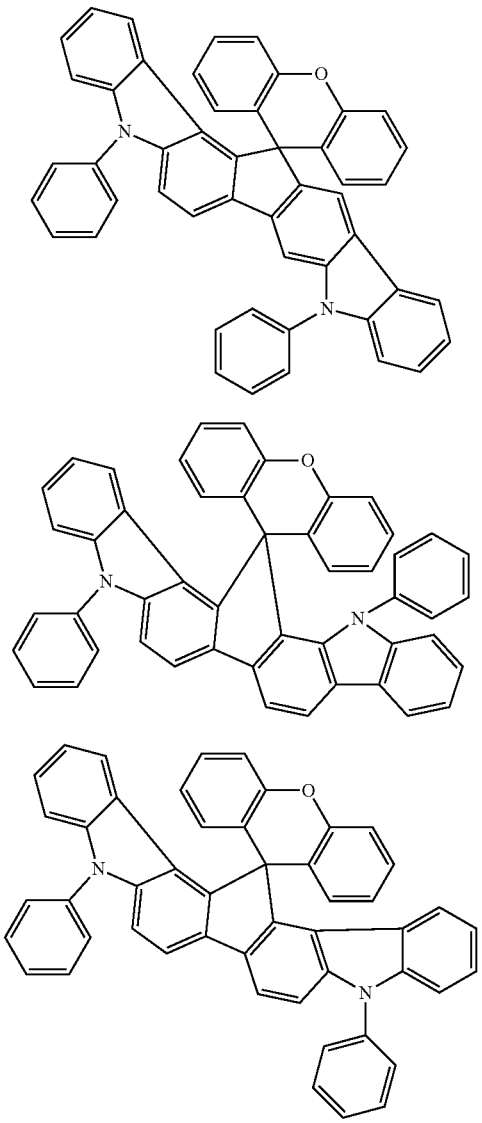
The base structure of the compounds of the invention can be prepared by the route outlined in scheme 1. The Ar group can be introduced according to scheme 2.
Scheme 1:
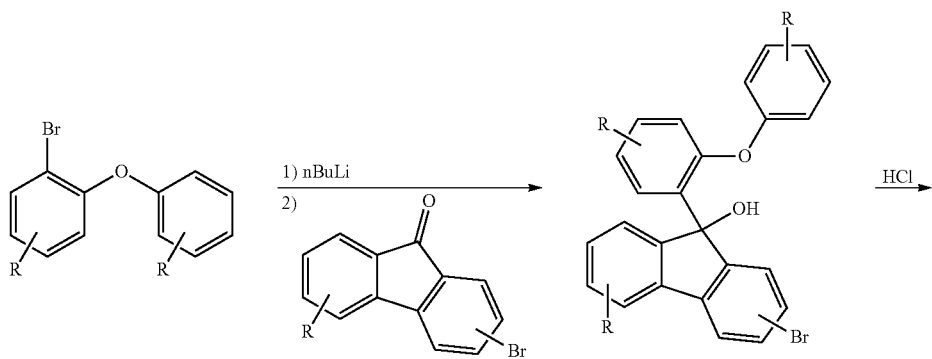

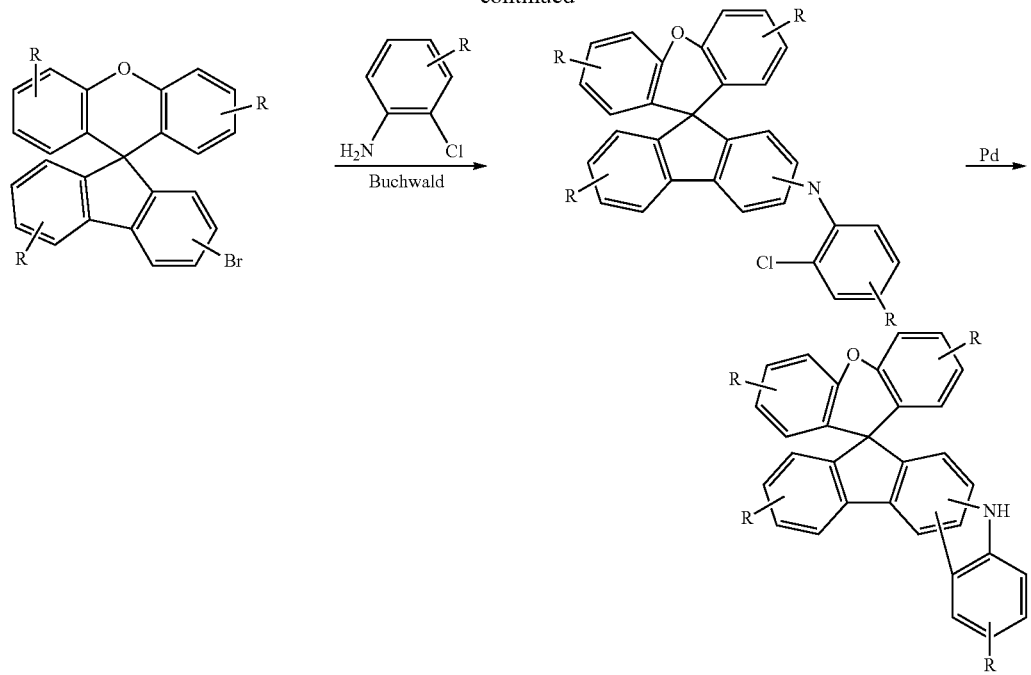

Scheme 2:

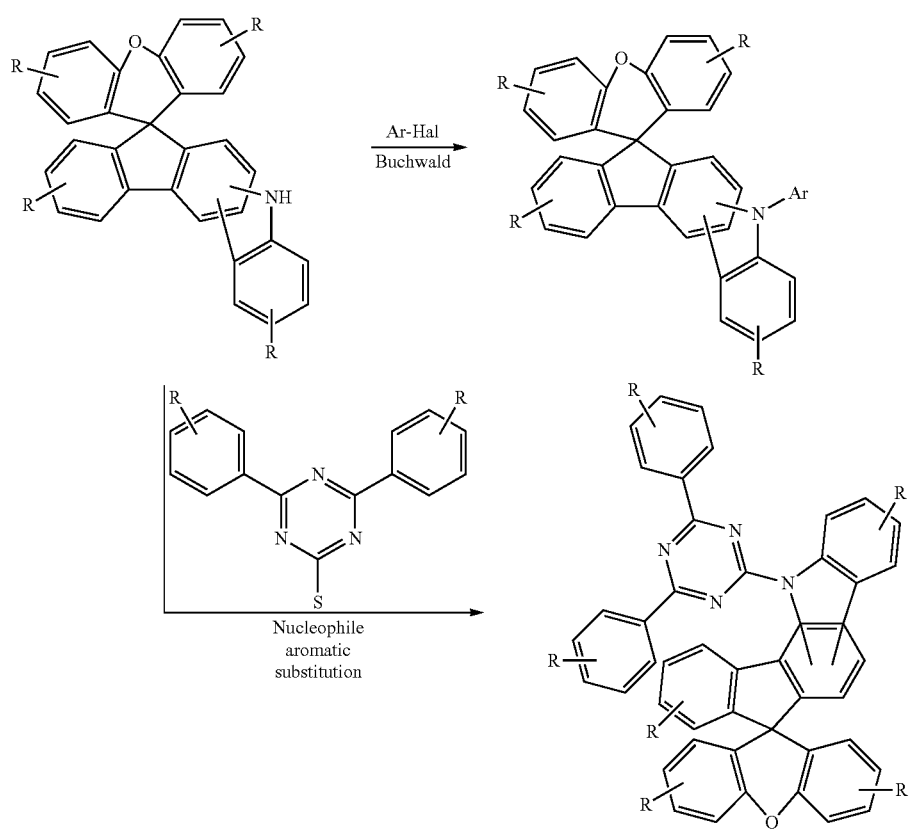

The base skeleton can be synthesized from a halogen-substituted diphenyl ether or analogously with a halogen-substituted diphenyl thioether, which is lithiated and reacted with a halogen-substituted fluorenone, followed by the ring closure reaction to give the corresponding spiro compound under the influence of acid. The latter is reacted with an ortho-haloaminobenzene in a C—N coupling reaction, for example under Pd or Cu catalysis. In the abovementioned reactions, the halogen is preferably Cl, Br or I, especially Br. The ring closure to give the corresponding carbazole derivative is effected by an intramolecular Pd-catalyzed coupling reaction.

Compounds of the formula (1) are obtained by a nucleophilic aromatic substitution reaction or by a Pd-catalyzed coupling reaction, for example a Hartwig-Buchwald coupling or Ullmann coupling, with an Ar group substituted by an appropriate leaving group, especially Cl or Br.

The present invention further provides a process for preparing a compound of formula (1), comprising the reaction steps of:
a) synthesizing the base skeleton of the compound (1) which does not yet contain an Ar group; and
b) converting the base skeleton from a) in a C—N coupling, such as Buchwald coupling or Ullmann coupling, or in a nucleophilic aromatic substitution reaction for introduction of the Ar group.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, or mixtures of these solvents.

The present invention therefore further provides a formulation comprising a compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound and/or a further matrix material. Suitable emitting compounds and further matrix materials are listed at the back in connection with the organic electroluminescent device. This further compound may also be polymeric.

The compounds of the invention are suitable for use in an electronic device, especially in an organic electroluminescent device.

The present invention therefore further provides for the use of a compound of the invention in an electronic device, especially in an organic electroluminescent device.

The present invention still further provides an electronic device comprising at least one compound of the invention. An electronic device in the context of the present invention is a device comprising at least one layer comprising at least one organic compound. This component may also comprise inorganic materials or else layers formed entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitized organic solar cells (DSSCs), organic optical detectors, organic photoreceptors, organic field-quench devices (O-FQDs), light-emitting electrochemical cells (LECs), organic laser diodes (O-lasers) and organic plasmon emitting devices, but preferably organic electroluminescent devices (OLEDs), more preferably phosphorescent OLEDs.

The organic electroluminescent device comprises cathode, anode and at least one emitting layer. Apart from these layers, it may also comprise further layers, for example in each case one or more hole injection layers, hole transport layers, hole blocker layers, electron transport layers, electron injection layers, exciton blocker layers, electron blacker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission (for the basic construction, see, for example, WO 2005/011013). The organic electroluminescent device of the invention may also be a tandem OLED, especially also for white-emitting OLEDs.

The compound of the invention according to the above-detailed embodiments may be used in different layers, according to the exact structure. Preference is given to an organic electroluminescent device comprising a compound of formula (1) or the preferred embodiments detailed above as matrix material for phosphorescent emitters in an emitting layer. In this case, the organic electroluminescent device may contain an emitting layer, or it may contain a plurality of emitting layers, where at least one emitting layer contains at least one compound of the invention as matrix material. In addition, the compound of the invention can also be used in electron transport layer and/or in a hole transport layer and/or in an exciton blocker layer and/or in a hole blocker layer.

When the compound of the invention is used as matrix material for a phosphorescent compound in an emitting layer, it is preferably used in combination with one or more phosphorescent materials (triplet emitters). Phosphorescence in the context of this invention is understood to mean luminescence from an excited state having higher spin multiplicity, i.e. a spin state>1, especially from an excited triplet state. In the context of this application, all luminescent complexes with transition metals or lanthanides, especially all iridium, platinum and copper complexes, shall be regarded as phosphorescent compounds.

The mixture of the compound of the invention and the emitting compound contains between 99% and 1% by volume, preferably between 98% and 10% by volume, more preferably between 97% and 60% by volume and especially between 95% and 80% by volume of the compound of the invention, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

A further preferred embodiment of the present invention is the use of the compound of the invention as matrix material for a phosphorescent emitter in combination with a further matrix material. Suitable matrix materials which can be used in combination with the inventive compounds are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example according to WO 2007/063754 or WO 2008/056746, indenocarbazole derivatives, for example according to WO 2010/136109, WO 2011/000455, WO 2013/041176 or WO 2013/056776, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and WO 2012/143080, or triphenylene derivatives, for example according to WO 2012/048781. It is likewise possible for a further phosphorescent emitter having shorter-wavelength emission than the actual emitter to be present as co-host in the mixture, or a compound not involved in charge transport to a significant extent, if at all, as described, for example, in WO 2010/108579.

Especially suitable in combination with the compound of the invention as co-matrix material are compounds which have a large bandgap and themselves take part at least not to a significant degree, if any at all, in the charge transport of the emitting layer. Such materials are preferably pure hydrocarbons. Examples of such materials can be found, for example, in WO 2009/124627 or in WO 2010/006680.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum.

Examples of the above-described emitters can be found in applications WO 00/70655, WO 2001/41512, WO 2002/02714, WO 2002/15645, EP 1191613, EP 1191612, EP 1191614, WO 2005/033244, WO 2005/019373, US 2005/0258742, WO 2010/086089, WO 2011/044988, WO 2011/157339, WO 2012/007086, WO 2012/163471, WO 2013/000531 and WO 2013/020631, WO 2014/008982, WO 2014/023377. Additionally suitable are, for example, the metal complexes disclosed in the unpublished applications EP 12008582.4, EP 13003484.6, EP 13003485.3, EP 13004552.9, EP 14000345.0 and EP 14000417.7. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

The compounds of the invention are especially also suitable as matrix materials for phosphorescent emitters in organic electroluminescent devices, as described, for example, in WO 98/24271, US 2011/0248247 and US 2012/0223633. In these multicolor display components, an additional blue emission layer is applied by vapor deposition over the full area to all pixels, including those having a color other than blue. It has been found that, surprisingly, the compounds of the invention, when they are used as matrix materials for the red and/or green pixels, still lead to very good emission together with the blue emission layer applied by vapor deposition.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In the further layers of the organic electroluminescent device of the invention, it is possible to use any materials as typically used according to the prior art. The person skilled in the art will therefore be able, without exercising inventive skill, to use any materials known for organic electroluminescent devices in combination with the inventive compounds of formula (1) or the above-recited preferred embodiments.

Additionally preferred is an organic electroluminescent device, characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. It is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example, M. S. Arnold et al., *Appl. Phys. Lett.* 2008, 92, 053301).

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution.

In addition, hybrid methods are possible, in which, for example, one or more layers are applied from solution and one or more further layers are applied by vapor deposition.

These methods are known in general terms to those skilled in the art and can be applied by those skilled in the art without exercising inventive skill to organic electroluminescent devices comprising the compounds of the invention.

The compounds of the invention and the organic electroluminescent devices of the invention are notable for one or more of the following surprising advantages over the prior art:
1. The compounds of the invention, used as matrix material for phosphorescent emitters, lead to long lifetimes.
2. The compounds of the invention lead to high efficiencies. This is especially true when the compounds are used as matrix material for a phosphorescent emitter.
3. The compounds of the invention lead to low operating voltages. This is especially true when the compounds are used as matrix material for a phosphorescent emitter.

These abovementioned advantages are not accompanied by a deterioration in the further electronic properties.

The invention is illustrated in detail by the examples which follow, without any intention of restricting it thereby. The person skilled in the art will be able to use the information given to execute the invention over the entire scope disclosed and to prepare further compounds of the invention without exercising inventive skill and to use them in electronic devices or to employ the process of the invention.

Examples:

The syntheses which follow, unless stated otherwise, are conducted under a protective gas atmosphere in dried solvents. The solvents and reagents can be purchased from ALDRICH or ABCR. The numbers given for the reactants that are not commercially available are the corresponding CAS numbers.

a) Spiro[2-bromo-9H-fluorene-9,9'-(9H)-xanthene]

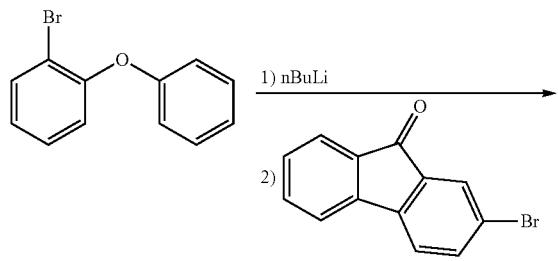

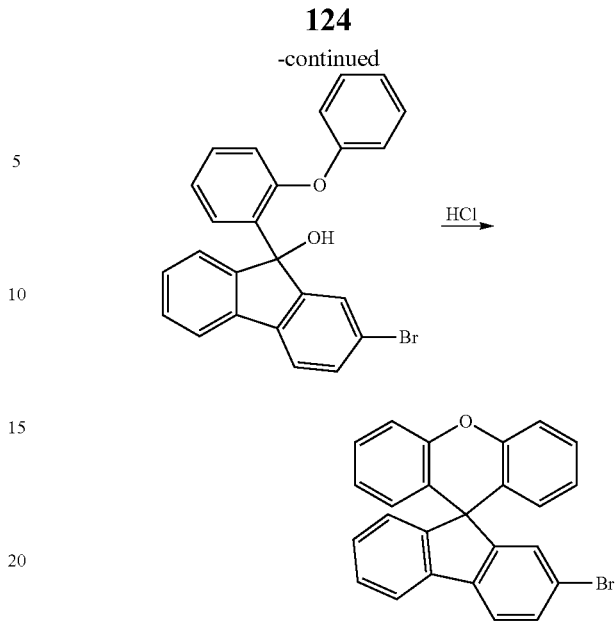

31.7 g (127 mmol) of 1-bromo-2-diphenyl ether are dissolved in a baked-out flask in 400 mL of dried THF. The reaction mixture is cooled to −78° C. At this temperature, 55 mL of a 2.5 M solution of n-butyllithium in hexane (127 mmol) are slowly added dropwise. The mixture is stirred at −70° C. for a further 1 h. Subsequently, 30 g of 2-bromo-fluorenone (116 mmol) are dissolved in 100 mL of THF and added dropwise at −70° C. After the addition has ended, the reaction mixture is left to warm up gradually to room temperature, quenched with NH$_4$Cl and then concentrated on a rotary evaporator. The concentrated solution is admixed cautiously with 300 mL of acetic acid. Subsequently, 50 mL of fuming HCl are added. The mixture is heated to 75° C. for 6 h. During this time, a white solid precipitates out. The mixture is then left to cool to room temperature, and the precipitated solid is filtered off with suction and washed with methanol. Yield: 45 g (95%)

The following compounds are prepared in an analogous manner:

| | Reactant 1 | Reactant 2 | Product | Yield |
|---|---|---|---|---|
| a1 | | | | 77% |
| a2 | | | | 65% |

| Reactant 1 | Reactant 2 | Product | Yield |
|---|---|---|---|
| a3 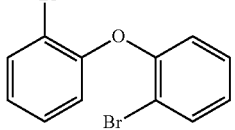 | 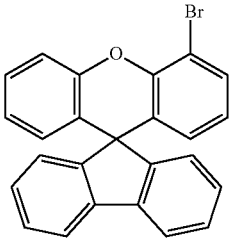 [SMILES: Brc1cccc2c1Oc1ccccc1C21c2ccccc2-c2ccccc21] | 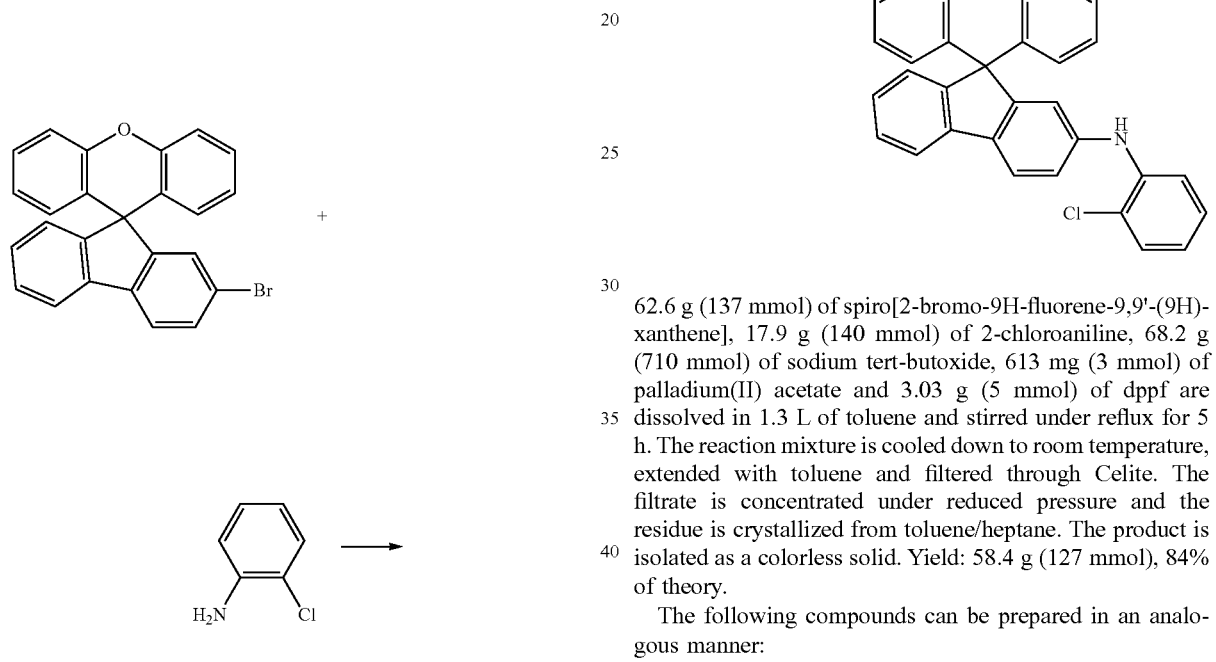 | 73% | b) 2-Chlorophenyl-4-spiro-[9H-fluorene-9,9'-(9H)-xanthenylamine

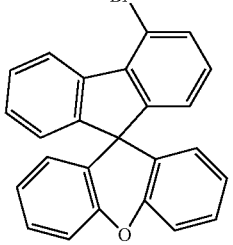

62.6 g (137 mmol) of spiro[2-bromo-9H-fluorene-9,9'-(9H)-xanthene], 17.9 g (140 mmol) of 2-chloroaniline, 68.2 g (710 mmol) of sodium tert-butoxide, 613 mg (3 mmol) of palladium(II) acetate and 3.03 g (5 mmol) of dppf are dissolved in 1.3 L of toluene and stirred under reflux for 5 h. The reaction mixture is cooled down to room temperature, extended with toluene and filtered through Celite. The filtrate is concentrated under reduced pressure and the residue is crystallized from toluene/heptane. The product is isolated as a colorless solid. Yield: 58.4 g (127 mmol), 84% of theory.

The following compounds can be prepared in an analogous manner:

| Reactant 1 | Reactant 2 | Product | Yield |
|---|---|---|---|
| b1 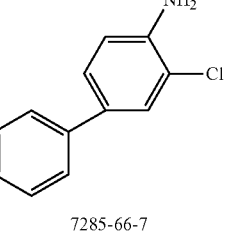 | 7285-66-7 | | 80% |

-continued
| Reactant 1 | Reactant 2 | Product | Yield |
|---|---|---|---|
| b2 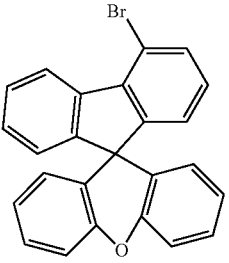 [SMILES: Brc1cccc2c1-c1ccccc1C21c2ccccc2Oc2ccccc21] | 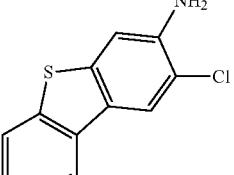 858426-71-8 | 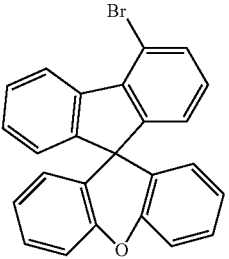 [SMILES: Brc1cccc2c1-c1ccccc1C21c2ccccc2Oc2ccccc21] | 73% |
| b3 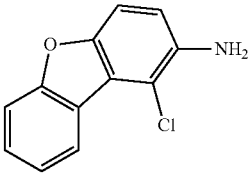 | 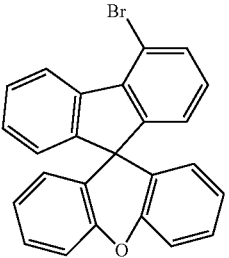 [SMILES: Brc1cccc2c1-c1ccccc1C21c2ccccc2Oc2ccccc21] 133617-97-7 | 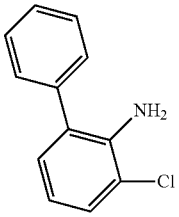 | 64% |
| b4 | | | 56% |

-continued

| Reactant 1 | Reactant 2 | Product | Yield |
|---|---|---|---|
| b5 | 5833-88-5 | | 69% |
| b6 | | | 64% |
| b7 | | | 60% |
| b8 | | | 64% | c) Cyclization

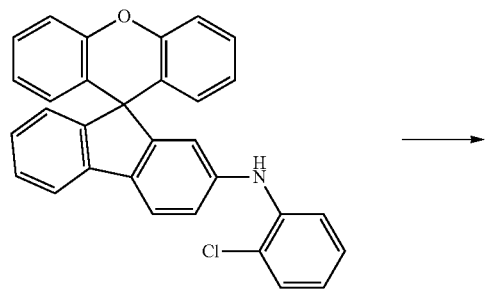

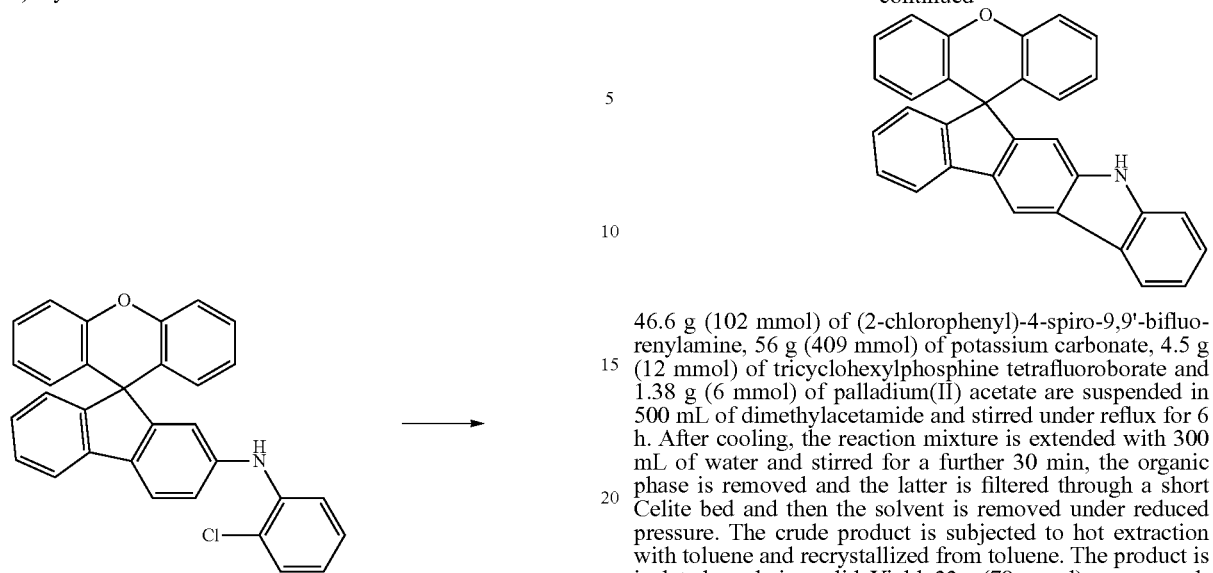

46.6 g (102 mmol) of (2-chlorophenyl)-4-spiro-9,9'-bifluorenylamine, 56 g (409 mmol) of potassium carbonate, 4.5 g (12 mmol) of tricyclohexylphosphine tetrafluoroborate and 1.38 g (6 mmol) of palladium(II) acetate are suspended in 500 mL of dimethylacetamide and stirred under reflux for 6 h. After cooling, the reaction mixture is extended with 300 mL of water and stirred for a further 30 min, the organic phase is removed and the latter is filtered through a short Celite bed and then the solvent is removed under reduced pressure. The crude product is subjected to hot extraction with toluene and recrystallized from toluene. The product is isolated as a beige solid. Yield: 33 g (78 mmol), corresponding to 77% of theory.

The following compounds can be prepared in an analogous manner:

| | Reactant | Product | Yield |
|---|---|---|---|
| c1 | 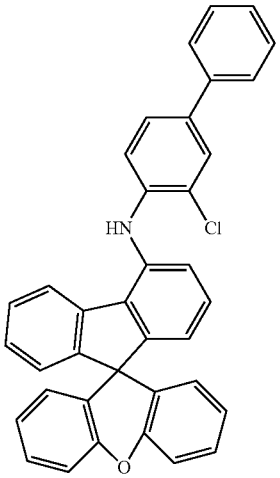 [SMILES: Clc1cc(-c2ccccc2)ccc1Nc1cccc2c1-c1ccccc1C21c2ccccc2Oc2ccccc21] | 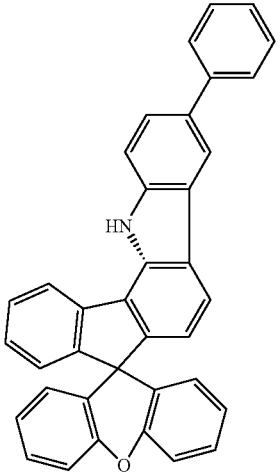 | 71% |
| c2 | 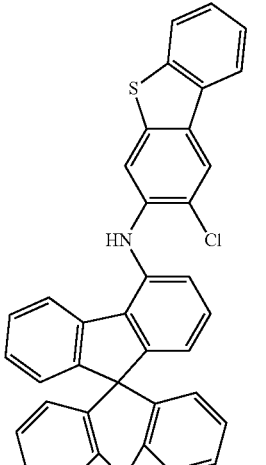 | 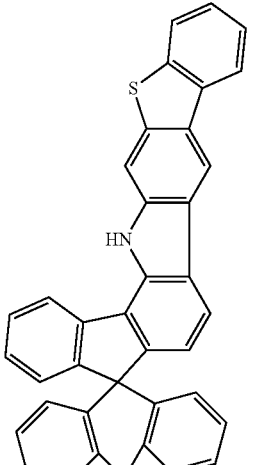 | 78% |

-continued

| Reactant | Product | Yield |
|---|---|---|
| c3 | | 73% |
| c4 | | 70% |
| c5 | | 69% |
| c6 | | 58% |

-continued
| Reactant | Product | Yield |
|---|---|---|
| c7 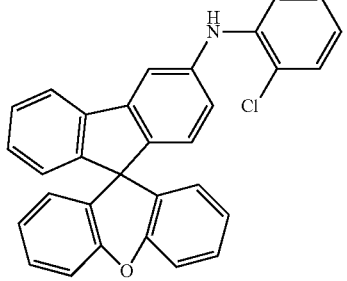 | 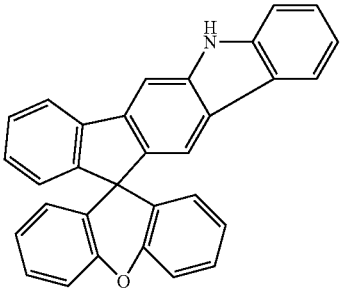 [SMILES: c1ccc2c(c1)Oc1ccccc1C21c2ccccc2-c2cc3[nH]c4ccccc4c3cc21] | 60% |
| | | 30% |
| c8 | | 76% |
d) Nucleophilic Aromatic Substitution
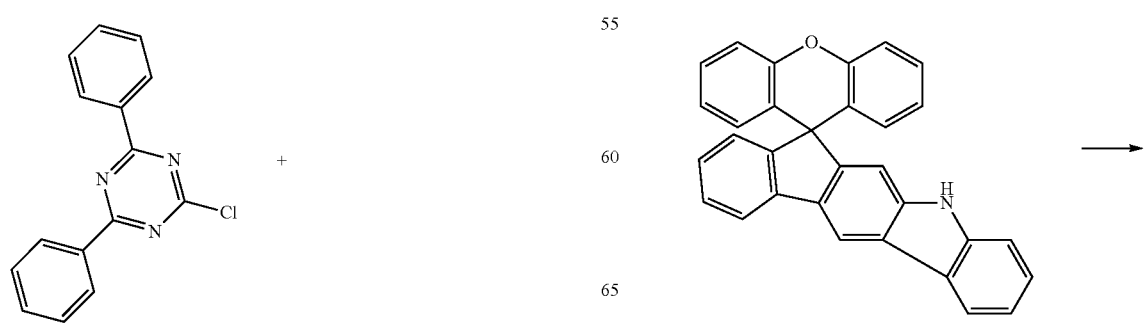
-continued -continued

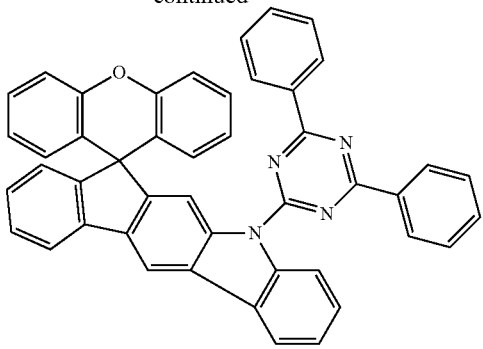

4.2 g of 60% NaH in mineral oil (106 mmol) are dissolved in 300 mL of dimethylformamide under a protective atmosphere. 46 g (106 mmol) of indeno[1,2-a]carbazole derivative (from c) are dissolved in 250 mL of DMF and added dropwise to the reaction mixture. After 1 h at room temperature, a solution of 2-chloro-4,6-diphenyl-[1,3,5]-triazine (34.5 g, 122 mmol) in 200 mL of THF is added dropwise. The reaction mixture is stirred at room temperature for 12 h. After this time, the reaction mixture is poured onto ice. After warming to room temperature, the solids that precipitate out are filtered and washed with ethanol and heptane. The residue is subjected to hot extraction with toluene, recrystallized from toluene/n-heptane and finally sublimed under high vacuum. The purity is 99.9%. Yield of product d: 30 g (46 mmol), corresponding to 43% of theory.

The following compounds can be prepared in an analogous manner:

| | Reactant 1 | Reactant 2 | Product | Yield |
|---|---|---|---|---|
| 1d | | 3842-55-5 | | 40% |
| 2d | | 1384480-21-0 | | 39% |
| 3d | | | | 44% |

-continued

| Reactant 1 | Reactant 2 | Product | Yield |
|---|---|---|---|
| 4d | | | 31% |
| 5d | | | 43% |
| 6d | | 2915-16-4 | 41% |

| Reactant 1 | Reactant 2 | Product | Yield |
|---|---|---|---|
| 7d 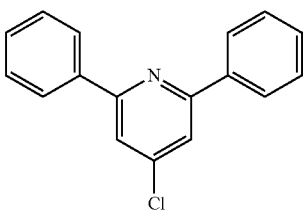 [SMILES: Clc1nc(-c2ccccc2)nc(-c2ccccc2)n1] | 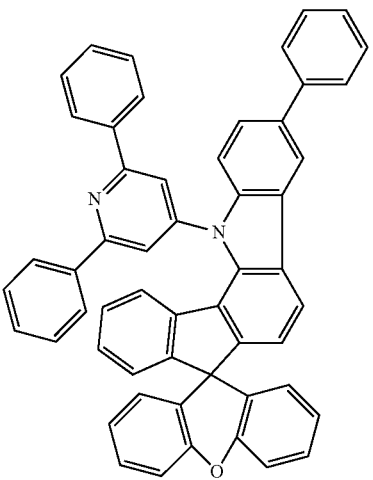 [SMILES: c1ccc(-c2ccc3c(c2)c2ccc4c(c2n3-c2cc(-c3ccccc3)nc(-c3ccccc3)c2)-c2ccccc2C42c3ccccc3Oc3ccccc32)cc1]
133785-60-1 | 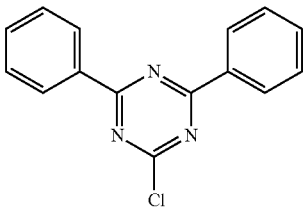 [SMILES: Clc1nc(-c2ccccc2)nc(-c2ccccc2)n1] | 39% |
| 8d 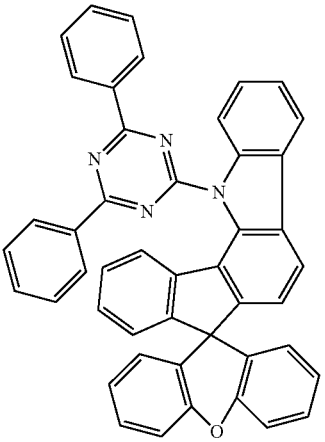 | 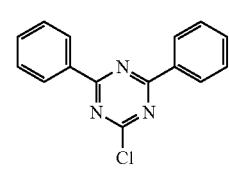 [SMILES: Clc1nc(-c2ccccc2)nc(-c2ccccc2)n1] | 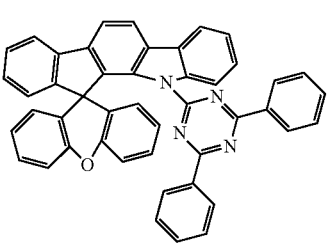 [SMILES: c1ccc(-c2nc(-c3ccccc3)nc(-n3c4ccccc4c4ccc5c(c43)C3(c4ccccc4Oc4ccccc43)c3ccccc3-5)n2)cc1] | 46% |
| 9d | | | 40% |

| Reactant 1 | Reactant 2 | Product | Yield |
|---|---|---|---|
| 10d 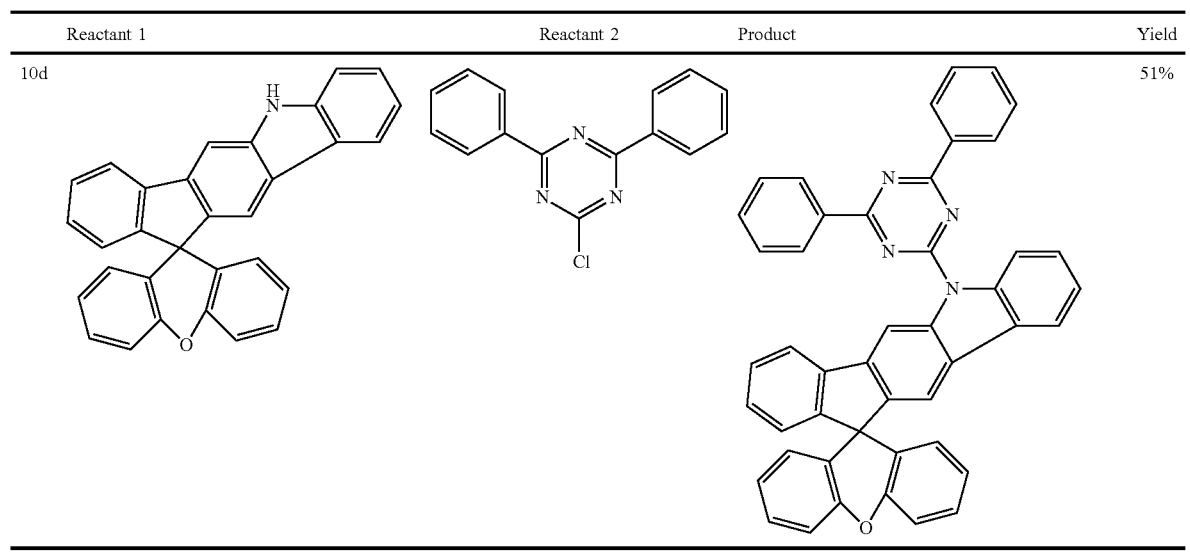 | | | 51% | e) Buchwald Reaction

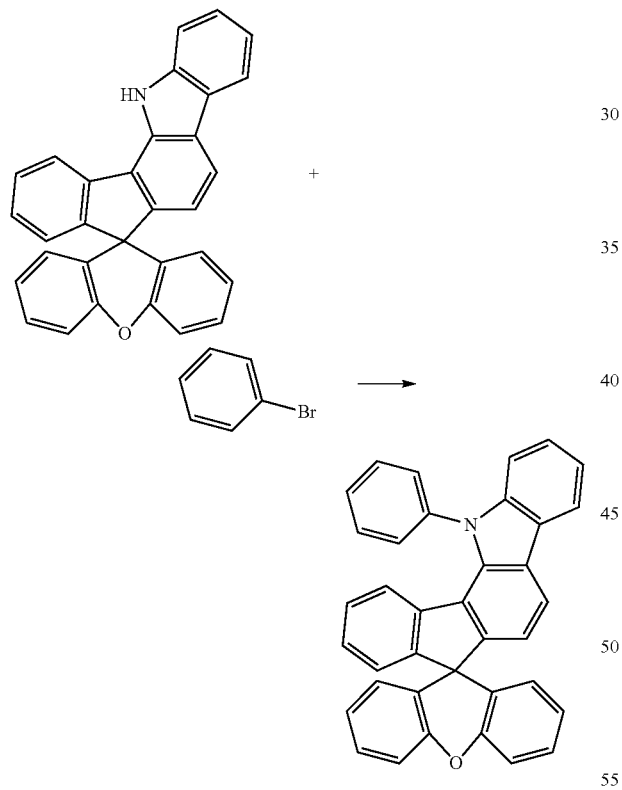

44.6 g (106 mmol) of indeno[1,2-a]carbazole derivative (from c), 17.9 g (114 mmol) of bromobenzene and 30.5 g of NaOtBu are suspended in 1.5 L of p-xylene. To this suspension are added 0.5 g (2.11 mmol) of Pd(OAc)$_2$ and 1.6 mL of a 1M tri-tert-butylphosphine solution. The reaction mixture is heated under reflux for 16 h. After cooling, the organic phase is removed, washed three times with 200 mL of water and then concentrated to dryness. The residue is subjected to hot extraction with toluene, recrystallized from toluene and finally sublimed under high vacuum. The purity is 99.9% with a yield of product e of 22.6 g (45 mmol; 43%).

The following compounds can be prepared in an analogous manner:

| Reactant 1 | Reactant 2 | Product | Yield |
|---|---|---|---|
| 1e 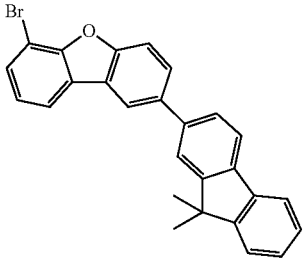 | 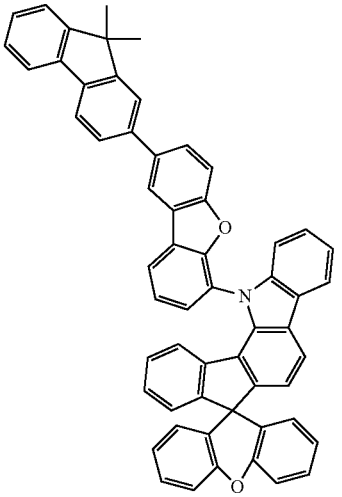 [SMILES: CC1(C)c2ccccc2-c2ccc(-c3ccc4oc5c(-n6c7ccccc7c7ccc8c(c76)-c6ccccc6C86c7ccccc7Oc7ccccc76)cccc5c4c3)cc21] [1010088-04-1] | 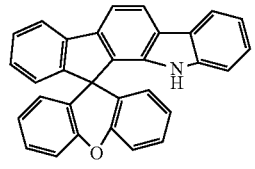 [SMILES: c1ccc2c(c1)Oc1ccccc1C21c2ccccc2-c2ccc3c([nH]c4ccccc43)c21] | 39% |
| 2e 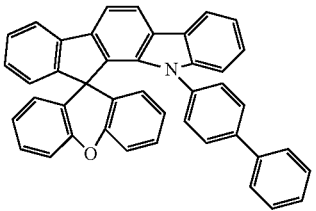 [SMILES: c1ccc(-c2ccc(-n3c4ccccc4c4ccc5c(c43)C3(c4ccccc4Oc4ccccc43)c3ccccc3-5)cc2)cc1] | Br—C6H4—C6H5 92-66-0 | 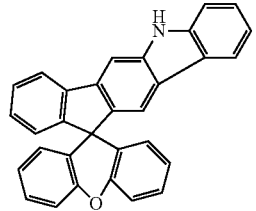 [SMILES: c1ccc2c(c1)Oc1ccccc1C21c2ccccc2-c2cc3[nH]c4ccccc4c3cc21] | 41% |
| 3e 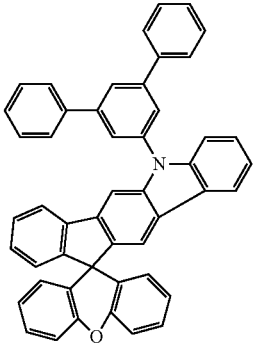 [SMILES: c1ccc(-c2cc(-c3ccccc3)cc(-n3c4ccccc4c4cc5c(cc43)-c3ccccc3C53c4ccccc4Oc4ccccc43)c2)cc1] | 103068-20-8 | 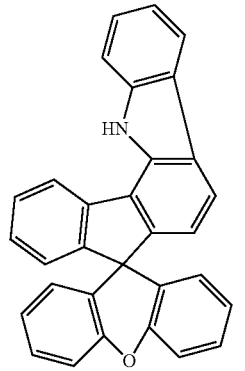 [SMILES: c1ccc2c(c1)Oc1ccccc1C21c2ccccc2-c2c1ccc1c2[nH]c2ccccc21] | 42% |
| 4e 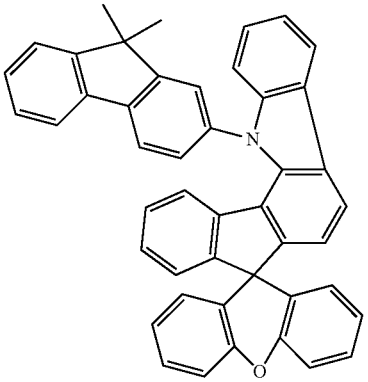 [SMILES: CC1(C)c2ccccc2-c2ccc(-n3c4ccccc4c4ccc5c(c43)-c3ccccc3C53c4ccccc4Oc4ccccc43)cc21] | 28320-31-2 | | 34% |

-continued
| | Reactant 1 | Reactant 2 | Product | Yield |
|---|---|---|---|---|
| 5e | 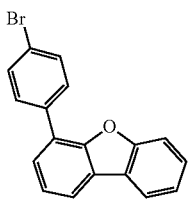 | 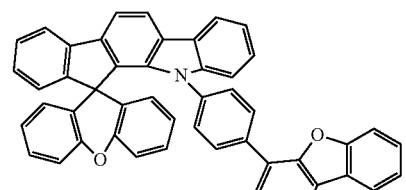 [955959-84-9] | 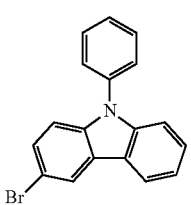 | 45% |
| 6e | 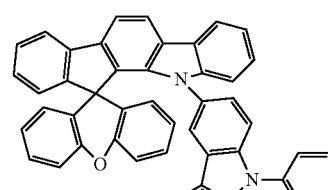 | 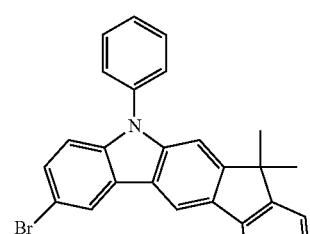 [1153-85-1] | 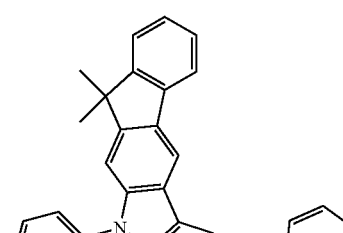 | 42% |
| 7e | 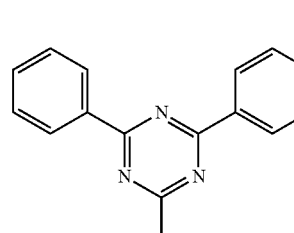 | 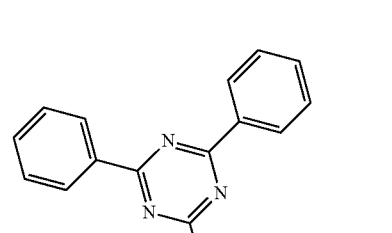 [1257220-44-2] |  | 40% |
| 8e |  |  864377-31-1] |  | 47% |

Example: Production of the OLEDs

In examples C1 to I11 which follow (see tables 1 and 2), the data of various OLEDs are presented. Cleaned glass plaques (cleaning in laboratory glass washer, Merck Extran detergent) coated with structured ITO (indium tin oxide) of thickness 50 nm are pretreated with UV ozone for 25 min (PR-100 UV ozone generator from UVP) and, for improved processing, coated with 20 nm of PEDOT:PSS (poly(3,4-ethylenedioxythiophene) poly(styrenesulfonate), purchased as CLEVIOS™ P VP AI 4083 from Heraeus Precious Metals GmbH Deutschland, spun on from aqueous solution) and then baked at 180° C. for 10 min. These coated glass plaques form the substrates to which the OLEDs are applied.

The OLEDs basically have the following layer structure: substrate/hole transport layer (HTL)/optional interlayer (IL)/ electron blocker layer (EBL)/emission layer (EML)/optional hole blocker layer (HBL)/electron transport layer (ETL)/ optional electron injection layer (EIL) and finally a cathode. The cathode is formed by an aluminum layer of thickness 100 nm. The exact structure of the OLEDs can be found in table 1. A reference such as "e" or "6e" in table 1 relates to the corresponding materials shown in table 3. The further materials required for production of the OLEDs are shown in table 3.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as IC2:6e:TEG1 (40%:50%:10%) mean here that the material IC2 is present in the layer in a proportion by volume of 40%, 6e in a proportion of 40% and TEG1 in a proportion of 10%. Analogously, the electron transport layer may also consist of a mixture of two materials.

The OLEDs are characterized in a standard manner. For this purpose, the electroluminescence spectra, the current efficiency (measured in cd/A), the power efficiency (measured in lm/W) and the external quantum efficiency (EQE, measured in percent) are determined as a function of luminance, calculated from current-voltage-luminance characteristics (IUL characteristics) assuming Lambertian radiation characteristics. The electroluminescence spectra are determined at a luminance of 1000 cd/m$^2$, and the CIE 1931 x and y color coordinates are calculated therefrom. The parameter U1000 in Table 2 refers to the voltage which is required for a luminance of 1000 cd/m$^2$. CE1000 and PE1000 respectively refer to the current and power efficiencies which are achieved at 1000 cd/m$^2$. Finally, EQE1000 refers to the external quantum efficiency at an operating luminance of 1000 cd/m$^2$.

The data for the various OLEDs are collated in Table 2. Examples C1-C5 are comparative examples according to the prior art; examples I1-I11 show data of OLEDs comprising inventive materials.

Some of the examples are elucidated in detail hereinafter, in order to illustrate the advantages of the compounds of the invention.

Use of Compounds of the Invention as Electron Transport Materials

Through the use of compounds of the invention in the electron transport layer of OLEDs, it is possible to achieve distinct increases in terms of operating voltage, external quantum efficiency and hence in particular power efficiency as well. In this regard, see examples C1, C2 and I1-I3.

Use of Compounds of the Invention as Matrix Materials in Phosphorescent OLEDs

The materials of the invention, when used as matrix materials in phosphorescent OLEDs, give significant improvements compared to the prior art. With the compounds 6d, 1d, 8e, for example, much lower operating voltage and higher efficiency are obtained than with the compounds PA1 and PA2. In this regard, see examples C3, C4 and I9-I11.

In addition, compounds of the invention can achieve improvements in the case of mixing with a second matrix material. Compared to the compound PA3 which, in combination with IC2, already gives very good performance data, an improvement is obtained through the use of the compounds e and 6e. In this regard, see examples C5, I5 and I6.

TABLE 1

| | | | | | | | |
|---|---|---|---|---|---|---|---|
| | | | | Structure of the OLEDs | | | |
| Ex. | HTL thickness | IL thickness | EBL thickness | EML thickness | HBL thickness | ETL thickness | EIL thickness |
| C1 | SpA1 70 nm | HATCN 5 nm | SpMA1 90 nm | IC1:TEG1 (90%:10%) 30 nm | — | PA1 40 nm | LiQ 4 nm |
| C2 | SpA1 70 nm | HATCN 5 nm | SpMA1 90 nm | IC1:TEG1 (90%:10%) 30 nm | — | PA2 40 nm | LiQ 4 nm |
| C3 | SpA1 70 nm | HATCN 5 nm | SpMA1 90 nm | PA1:TEG1 (90%:10%) 30 nm | — | ST2:LiQ (50%:50%) 40 nm | — |
| C4 | SpA1 70 nm | HATCN 5 nm | SpMA1 90 nm | PA2:TEG1 (90%:10%) 30 nm | IC1 10 nm | ST2:LiQ (50%:50%) 30 nm | — |
| C5 | SpA1 70 nm | HATCN 5 nm | SpMA1 90 nm | IC2:PA3:TEG1 (40%:50%:10%) 30 nm | IC1 10 nm | ST2:LiQ (50%:50%) 30 nm | — |
| I1 | SpA1 70 nm | HATCN 5 nm | SpMA1 90 nm | IC1:TEG1 (90%:10%) 30 nm | — | d 40 nm | LiQ 4 nm |
| I2 | SpA1 70 nm | HATCN 5 nm | SpMA1 90 nm | IC1:TEG1 (90%:10%) 30 nm | — | 9d 40 nm | LiQ 4 nm |
| I3 | SpA1 70 nm | HATCN 5 nm | SpMA1 90 nm | IC1:TEG1 (90%:10%) 30 nm | — | 8e 40 nm | LiQ 4 nm |
| I4 | SpA1 90 nm | HATCN 5 nm | SpMA1 130 nm | d:TER1 (92%:8%) 40 nm | — | ST2:LiQ (50%:50%) 40 nm | — |
| I5 | SpA1 70 nm | HATCN 5 nm | SpMA1 90 nm | IC2:e:TEG1 (40%:50%:10%) 30 nm | IC1 10 nm | ST2:LiQ (50%:50%) 30 nm | — |
| I6 | SpA1 70 nm | HATCN 5 nm | SpMA1 90 nm | IC2:6e:TEG1 (40%:50%:10%) 30 nm | IC1 10 nm | ST2:LiQ (50%:50%) 30 nm | — |

TABLE 1-continued

Structure of the OLEDs

| Ex. | HTL thickness | IL thickness | EBL thickness | EML thickness | HBL thickness | ETL thickness | EIL thickness |
|---|---|---|---|---|---|---|---|
| I7 | SpA1 70 nm | HATCN 5 nm | SpMA1:5e (85%:15%) 90 nm | IC1:TEG1 (90%:10%) 30 nm | IC1 10 nm | ST2:LiQ (50%:50%) 30 nm | — |
| I8 | SpA1 70 nm | HATCN 5 nm | SpMA1 90 nm | 10d:BIC1:TEG1 (55%:40%:5%) 30 nm | IC1 10 nm | ST2:LiQ (50%:50%) 30 nm | — |
| I9 | SpA1 70 nm | HATCN 5 nm | SpMA1 90 nm | 6d:TEG1 (90%:10%) 30 nm | — | ST2:LiQ (50%:50%) 40 nm | — |
| I10 | SpA1 70 nm | HATCN 5 nm | SpMA1 90 nm | 1d:TEG1 (90%:10%) 30 nm | — | ST2:LiQ (50%:50%) 40 nm | — |
| I11 | SpA1 70 nm | HATCN 5 nm | SpMA1 90 nm | 8e:TEG1 (90%:10%) 30 nm | IC1 10 nm | ST2:LiQ (50%:50%) 30 nm | — |

TABLE 2

Data of the OLEDs

| Ex. | U1000 (V) | CE1000 (cd/A) | PE1000 (lm/W) | EQE 1000 | CIE x/y at 1000 cd/m$^2$ |
|---|---|---|---|---|---|
| C1 | 3.6 | 51 | 45 | 14.5% | 0.34/0.62 |
| C2 | 3.8 | 54 | 44 | 15.2% | 0.33/0.62 |
| C3 | 3.5 | 51 | 46 | 14.3% | 0.33/0.62 |
| C4 | 3.7 | 56 | 48 | 15.7% | 0.33/0.62 |
| C5 | 3.3 | 59 | 55 | 16.2% | 0.33/0.62 |
| I1 | 3.0 | 58 | 61 | 16.3% | 0.34/0.62 |
| I2 | 3.4 | 56 | 52 | 15.6% | 0.33/0.63 |
| I3 | 3.2 | 60 | 59 | 17.0% | 0.33/0.62 |
| I4 | 4.1 | 12.1 | 9.4 | 13.1% | 0.67/0.33 |
| I5 | 3.2 | 61 | 59 | 17.2% | 0.34/0.61 |
| I6 | 3.3 | 65 | 63 | 18.2% | 0.34/0.62 |
| I7 | 3.6 | 59 | 52 | 16.7% | 0.34/0.62 |
| I8 | 3.3 | 60 | 57 | 16.6% | 0.33/0.62 |
| I9 | 3.4 | 67 | 61 | 18.6% | 0.33/0.62 |
| I10 | 3.2 | 61 | 60 | 17.1% | 0.34/0.62 |
| I11 | 3.2 | 59 | 57 | 16.5% | 0.33/0.62 |

TABLE 2

Structural formulae of the materials for the OLEDs

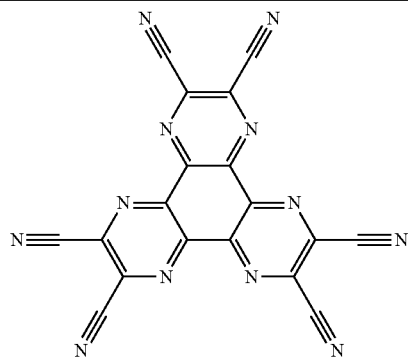

HATCN

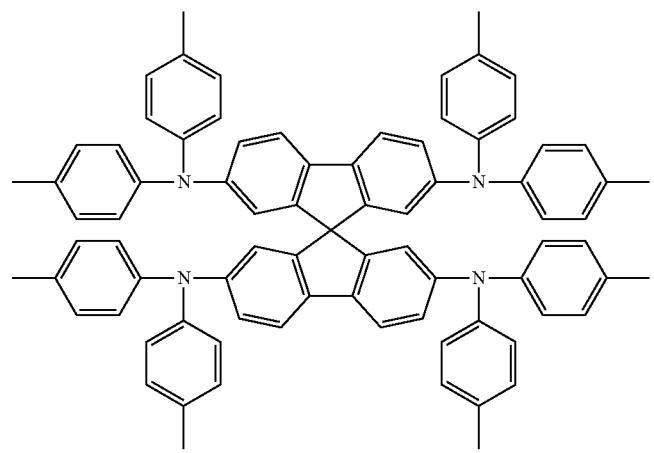

SpA1

TABLE 2-continued
Structural formulae of the materials for the OLEDs
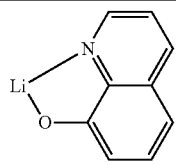 LiQ
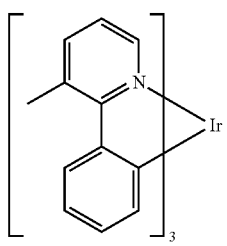 TEG1
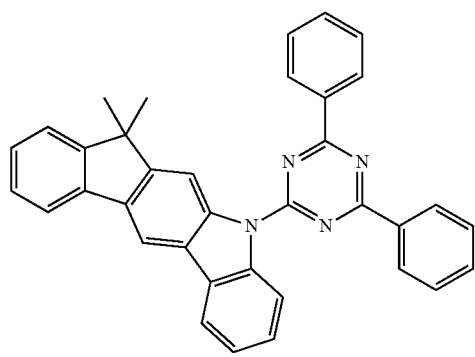 [SMILES: CC1(C)c2ccccc2-c2cc3c4ccccc4n(-c4nc(-c5ccccc5)nc(-c5ccccc5)n4)c3cc21] IC1
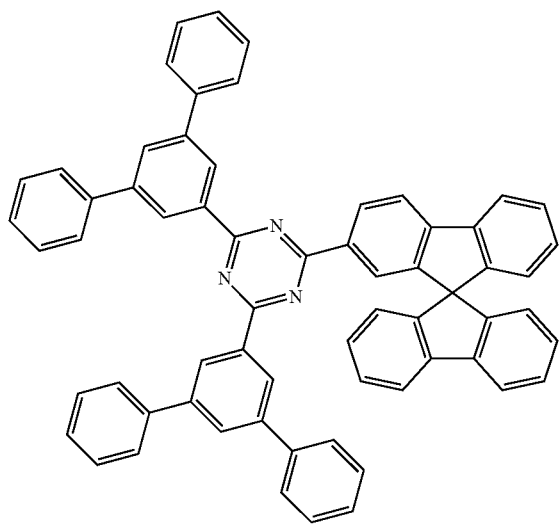 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1] ST2

TABLE 2-continued
Structural formulae of the materials for the OLEDs
SpMA1
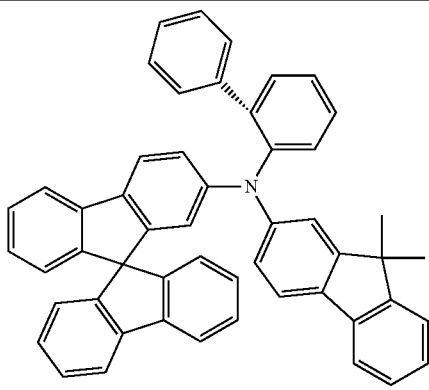
TER1
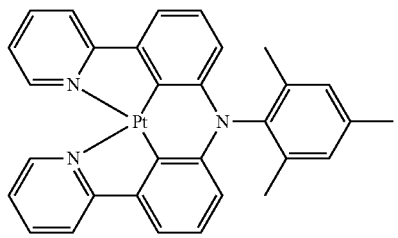
IC2
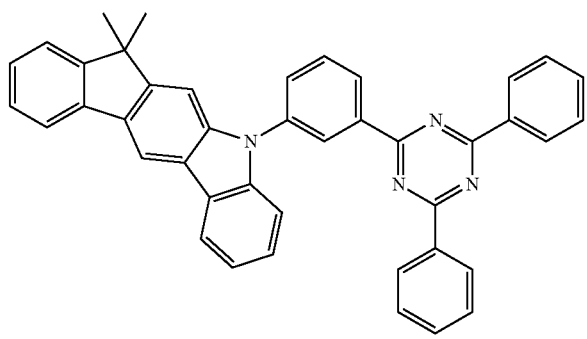 [SMILES: CC1(C)c2ccccc2-c2cc3c4ccccc4n(-c4cccc(-c5nc(-c6ccccc6)nc(-c6ccccc6)n5)c4)c3cc21]
BIC1
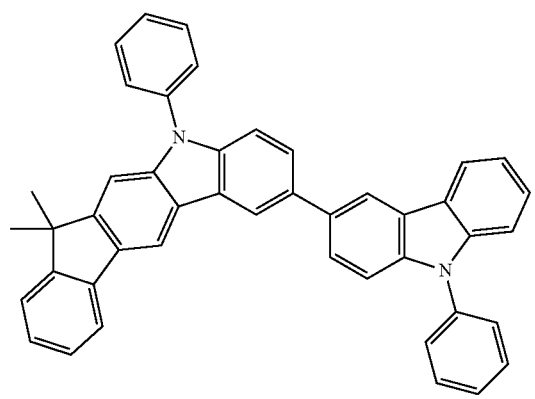 [SMILES: CC1(C)c2ccccc2-c2cc3c4cc(-c5ccc6c(c5)c5ccccc5n6-c5ccccc5)ccc4n(-c4ccccc4)c3cc21]

TABLE 2-continued
Structural formulae of the materials for the OLEDs
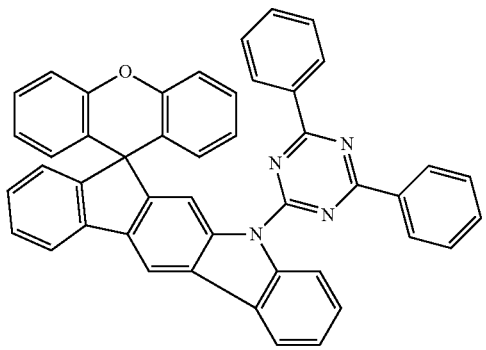 [SMILES: c1ccc(-c2nc(-c3ccccc3)nc(-n3c4ccccc4c4cc5c(cc43)C3(c4ccccc4Oc4ccccc43)c3ccccc3-5)n2)cc1]
d
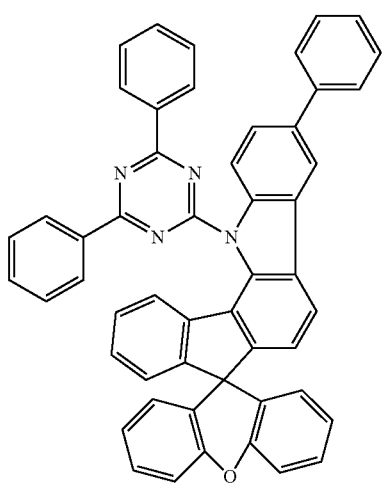 [SMILES: c1ccc(-c2ccc3c(c2)c2ccc4c(c2n3-c2nc(-c3ccccc3)nc(-c3ccccc3)n2)-c2ccccc2C42c3ccccc3Oc3ccccc32)cc1]
1d
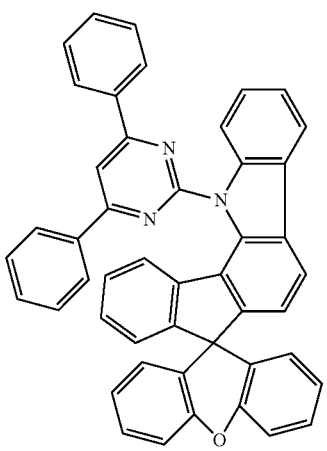 [SMILES: c1ccc(-c2cc(-c3ccccc3)nc(-n3c4ccccc4c4ccc5c(c43)-c3ccccc3C53c4ccccc4Oc4ccccc43)n2)cc1]
6d
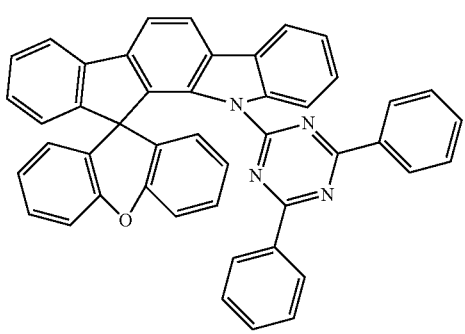 [SMILES: c1ccc(-c2nc(-c3ccccc3)nc(-n3c4ccccc4c4ccc5c(c43)C3(c4ccccc4Oc4ccccc43)c3ccccc3-5)n2)cc1]
9d TABLE 2-continued
Structural formulae of the materials for the OLEDs
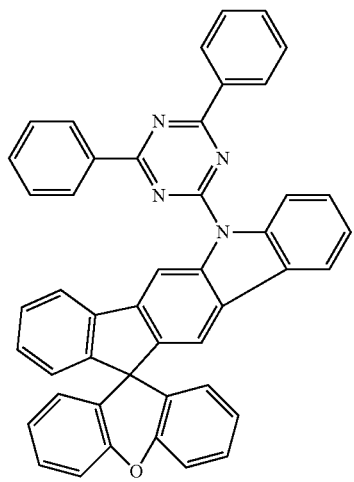 [SMILES: c1ccc(-c2nc(-c3ccccc3)nc(-n3c4ccccc4c4cc5c(cc43)-c3ccccc3C53c4ccccc4Oc4ccccc43)n2)cc1]
10d
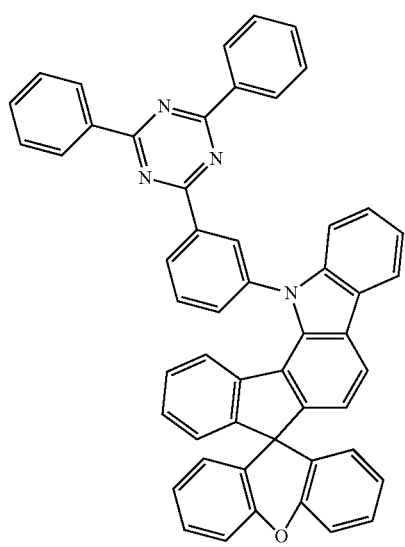 [SMILES: c1ccc(-c2nc(-c3ccccc3)nc(-c3cccc(-n4c5ccccc5c5ccc6c(c54)-c4ccccc4C64c5ccccc5Oc5ccccc54)c3)n2)cc1]
8e
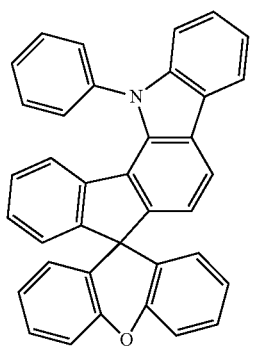 [SMILES: c1ccc(-n2c3ccccc3c3ccc4c(c32)-c2ccccc2C42c3ccccc3Oc3ccccc32)cc1]
e TABLE 2-continued
Structural formulae of the materials for the OLEDs
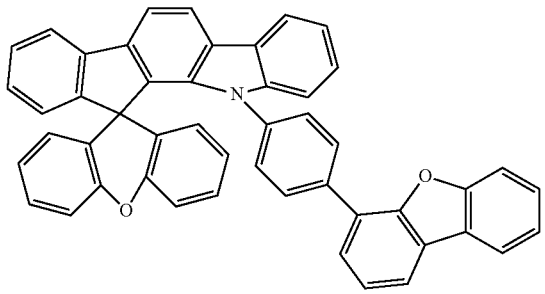 [SMILES: c1ccc2c(c1)Oc1ccccc1C21c2ccccc2-c2ccc3c4ccccc4n(-c4ccc(-c5cccc6c5oc5ccccc56)cc4)c3c21]
5e
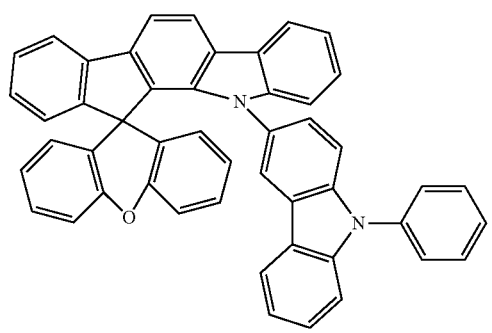 [SMILES: c1ccc(-n2c3ccccc3c3cc(-n4c5ccccc5c5ccc6c(c54)C4(c5ccccc5Oc5ccccc54)c4ccccc4-6)ccc32)cc1]
6e
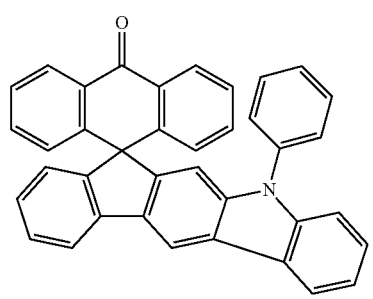 [SMILES: O=C1c2ccccc2C2(c3ccccc31)c1ccccc1-c1cc3c4ccccc4n(-c4ccccc4)c3cc12]
PA1
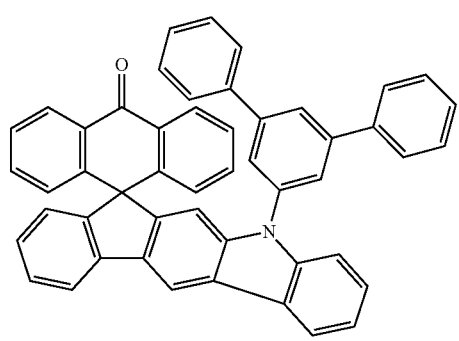 [SMILES: O=C1c2ccccc2C2(c3ccccc31)c1ccccc1-c1cc3c4ccccc4n(-c4cc(-c5ccccc5)cc(-c5ccccc5)c4)c3cc12]
PA2

TABLE 2-continued

Structural formulae of the materials for the OLEDs

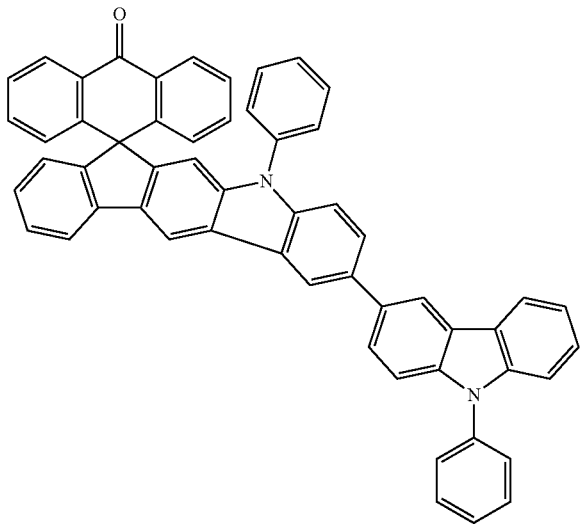 [SMILES: O=C1c2ccccc2C2(c3ccccc31)c1ccccc1-c1cc3c4cc(-c5ccc6c(c5)c5ccccc5n6-c5ccccc5)ccc4n(-c4ccccc4)c3cc12]

PA3

The invention claimed is:

1. A compound of formula (1)

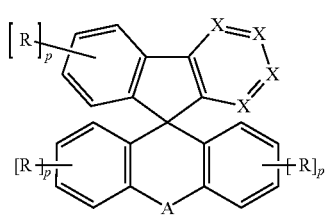

formula (1)

where the symbols and indices used are as follows:
A is O or S;
X two adjacent X are a group of the formula (2)

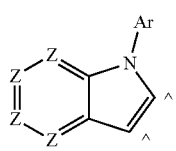

formula (2)

where ^ indicates the corresponding adjacent X groups in formula (1), and the two remaining X groups are CR;
Z is CR; or two adjacent Z are a group of the formula (2a) and the two other Z are CR,
formula (2a)

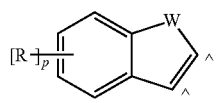

where ^ indicates the corresponding adjacent Z groups in formula (2); W here is O, S, NR or $CR_2$;
Ar is an aromatic or heteroaromatic ring system which has 5 to 40 aromatic ring atoms and may be substituted by one or more R radicals;
R is the same or different at each instance and is selected from the group consisting of H, D, F, Cl, Br, I, CN, $NO_2$, $N(Ar^1)_2$, $N(R^1)_2$, $P(Ar^1)_2$, $B(Ar^1)_2$, $Si(Ar^1)_3$, $Si(R^1)_3$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, each of which may be substituted by one or more $R^1$ radicals, where one or more nonadjacent $CH_2$ groups may be replaced by $R^1C=CR^1$, $C≡C$, $Si(R^1)_2$, $C=S$, $C=NR^1$, $SO_2$, $NR^1$, O, S or $CONR^1$ and where one or more hydrogen atoms may be replaced by D, F, Cl, Br, I, CN or $NO_2$, an aromatic ring system which has 5 to 60 aromatic ring atoms and may be substituted in each case by one or more $R^1$ radicals, an aryloxy or heteroaryloxy group which has 5 to 40 aromatic ring atoms and may be substituted by one or more $R^1$ radicals; at the same time, it is optionally possible for two adjacent R substituents to form a monocyclic or polycyclic, aliphatic, aromatic or heteroaromatic ring system which may be substituted by one or more $R^1$ radicals;
$Ar^1$ is the same or different at each instance and is an aromatic or heteroaromatic ring system which has 5 to 30 aromatic ring atoms and may be substituted by one or more nonaromatic $R^1$ radicals; at the same time, two $Ar^1$ radicals bonded to the same nitrogen, phosphorus, boron or silicon atom may also be bridged to one another by a single bond or a bridge selected from $N(R^1)$, $C(R^1)_2$, O and S;
$R^1$ is the same or different at each instance and is selected from the group consisting of H, D, F, CN, an aliphatic hydrocarbyl radical having 1 to 20 carbon atoms, or an aromatic or heteroaromatic ring system having 5 to 30 aromatic ring atoms in which one or more hydrogen atoms may be replaced by D, F, CN or an alkyl group having 1 to 10 carbon atoms; at the same time, two or more adjacent $R^1$ substituents together may form a mono- or polycyclic, aliphatic ring system;
p is the same or different at each instance and is 0, 1, 2, 3 or 4.

2. The compound as claimed in claim 1, where in the compound is selected from the compounds of the formulae (3) to (8)

formula (3)
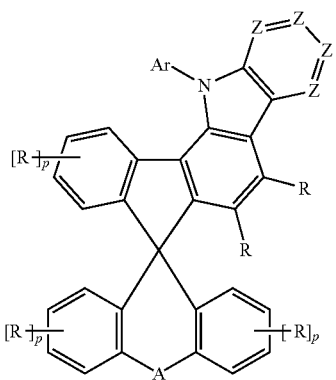
formula (4)
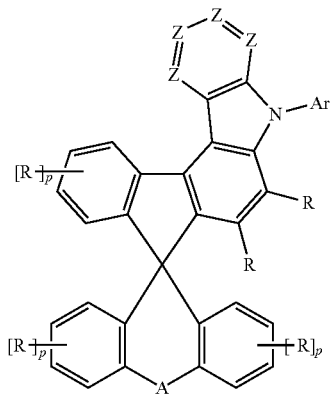
formula (5)
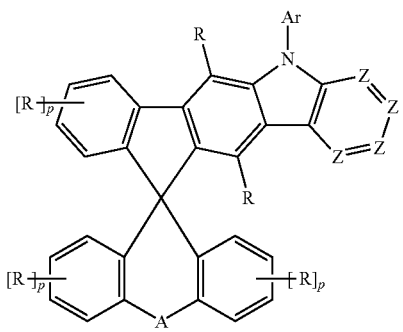
formula (6)
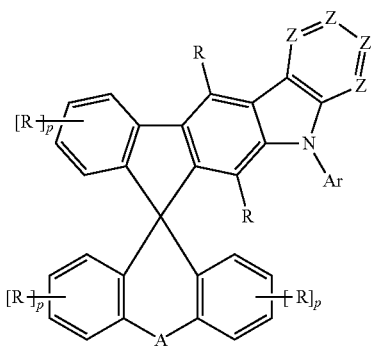
formula (7)
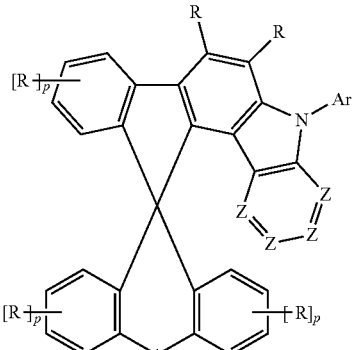
formula (8)
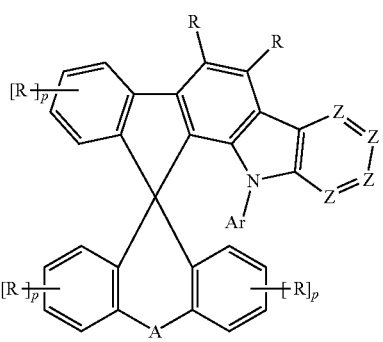
where the symbols and indices used have the definitions given in claim 1.
3. The compound as claimed in claim 1, wherein p is the same or different at each instance and is 0 or 1.
4. The compound as claimed in claim 1, wherein the compound is selected from the compounds of the formulae (3a) to (8a)
formula (3a)
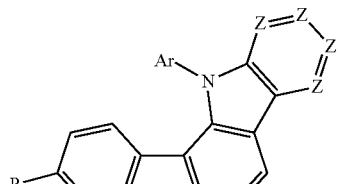
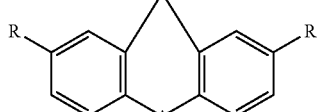
formula (4a)
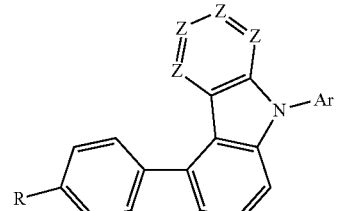
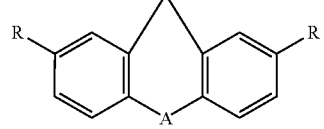

formula (5a)
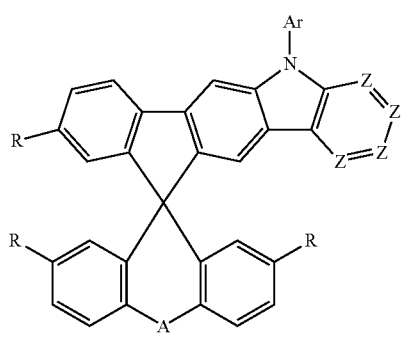
formula (6a)
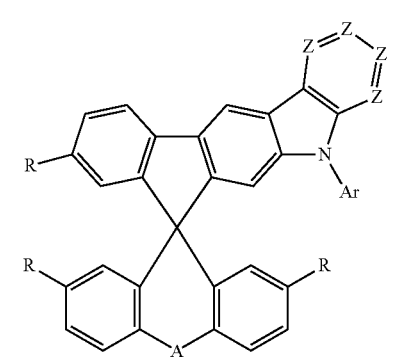
formula (7a)
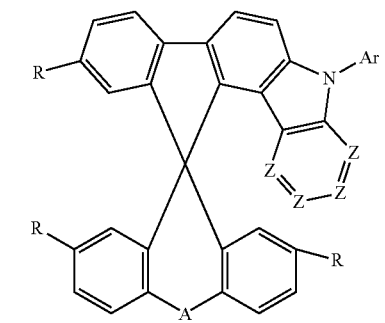
formula (8a)
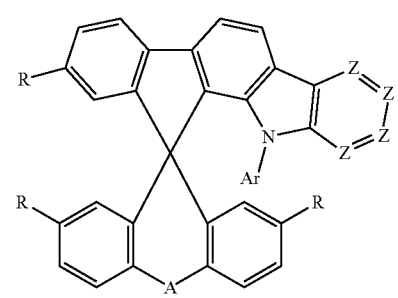
where the symbols used have the definitions given in claim 1.
5. The compound as claimed in claim 1, wherein the compound is selected from the compounds of the formulae (3b) to (8b)
formula (3b)
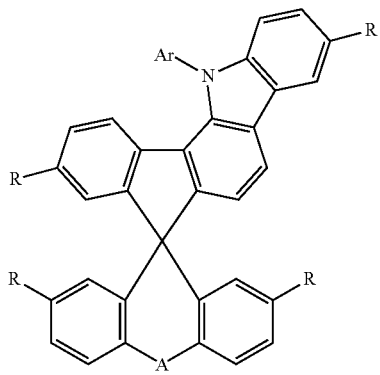
formula (4b)
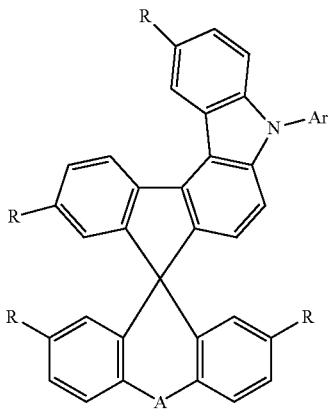
formula (5b)
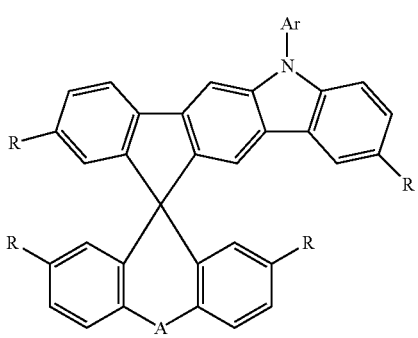
formula (6b)
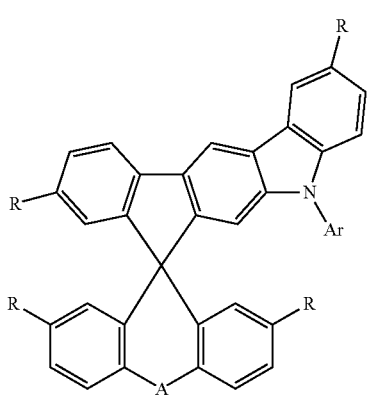

formula (7b)

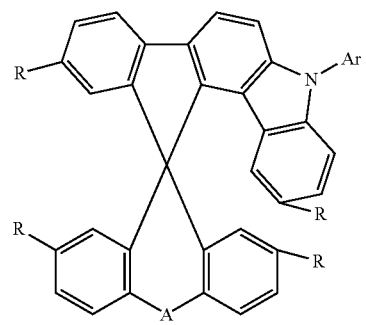

formula (8b)

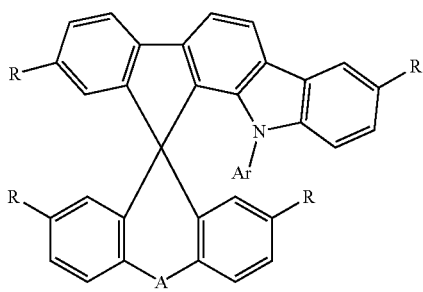

where the symbols used have the definitions given in claim 1.

6. The compound as claimed in claim 1, wherein A is oxygen.

7. The compound as claimed in claim 1, wherein the compound is selected from the compounds of the formulae (3d) to (8d)

formula (3d)

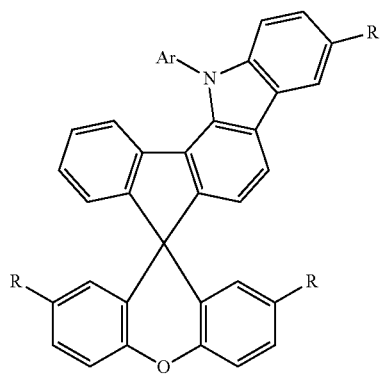

formula (4d)

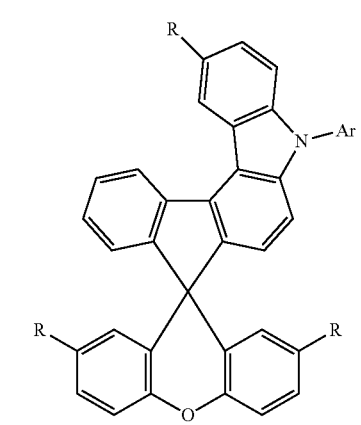

formula (5d)

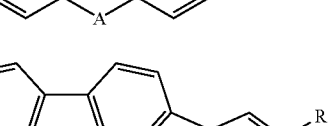

formula (6d)

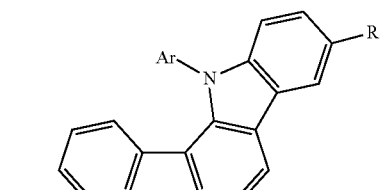

formula (7d)

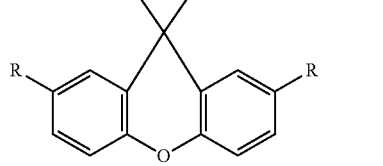

formula (8d)

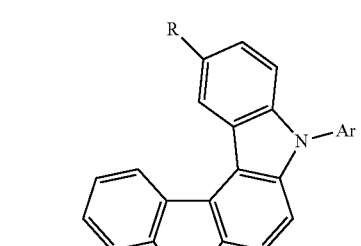

where the symbols used have the definitions given in claim 1.

8. The compound as claimed in claim 1, wherein Ar is selected from the group consisting of phenyl, biphenyl, terphenyl, quaterphenyl, fluorene, spirobifluorene, naphthalene, indole, benzofuran, benzothiophene, carbazole, dibenzofuran, dibenzothiophene, indenocarbazole, inclolocarbazole, pyridine, pyrimidine, pyrazine, pyridazine, triazine, phenanthrene, triphenylene and combinations of two or three of these groups, where these groups may each be substituted by one or more R radicals.

9. The compound as claimed in claim 1, wherein R is the same or different at each instance and is selected from the group consisting of H, D, F, CN, $N(Ar^1)_2$, $C(=O)Ar^1$, $P(=O)(Ar^1)_2$, a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more $R^1$ radicals, where one or more nonadjacent $CH_2$ groups may be replaced by O and where one or more hydrogen atoms may be replaced by D or F, or an aromatic ring system which has 5 to 30 aromatic ring atoms and may be substituted in each case by one or more $R^1$ radicals.

10. A process for preparing the compound as claimed in claim 1, comprising the reaction steps of:
   a) synthesizing the base skeleton which does not yet contain an Ar group; and
   b) converting the base skeleton from a) in a C—N coupling or in a nucleophilic aromatic substitution reaction for introduction of the Ar group.

11. A formulation comprising at least one compound as claimed in claim 1 and at least one solvent.

12. An electronic device comprising the formulation as claimed in claim 11.

13. An electronic device comprising at least one compound as claimed in claim 1.

14. An organic electroluminescent device which comprises the compound as claimed in claim 1 is used in an emitting layer as matrix material for phosphorescent emitters or in an electron transport layer or in a hole transport layer or in an exciton blocker layer or in a hole blocker layer.

* * * * *